United States Patent
Quadri et al.

(10) Patent No.: US 10,376,363 B2
(45) Date of Patent: Aug. 13, 2019

(54) REPLACEMENT MITRAL VALVE, DELIVERY SYSTEM FOR REPLACEMENT MITRAL VALVE AND METHODS OF USE

(71) Applicant: Edwards Lifesciences CardiAQ LLC, Irvine, CA (US)

(72) Inventors: Arshad Quadri, West Hartford, CT (US); J. Brent Ratz, Winchester, MA (US); Yen Liao, Arlington, VA (US); Julio Cesar Sanchez, Garden Grove, CA (US); Alexander H. Cooper, Costa Mesa, CA (US); Glen T. Rabito, Lake Forest, CA (US); Siddharth Vad, Irvine, CA (US); Luca Pesce, Huntington Beach, CA (US); Kevin M. Stewart, Newport Beach, CA (US); David Robert Landon, Costa Mesa, CA (US)

(73) Assignee: EDWARDS LIFESCIENCES CARDIAQ LLC, Irvine, CA (US)

( * ) Notice: Subject to any disclaimer, the term of this patent is extended or adjusted under 35 U.S.C. 154(b) by 75 days.

(21) Appl. No.: 15/141,684

(22) Filed: Apr. 28, 2016

(65) Prior Publication Data
US 2016/0317301 A1    Nov. 3, 2016

Related U.S. Application Data

(60) Provisional application No. 62/300,478, filed on Feb. 26, 2016, provisional application No. 62/210,165, (Continued)

(51) Int. Cl.
*A61F 2/24* (2006.01)

(52) U.S. Cl.
CPC .......... *A61F 2/2436* (2013.01); *A61F 2/2418* (2013.01); *A61F 2/2409* (2013.01); *A61F 2230/0065* (2013.01)

(58) Field of Classification Search
CPC ........ A61F 2/2436; A61F 2/962; A61F 2/966; A61F 2002/9505; A61F 2002/9665;
(Continued)

(56) References Cited

U.S. PATENT DOCUMENTS

| 3,657,744 A | 4/1972 | Ersek |
| 3,671,979 A | 6/1972 | Moulopoulos |

(Continued)

FOREIGN PATENT DOCUMENTS

| CA | 2304325 A1 | 10/2000 |
| CA | 2827556 A1 | 7/2012 |

(Continued)

OTHER PUBLICATIONS

Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.

(Continued)

*Primary Examiner* — Elizabeth Houston
*Assistant Examiner* — Charles M Wei
(74) *Attorney, Agent, or Firm* — Knobbe Martens Olson & Bear LLP

(57) ABSTRACT

Devices, systems and methods are described herein a prosthesis for implantation within a lumen or body cavity and delivery systems for delivering the prosthesis to a location for implantation. A delivery system can include a plurality of components, including a flexible nose cone, multi-layer (Continued)

sheath, and pre-compressed shaft, which can be moveable relative to each other.

19 Claims, 30 Drawing Sheets

Related U.S. Application Data filed on Aug. 26, 2015, provisional application No. 62/163,932, filed on May 19, 2015, provisional application No. 62/155,405, filed on Apr. 30, 2015.

(58) Field of Classification Search
CPC .... A61F 2/95–97; A61F 2/2427–2439; A61M 25/0012; A61M 25/0045; A61M 25/005; A61M 25/0144; A61M 25/0052; A61M 25/0054; A61M 25/0108; A61N 2001/0578; A61B 17/1214–12154; A61B 17/12168–12177
See application file for complete search history.

(56) References Cited

U.S. PATENT DOCUMENTS

| | | | |
|---|---|---|---|
| 3,739,402 A | | 6/1973 | Cooley et al. |
| 4,056,854 A | | 11/1977 | Boretos et al. |
| 4,079,468 A | | 3/1978 | Liotta et al. |
| 4,204,283 A | | 5/1980 | Bellhouse et al. |
| 4,222,126 A | | 9/1980 | Boretos et al. |
| 4,265,694 A | | 5/1981 | Boretos et al. |
| 4,339,831 A | | 7/1982 | Johnson |
| 4,340,977 A | | 7/1982 | Brownlee et al. |
| 4,470,157 A | | 9/1984 | Love |
| 4,477,930 A | | 10/1984 | Totten et al. |
| 4,490,859 A | | 1/1985 | Black et al. |
| 4,553,545 A | | 11/1985 | Maass et al. |
| 4,777,951 A | | 10/1988 | Cribier et al. |
| 4,865,600 A | | 9/1989 | Carpentier et al. |
| 4,994,077 A | | 2/1991 | Dobben |
| 5,007,898 A | * | 4/1991 | Rosenbluth ........... A61M 29/02 604/101.05 |
| 5,250,059 A | * | 10/1993 | Andreas ........... A61B 17/32078 604/22 |
| 5,326,371 A | | 7/1994 | Love et al. |
| 5,332,402 A | | 7/1994 | Teitelbaum |
| 5,370,685 A | | 12/1994 | Stevens |
| 5,415,667 A | | 5/1995 | Frater |
| 5,545,214 A | | 8/1996 | Stevens |
| 5,554,185 A | | 9/1996 | Block et al. |
| 5,571,135 A | * | 11/1996 | Fraser ...................... A61F 2/95 606/198 |
| 5,697,382 A | | 12/1997 | Love et al. |
| 5,840,081 A | | 11/1998 | Andersen et al. |
| 5,855,601 A | | 1/1999 | Bessler et al. |
| 5,957,949 A | | 9/1999 | Leonhardt et al. |
| 6,086,612 A | | 7/2000 | Jansen |
| 6,113,631 A | | 9/2000 | Jansen |
| 6,168,614 B1 | | 1/2001 | Andersen et al. |
| 6,251,093 B1 | | 6/2001 | Valley et al. |
| 6,312,465 B1 | | 11/2001 | Griffin et al. |
| 6,319,280 B1 | * | 11/2001 | Schoon ................ A61F 2/2427 606/1 |
| 6,358,277 B1 | | 3/2002 | Duran |
| 6,425,898 B1 | * | 7/2002 | Wilson ...................... A61F 2/95 606/108 |
| 6,440,164 B1 | | 8/2002 | DiMatteo et al. |
| 6,458,153 B1 | | 10/2002 | Bailey et al. |
| 6,482,228 B1 | | 11/2002 | Norred |
| 6,527,800 B1 | | 3/2003 | McGuckin, Jr. et al. |
| 6,582,462 B1 | | 6/2003 | Andersen et al. |
| 6,591,472 B1 | * | 7/2003 | Noone ............... A61M 25/0009 264/171.13 |
| 6,610,088 B1 | | 8/2003 | Gabbay |
| 6,629,534 B1 | | 10/2003 | St. Goar et al. |
| 6,652,578 B2 | | 11/2003 | Bailey et al. |
| 6,676,698 B2 | | 1/2004 | McGuckin, Jr. et al. |
| 6,695,878 B2 | | 2/2004 | McGuckin, Jr. et al. |
| 6,712,836 B1 | | 3/2004 | Berg et al. |
| 6,716,207 B2 | | 4/2004 | Farnholtz |
| 6,729,356 B1 | | 5/2004 | Baker et al. |
| 6,730,118 B2 | | 5/2004 | Spenser et al. |
| 6,746,422 B1 | | 6/2004 | Noriega et al. |
| 6,749,560 B1 | | 6/2004 | Konstorum et al. |
| 6,767,362 B2 | | 7/2004 | Schreck |
| 6,780,200 B2 | | 8/2004 | Jansen |
| 6,790,229 B1 | | 9/2004 | Berreklouw |
| 6,790,230 B2 | | 9/2004 | Beyersdorf et al. |
| 6,875,231 B2 | | 4/2005 | Anduiza et al. |
| 6,893,460 B2 | | 5/2005 | Spenser et al. |
| 6,908,481 B2 | | 6/2005 | Cribier |
| 7,018,406 B2 | | 3/2006 | Seguin et al. |
| 7,186,265 B2 | | 3/2007 | Sharkawy et al. |
| 7,192,440 B2 | | 3/2007 | Andreas et al. |
| 7,198,646 B2 | | 4/2007 | Figulla et al. |
| 7,201,772 B2 | | 4/2007 | Schwammenthal et al. |
| 7,276,078 B2 | | 10/2007 | Spenser et al. |
| 7,329,278 B2 | | 2/2008 | Seguin et al. |
| 7,381,219 B2 | | 6/2008 | Salahieh et al. |
| 7,393,360 B2 | | 7/2008 | Spenser et al. |
| 7,429,269 B2 | | 9/2008 | Schwammenthal et al. |
| 7,442,204 B2 | | 10/2008 | Schwammenthal et al. |
| 7,445,631 B2 | | 11/2008 | Salahieh et al. |
| 7,462,191 B2 | | 12/2008 | Spenser et al. |
| 7,510,575 B2 | | 3/2009 | Spenser et al. |
| 7,524,330 B2 | | 4/2009 | Berreklouw |
| 7,553,324 B2 | | 6/2009 | Andreas et al. |
| 7,585,321 B2 | | 9/2009 | Cribier |
| 7,618,446 B2 | | 11/2009 | Andersen et al. |
| 7,621,948 B2 | | 11/2009 | Herrmann et al. |
| 7,628,805 B2 | | 12/2009 | Spenser et al. |
| 7,748,389 B2 | | 7/2010 | Salahieh et al. |
| 7,753,949 B2 | | 7/2010 | Lamphere et al. |
| 7,803,185 B2 | | 9/2010 | Gabbay |
| 7,806,919 B2 | | 10/2010 | Bloom et al. |
| 7,815,673 B2 | | 10/2010 | Bloom et al. |
| 7,824,443 B2 | | 11/2010 | Salahieh et al. |
| 7,892,281 B2 | | 2/2011 | Seguin et al. |
| 7,914,569 B2 | | 3/2011 | Nguyen et al. |
| 7,947,075 B2 | | 5/2011 | Goetz et al. |
| 7,959,672 B2 | | 6/2011 | Salahieh et al. |
| 7,972,378 B2 | | 7/2011 | Tabor et al. |
| 7,981,151 B2 | | 7/2011 | Rowe |
| 7,993,392 B2 | | 8/2011 | Righini et al. |
| 8,016,877 B2 | | 9/2011 | Seguin et al. |
| 8,048,153 B2 | | 11/2011 | Salahieh et al. |
| 8,052,750 B2 | | 11/2011 | Tuval et al. |
| 8,070,800 B2 | | 12/2011 | Lock et al. |
| 8,070,802 B2 | | 12/2011 | Lamphere et al. |
| 8,075,615 B2 | | 12/2011 | Eberhardt et al. |
| 8,080,054 B2 | | 12/2011 | Rowe |
| 8,092,520 B2 | | 1/2012 | Quadri |
| 8,109,996 B2 | | 2/2012 | Stacchino et al. |
| 8,118,866 B2 | | 2/2012 | Herrmann et al. |
| 8,136,218 B2 | | 3/2012 | Millwee et al. |
| 8,137,398 B2 | | 3/2012 | Tuval et al. |
| 8,157,852 B2 | | 4/2012 | Bloom et al. |
| 8,167,934 B2 | | 5/2012 | Styrc et al. |
| 8,182,528 B2 | | 5/2012 | Salahieh et al. |
| 8,182,530 B2 | | 5/2012 | Huber |
| 8,206,427 B1 | * | 6/2012 | Ryan ........................ A61F 2/07 623/1.11 |
| 8,216,301 B2 | | 7/2012 | Bonhoeffer et al. |
| 8,219,229 B2 | | 7/2012 | Cao et al. |
| 8,220,121 B2 | | 7/2012 | Hendriksen et al. |
| 8,221,493 B2 | | 7/2012 | Boyle et al. |
| 8,226,710 B2 | | 7/2012 | Nguyen et al. |
| 8,236,045 B2 | | 8/2012 | Benichou et al. |
| 8,246,675 B2 | | 8/2012 | Zegdi |
| 8,246,678 B2 | | 8/2012 | Salahieh et al. |
| 8,252,051 B2 | | 8/2012 | Chau et al. |
| 8,252,052 B2 | | 8/2012 | Salahieh et al. |
| 8,287,584 B2 | | 10/2012 | Salahieh et al. |
| 8,303,653 B2 | | 11/2012 | Bonhoeffer et al. |

(56) References Cited

U.S. PATENT DOCUMENTS

| | | |
|---|---|---|
| 8,313,525 B2 | 11/2012 | Tuval et al. |
| 8,323,335 B2 | 12/2012 | Rowe et al. |
| 8,353,953 B2 | 1/2013 | Giannetti et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,470,023 B2 | 6/2013 | Eidenschink et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,733 B2 | 8/2013 | Watson |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,096 B2 | 8/2013 | Nelson |
| 8,518,106 B2 | 8/2013 | Duffy et al. |
| 8,562,663 B2 | 10/2013 | Mearns et al. |
| 8,579,963 B2 | 11/2013 | Tabor |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,566 B2 * | 11/2013 | Newell .................. A61F 2/82 623/1.11 |
| 8,591,570 B2 | 11/2013 | Revuelta et al. |
| 8,597,348 B2 | 12/2013 | Rowe et al. |
| 8,608,792 B2 * | 12/2013 | Silveira .................. A61F 2/07 623/1.11 |
| 8,617,236 B2 | 12/2013 | Paul et al. |
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 * | 2/2014 | Alon .................. A61F 2/2418 623/2.11 |
| 8,652,203 B2 | 2/2014 | Quadri et al. |
| 8,668,733 B2 | 3/2014 | Haug et al. |
| 8,673,000 B2 | 3/2014 | Tabor et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,721,708 B2 | 5/2014 | Seguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,758,432 B2 | 6/2014 | Solem |
| 8,764,818 B2 | 7/2014 | Gregg |
| 8,771,344 B2 | 7/2014 | Tran et al. |
| 8,771,345 B2 | 7/2014 | Tuval et al. |
| 8,771,346 B2 | 7/2014 | Tuval et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,356 B2 | 8/2014 | Quadri et al. |
| 8,795,357 B2 | 8/2014 | Yohanan et al. |
| 8,808,356 B2 | 8/2014 | Braido et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,845,718 B2 | 9/2014 | Tuval et al. |
| 8,858,620 B2 | 10/2014 | Salahieh et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,911,455 B2 | 12/2014 | Quadri et al. |
| 8,926,693 B2 | 1/2015 | Duffy et al. |
| 8,926,694 B2 | 1/2015 | Costello |
| 8,939,960 B2 | 1/2015 | Rosenman et al. |
| 8,945,209 B2 | 2/2015 | Bonyuet et al. |
| 8,951,299 B2 | 2/2015 | Paul et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,372 B2 | 3/2015 | Murry, III et al. |
| 8,986,375 B2 | 3/2015 | Garde et al. |
| 8,992,608 B2 | 3/2015 | Haug et al. |
| 8,998,979 B2 | 4/2015 | Seguin et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,034,033 B2 | 5/2015 | McLean et al. |
| 9,039,757 B2 | 5/2015 | McLean et al. |
| 9,055,937 B2 | 6/2015 | Rowe et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,084,676 B2 | 7/2015 | Chau et al. |
| 9,125,738 B2 | 9/2015 | Figulla et al. |
| 9,138,312 B2 | 9/2015 | Tuval et al. |
| 9,161,834 B2 | 10/2015 | Taylor et al. |
| 9,173,737 B2 | 11/2015 | Hill et al. |
| 9,180,004 B2 | 11/2015 | Alkhatib |
| 9,186,249 B2 | 11/2015 | Rolando et al. |
| 9,220,594 B2 | 12/2015 | Braido et al. |
| 9,241,790 B2 | 1/2016 | Lane et al. |
| 9,248,014 B2 | 2/2016 | Lane et al. |
| 9,277,990 B2 | 3/2016 | Klima et al. |
| 9,277,993 B2 | 3/2016 | Gamarra et al. |
| 9,289,291 B2 | 3/2016 | Gorman, III et al. |
| 9,289,296 B2 | 3/2016 | Braido et al. |
| 9,295,551 B2 | 3/2016 | Straubinger et al. |
| 9,308,110 B2 * | 4/2016 | Newell .................. A61F 2/82 |
| D755,384 S | 5/2016 | Pesce et al. |
| 9,326,815 B2 | 5/2016 | Watson |
| 9,331,328 B2 | 5/2016 | Eberhardt et al. |
| 9,339,382 B2 | 5/2016 | Tabor et al. |
| 9,351,831 B2 | 5/2016 | Braido et al. |
| 9,351,832 B2 | 5/2016 | Braido et al. |
| 9,364,321 B2 | 6/2016 | Alkhatib et al. |
| 9,439,795 B2 * | 9/2016 | Wang .................. A61F 2/2436 |
| 9,445,897 B2 | 9/2016 | Bishop et al. |
| 9,456,877 B2 | 10/2016 | Weitzner et al. |
| 9,675,488 B2 * | 6/2017 | Newell .................. A61F 2/82 |
| 9,681,951 B2 | 6/2017 | Ratz et al. |
| 9,681,968 B2 | 6/2017 | Goetz et al. |
| 9,700,329 B2 | 7/2017 | Metzger et al. |
| 9,700,411 B2 | 7/2017 | Klima et al. |
| 9,724,221 B2 * | 8/2017 | Brown .................. A61F 2/962 |
| D800,908 S | 10/2017 | Hariton et al. |
| 9,795,479 B2 | 10/2017 | Lim |
| 9,833,313 B2 | 12/2017 | Board et al. |
| 9,861,477 B2 | 1/2018 | Lafontaine |
| 10,130,789 B2 * | 11/2018 | Shimada .......... A61M 25/0053 |
| 2002/0029046 A1 * | 3/2002 | Lorentzen Cornelius .................. A61F 2/958 606/108 |
| 2002/0032481 A1 | 3/2002 | Gabbay |
| 2002/0045929 A1 | 4/2002 | Diaz |
| 2002/0052644 A1 | 5/2002 | Shaolian et al. |
| 2003/0083654 A1 * | 5/2003 | Chin .................. A61B 18/1492 606/41 |
| 2003/0105517 A1 | 6/2003 | White et al. |
| 2003/0120333 A1 | 6/2003 | Ouriel et al. |
| 2003/0130729 A1 | 7/2003 | Paniagua et al. |

(56) References Cited

U.S. PATENT DOCUMENTS

| | | |
|---|---|---|
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0117009 A1 | 6/2004 | Cali et al. |
| 2004/0133273 A1 | 7/2004 | Cox |
| 2004/0186561 A1 | 9/2004 | McGuckin et al. |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2005/0033398 A1 | 2/2005 | Seguin |
| 2005/0043682 A1* | 2/2005 | Kucklick ............ A61B 17/3421 604/164.09 |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137693 A1 | 6/2005 | Haug et al. |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2005/0283231 A1 | 12/2005 | Haug et al. |
| 2006/0020327 A1 | 1/2006 | Lashinski et al. |
| 2006/0030835 A1* | 2/2006 | Sherman ................ A61F 2/958 604/526 |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0241745 A1 | 10/2006 | Solem |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0010876 A1 | 1/2007 | Salahieh et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0203560 A1 | 8/2007 | Forster et al. |
| 2007/0213813 A1 | 9/2007 | Von Segesser et al. |
| 2007/0255305 A1* | 11/2007 | McMichael ......... A61B 17/3421 606/191 |
| 2007/0255394 A1 | 11/2007 | Ryan |
| 2008/0015569 A1* | 1/2008 | Saadat ................ A61B 1/0008 606/41 |
| 2008/0021546 A1 | 1/2008 | Patz et al. |
| 2008/0027528 A1* | 1/2008 | Jagger ..................... A61F 2/95 623/1.11 |
| 2008/0071366 A1 | 3/2008 | Tuval et al. |
| 2008/0082164 A1 | 4/2008 | Friedman |
| 2008/0082165 A1 | 4/2008 | Wilson et al. |
| 2008/0097581 A1 | 4/2008 | Shanley |
| 2008/0114442 A1* | 5/2008 | Mitchell ................. A61F 2/07 623/1.13 |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0228254 A1 | 9/2008 | Ryan |
| 2009/0005863 A1 | 1/2009 | Goetz et al. |
| 2009/0112186 A1* | 4/2009 | Adams ................ A61J 15/0015 604/524 |
| 2009/0138079 A1 | 5/2009 | Tuval et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0270972 A1 | 10/2009 | Lane |
| 2009/0275945 A1* | 11/2009 | Makower ............... A61B 17/58 606/60 |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0287290 A1 | 11/2009 | Macaulay et al. |
| 2009/0287292 A1* | 11/2009 | Becking ..................... A61F 2/95 623/1.11 |
| 2009/0287296 A1 | 11/2009 | Manasse |
| 2009/0292350 A1 | 11/2009 | Eberhardt et al. |
| 2009/0306768 A1 | 12/2009 | Quadri |
| 2010/0114305 A1 | 5/2010 | Kang et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0249915 A1 | 9/2010 | Zhang |
| 2010/0252470 A1 | 10/2010 | Ryan et al. |
| 2010/0256723 A1 | 10/2010 | Murray |
| 2010/0298931 A1 | 11/2010 | Quadri et al. |
| 2010/0305685 A1 | 12/2010 | Millwee et al. |
| 2011/0004296 A1 | 1/2011 | Lutter et al. |
| 2011/0029067 A1 | 2/2011 | McGuckin, Jr. et al. |
| 2011/0034987 A1* | 2/2011 | Kennedy ................... A61F 2/95 623/1.11 |
| 2011/0202128 A1* | 8/2011 | Duffy ..................... A61F 2/966 623/2.11 |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0257720 A1* | 10/2011 | Peterson ................... A61F 2/95 623/1.11 |
| 2011/0264196 A1 | 10/2011 | Savage et al. |
| 2011/0313515 A1 | 12/2011 | Quadri et al. |
| 2012/0022639 A1 | 1/2012 | Hacohen et al. |
| 2012/0022640 A1 | 1/2012 | Gross et al. |
| 2012/0041550 A1 | 2/2012 | Salahieh et al. |
| 2012/0053685 A1 | 3/2012 | Cerf et al. |
| 2012/0059454 A1 | 3/2012 | Millwee et al. |
| 2012/0071969 A1 | 3/2012 | Li et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0215303 A1 | 8/2012 | Quadri et al. |
| 2012/0239142 A1* | 9/2012 | Liu ....................... A61F 2/0095 623/2.11 |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2013/0006294 A1 | 1/2013 | Kashkarov et al. |
| 2013/0035759 A1 | 2/2013 | Gross et al. |
| 2013/0053950 A1 | 2/2013 | Rowe et al. |
| 2013/0131788 A1 | 5/2013 | Quadri et al. |
| 2013/0144378 A1 | 6/2013 | Quadri et al. |
| 2013/0172851 A1* | 7/2013 | Shimada ........... A61M 25/0053 604/508 |
| 2013/0211508 A1 | 8/2013 | Lane et al. |
| 2013/0226276 A1* | 8/2013 | Newell ..................... A61F 2/82 623/1.11 |
| 2013/0226278 A1* | 8/2013 | Newell ..................... A61F 2/82 623/1.12 |
| 2013/0253635 A1 | 9/2013 | Straubinger et al. |
| 2013/0253642 A1 | 9/2013 | Brecker |
| 2013/0282113 A1 | 10/2013 | Punga et al. |
| 2013/0297013 A1 | 11/2013 | Klima et al. |
| 2013/0304185 A1* | 11/2013 | Newell ..................... A61F 2/82 623/1.12 |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0000112 A1 | 1/2014 | Braido et al. |

(56) References Cited

U.S. PATENT DOCUMENTS

| | | |
|---|---|---|
| 2014/0018912 A1 | 1/2014 | Delaloye et al. |
| 2014/0025150 A1* | 1/2014 | Lim ................. A61F 2/966 623/1.11 |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0052242 A1 | 2/2014 | Revuelta et al. |
| 2014/0081375 A1 | 3/2014 | Bardill et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0200660 A1 | 7/2014 | Savage et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0222031 A1* | 8/2014 | Stack ................. A61B 17/3421 606/144 |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0222144 A1 | 8/2014 | Eberhardt et al. |
| 2014/0230515 A1 | 8/2014 | Tuval et al. |
| 2014/0236288 A1 | 8/2014 | Lambrecht et al. |
| 2014/0243969 A1 | 8/2014 | Venkatasubramanian et al. |
| 2014/0257240 A1* | 9/2014 | Burdulis ............ A61B 17/3401 604/506 |
| 2014/0257467 A1 | 9/2014 | Lane et al. |
| 2014/0277390 A1 | 9/2014 | Ratz et al. |
| 2014/0277402 A1 | 9/2014 | Essinger et al. |
| 2014/0277411 A1 | 9/2014 | Bortlein et al. |
| 2014/0277422 A1 | 9/2014 | Ratz et al. |
| 2014/0277425 A1 | 9/2014 | Dakin |
| 2014/0277426 A1 | 9/2014 | Dakin et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0005863 A1 | 1/2015 | Para |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0032198 A1* | 1/2015 | Folk ................. A61F 2/966 623/1.12 |
| 2015/0039083 A1 | 2/2015 | Rafiee |
| 2015/0045880 A1 | 2/2015 | Hacohen |
| 2015/0142103 A1 | 5/2015 | Vidlund |
| 2015/0148731 A1 | 5/2015 | McNamara et al. |
| 2015/0157457 A1 | 6/2015 | Hacohen |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0297346 A1 | 10/2015 | Duffy et al. |
| 2015/0297383 A1* | 10/2015 | Brown ................. A61F 2/966 623/1.12 |
| 2015/0305943 A1* | 10/2015 | Hossainy ............. A61F 11/002 604/514 |
| 2015/0327994 A1 | 11/2015 | Morriss et al. |
| 2015/0327996 A1 | 11/2015 | Fahim et al. |
| 2015/0328000 A1 | 11/2015 | Ratz et al. |
| 2015/0328001 A1 | 11/2015 | McLean et al. |
| 2015/0335429 A1 | 11/2015 | Morriss et al. |
| 2015/0351903 A1 | 12/2015 | Morriss et al. |
| 2015/0351906 A1 | 12/2015 | Hammer et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0143732 A1 | 5/2016 | Glimsdale |
| 2016/0158003 A1 | 6/2016 | Wallace et al. |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0270910 A1 | 9/2016 | Birmingham et al. |
| 2016/0279386 A1 | 9/2016 | Dale et al. |
| 2016/0310267 A1 | 10/2016 | Zeng et al. |
| 2017/0106166 A1* | 4/2017 | Wang ................. A61M 25/0015 |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0312075 A1 | 11/2017 | Fahim et al. |
| 2017/0325954 A1 | 11/2017 | Perszyk |
| 2017/0348096 A1 | 12/2017 | Anderson |
| 2017/0367823 A1 | 12/2017 | Hariton et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |

FOREIGN PATENT DOCUMENTS

| | | |
|---|---|---|
| DE | 102006052564 B3 | 12/2007 |
| EP | 1171059 A1 | 1/2002 |
| EP | 1369098 A1 | 12/2003 |
| EP | 1259194 B1 | 2/2005 |
| EP | 1255510 B1 | 4/2007 |
| EP | 1827558 A2 | 9/2007 |
| EP | 1239901 B1 | 10/2007 |
| EP | 1472996 B1 | 9/2009 |
| EP | 1935377 B1 | 3/2010 |
| EP | 2238947 A2 | 10/2010 |
| EP | 2308425 A1 | 4/2011 |
| EP | 2398543 A1 | 12/2011 |
| EP | 1281375 B1 | 2/2012 |
| EP | 2496182 A1 | 9/2012 |
| EP | 2285317 B1 | 12/2012 |
| EP | 2566416 A1 | 3/2013 |
| EP | 2319458 B1 | 4/2013 |
| EP | 2124826 B1 | 7/2014 |
| EP | 2750630 A1 | 7/2014 |
| EP | 2777617 A1 | 9/2014 |
| EP | 2745805 B1 | 6/2015 |

(56) References Cited

FOREIGN PATENT DOCUMENTS

| | | |
|---|---|---|
| EP | 2749254 B1 | 6/2015 |
| EP | 2898858 A1 | 7/2015 |
| EP | 1734903 B1 | 10/2015 |
| EP | 2926766 B1 | 10/2015 |
| EP | 2967858 A2 | 1/2016 |
| EP | 2985006 A1 | 2/2016 |
| EP | 2168536 B1 | 4/2016 |
| EP | 2815725 B1 | 4/2016 |
| EP | 2237746 B1 | 5/2016 |
| EP | 2815723 B1 | 7/2016 |
| EP | 2262451 B1 | 5/2017 |
| EP | 3184083 A1 | 6/2017 |
| EP | 2446915 B1 | 1/2018 |
| EP | 3057541 B1 | 1/2018 |
| EP | 3037064 B1 | 3/2018 |
| EP | 3046511 B1 | 3/2018 |
| EP | 3142603 B1 | 3/2018 |
| EP | 3294220 A1 | 3/2018 |
| GB | 1264471 A | 2/1972 |
| GB | 1315844 A | 5/1973 |
| GB | 2398245 A | 8/2004 |
| JP | 2002540889 A | 12/2002 |
| JP | 2008541865 A | 11/2008 |
| WO | 0061034 A1 | 10/2000 |
| WO | 03092554 A1 | 11/2003 |
| WO | 2004030569 A2 | 4/2004 |
| WO | 2005011534 A1 | 2/2005 |
| WO | 2006070372 A2 | 7/2006 |
| WO | 2006085225 A1 | 8/2006 |
| WO | 2006089236 A1 | 8/2006 |
| WO | 2006127765 A1 | 11/2006 |
| WO | 2007025028 A1 | 3/2007 |
| WO | 2007058857 A2 | 5/2007 |
| WO | 2007123658 A1 | 11/2007 |
| WO | 2008013915 A2 | 1/2008 |
| WO | 2008070797 A2 | 6/2008 |
| WO | 2008103722 A2 | 8/2008 |
| WO | 2008125153 A1 | 10/2008 |
| WO | 2008150529 A1 | 12/2008 |
| WO | 2009026563 A2 | 2/2009 |
| WO | 2009033469 A1 | 3/2009 |
| WO | 2009045331 A1 | 4/2009 |
| WO | 2009053497 A1 | 4/2009 |
| WO | 2009091509 A1 | 7/2009 |
| WO | 2009094500 A1 | 7/2009 |
| WO | 2009134701 A2 | 11/2009 |
| WO | 2010005524 A2 | 1/2010 |
| WO | 2010008549 A1 | 1/2010 |
| WO | 2010022138 A2 | 2/2010 |
| WO | 2010037141 A1 | 4/2010 |
| WO | 2010040009 A1 | 4/2010 |
| WO | 2010057262 A1 | 5/2010 |
| WO | 2011025945 A1 | 3/2011 |
| WO | 2011057087 A1 | 5/2011 |
| WO | 2011111047 A2 | 9/2011 |
| WO | 2011137531 A1 | 11/2011 |
| WO | 2012177942 A2 | 12/2012 |
| WO | 2013028387 A2 | 2/2013 |
| WO | 2013059747 A1 | 4/2013 |
| WO | 2013075215 A1 | 5/2013 |
| WO | 2013120181 A1 | 8/2013 |
| WO | 2013166356 A2 | 11/2013 |
| WO | 2013175468 A2 | 11/2013 |
| WO | 2013192305 A2 | 12/2013 |
| WO | 2014018432 A2 | 1/2014 |
| WO | 2014099655 A1 | 6/2014 |
| WO | 2014110019 A1 | 7/2014 |
| WO | 2014110171 A2 | 7/2014 |
| WO | 2014121042 A1 | 8/2014 |
| WO | 2014139545 A1 | 9/2014 |
| WO | 2014145338 A1 | 9/2014 |
| WO | 2014149865 A1 | 9/2014 |
| WO | 2014163706 A1 | 10/2014 |
| WO | 2014164364 A1 | 10/2014 |
| WO | 2014194178 A1 | 12/2014 |
| WO | 2014204807 A1 | 12/2014 |
| WO | 2014205064 A1 | 12/2014 |
| WO | 2015077274 A1 | 5/2015 |
| WO | 2015148241 A1 | 10/2015 |
| WO | 2016016899 A1 | 2/2016 |

OTHER PUBLICATIONS

Bavaria, Joseph E. M.D. et al.: "Transcatheter Mitral Valve Implantation: The Future Gold Standard for MR?," Applicant requests the Examiner to consider this reference to be prior art as of Dec. 2010.
Int'l. Search Report for PCT/US2016/030191, dated Aug. 8, 2016.
Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.
Bavaria, Joseph E. M.D.: "CardiAQ Valve Technologies: Transcatheter Mitral Valve Implantation," Sep. 21, 2009.
Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 7, 2011.
Boudjemline, Younes, et al., "Steps Toward the Percutaneous Replacement of Atrioventricular Valves," JACC, vol. 16, No. 2, Jul. 19, 2005:360-5.
Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.
Condado, Jose Antonio, et al., "Percutaneous Treatment of Heart Valves," Rev Esp Cardio. 2006;59(12):1225-31, Applicant believes this may have been available as early as Dec. 2006.
Vu, Duc-Thang, et al., "Novel Sutureless Mitral Valve Implantation Method Involving a Bayonet Insertion and Release Mechanism: A Proof of Concept Study in Pigs," The Journal of Thoracic and Cardiovascular Surgery, vol. 143, No. 4, 985-988, Apr. 2012, Applicant believes this may have been available online as early as Feb. 13, 2012.
Fanning, Jonathon P., et al., "Transcatheter Aortic Valve Implantation (TAVI): Valve Design and Evolution," International Journal of Cardiology 168 (2013) 1822-1831, Applicant believes this may have been available as early as Oct. 3, 2013.
Spillner, J. et al., "New Sutureless 'Atrial-Mitral-Valve Prosthesis' for Minimally Invasive Mitral Valve Therapy," Textile Research Journal, 2010, in 7 pages, Applicant believes this may have been available as early as Aug. 9, 2010.
Karimi, Houshang, et al., "Percutaneous Valve Therapies," SIS 2007 Yearbook, Chapter 11, pp. 1-11.
Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.
Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.
Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. 2005.
Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.

(56) References Cited

OTHER PUBLICATIONS

Seidel, Wolfgang, et al., "A Mitral Valve Prosthesis and a Study of Thrombosis on Heart Valves in Dogs," JSR—vol. II, No. 3—May, 1962, submitted for publication Oct. 9, 1961.
Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.
Webb, John G., et al., "Transcatheter Aortic Valve Implantation: The Evolution of Prostheses, Delivery Systems and Approaches," Archives of Cardiovascular Disease (2012) 105, 153-159. Applicant believes this may have been available as early as Mar. 16, 2012.
Sondergaard, Lars, et al., "Transcatheter Mitral Valve Implantation: CardiAQ™," Applicant believes this may have been presented at TCT 2013.
Sondergaard, Lars, et al., "Transcatheter Mitral Valve Implantation: CardiAQ™," Applicant believes this may have been presented at EuroPCR 2013.
Sondergaard, Lars, "CardiAQ TMVR FIH—Generation 2," Applicants believe this may have been presented in 2014 at the TVT symposium.
CardiAQ Valve Technologies, "Innovations in Heart Valve Therapy," In3 San Francisco, Jun. 18, 2008, PowerPoint presentation in 19 slides.
Ratz, J. Brent, "LSI EMT Spotlight," May 15, 2009.
Ratz, J. Brent, "In3 Company Overview," Jun. 24, 2009.
"Company Overview," at TVT on Jun. 25, 2009.
Ruiz, Carlos E., "Overview of Novel Transcatheter Valve Technologies," Applicant believes this may have been presented on May 27, 2010 at EuroPCR.
"Update," Applicant believes this may have been presented on Jun. 6, 2010 at TVT.
Mack, Michael, M.D., "Antegrade Transcatheter Mitral valve Implantation: A Short-term Experience in Swine Model," Applicant believes this may have been presented on May of 2011 at TVT.
Mack, Michael, M.D., "Antegrade Transcatheter Mitral valve Implantation: On-Going Experience in Swine Model," Applicant believes this may have been presented on November of 2011 at TCT.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.
Quadri, Arshad M.D., "Transcatheter Mitral Valve Implantation (TMVI) (An Acute In Vivo Study)," Applicant believes his may have been presented on Sep. 22, 2010 at TCT.
Masson, Jean-Bernard, et al., "Percutaneous Treatment of Mitral Regurgitation," Circulation: Cardiovascular Interventions, 2:140-146, Applicant believes this may have been available as early as Apr. 14, 2009.
Horvath et al.: "Transapical Aortic Valve Replacement under Real-time Magnetic Resonance Imaging Guidance: Experimental Results with Balloon-Expandable and Self-Expanding Stents," http://www.ncbi.nlm.nih.gov/pmc/articles/PMC3038190/. Jun. 2011.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.

Van Mieghem, et al., "Anatomy of the Mitral Valvular Complex and Its Implications for Transcatheter Interventions for Mitral Regurgitation," J. Am. Coll. Cardiol., 56:617-626 (Aug. 17, 2010).
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2011.
Grube, E et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as August of 2008.
Feldman, Ted, MD. "Prospects for Percutaneous Valve Therapies," Circulation 2007;116:2866-2877. Applicant believes that this may be available as early as Dec. 11, 2007.
Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as June of 2014.
Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.
BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.
BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.
"CardiAQTM Valve Technologies reports Successful First-in-Human Trans-Apical implantation of its Second Generation Transcatheter Mitral Valve," CardiAQ Valve Technologies Press Release, May 20, 2014.
Dave Fornell, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.
The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Neovasc corporate presentation, Oct. 2009, available at http://www.neovasc.com/investors/documents/Neovasc-Corporate-Presentation-October-2009.pdf.
NIJ350: Vote for Your Favorite New Jersey Innovations, Jun. 27, 2014, http://www.kilmerhouse.com/2014/06/nj350-vote-for-your-favorite-new-jersey-innovations/.

\* cited by examiner

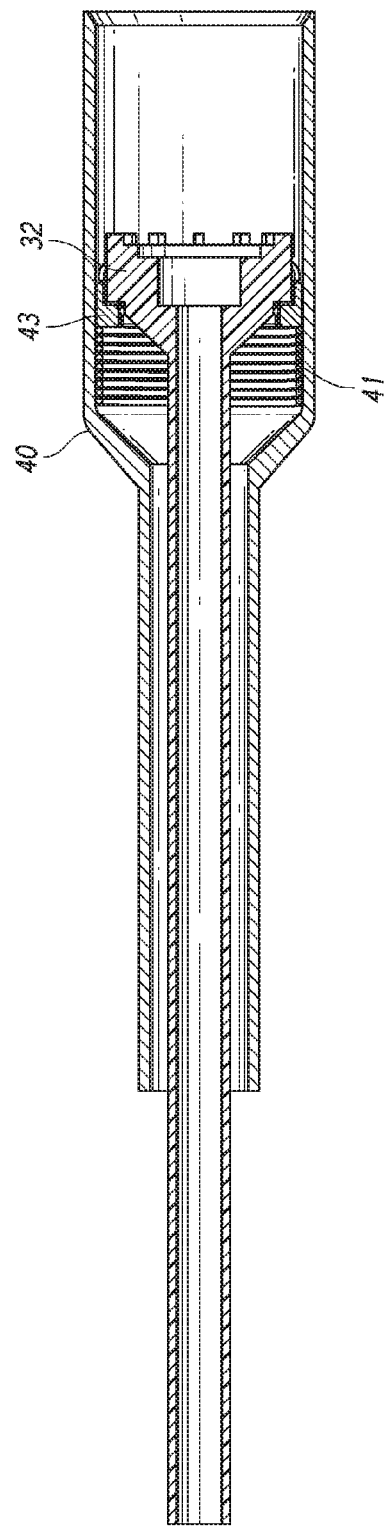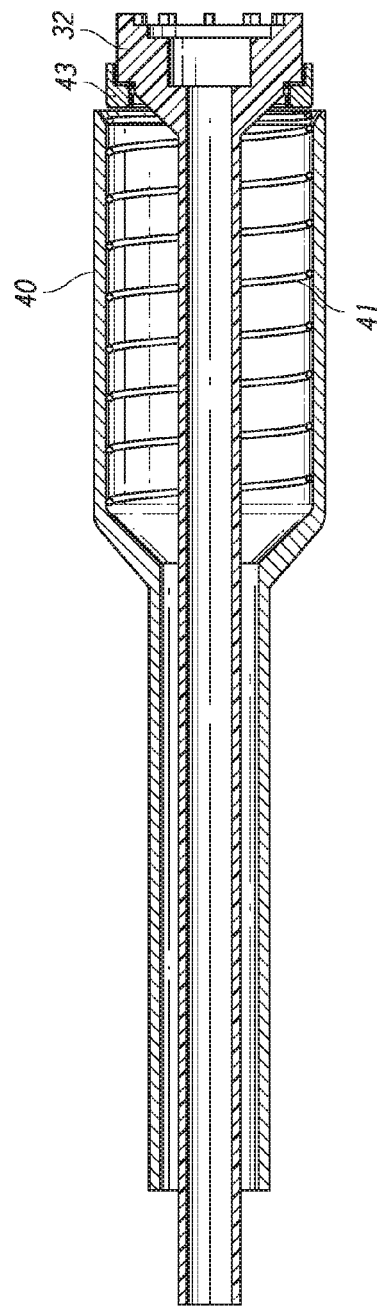
FIG. 5B
FIG. 5C

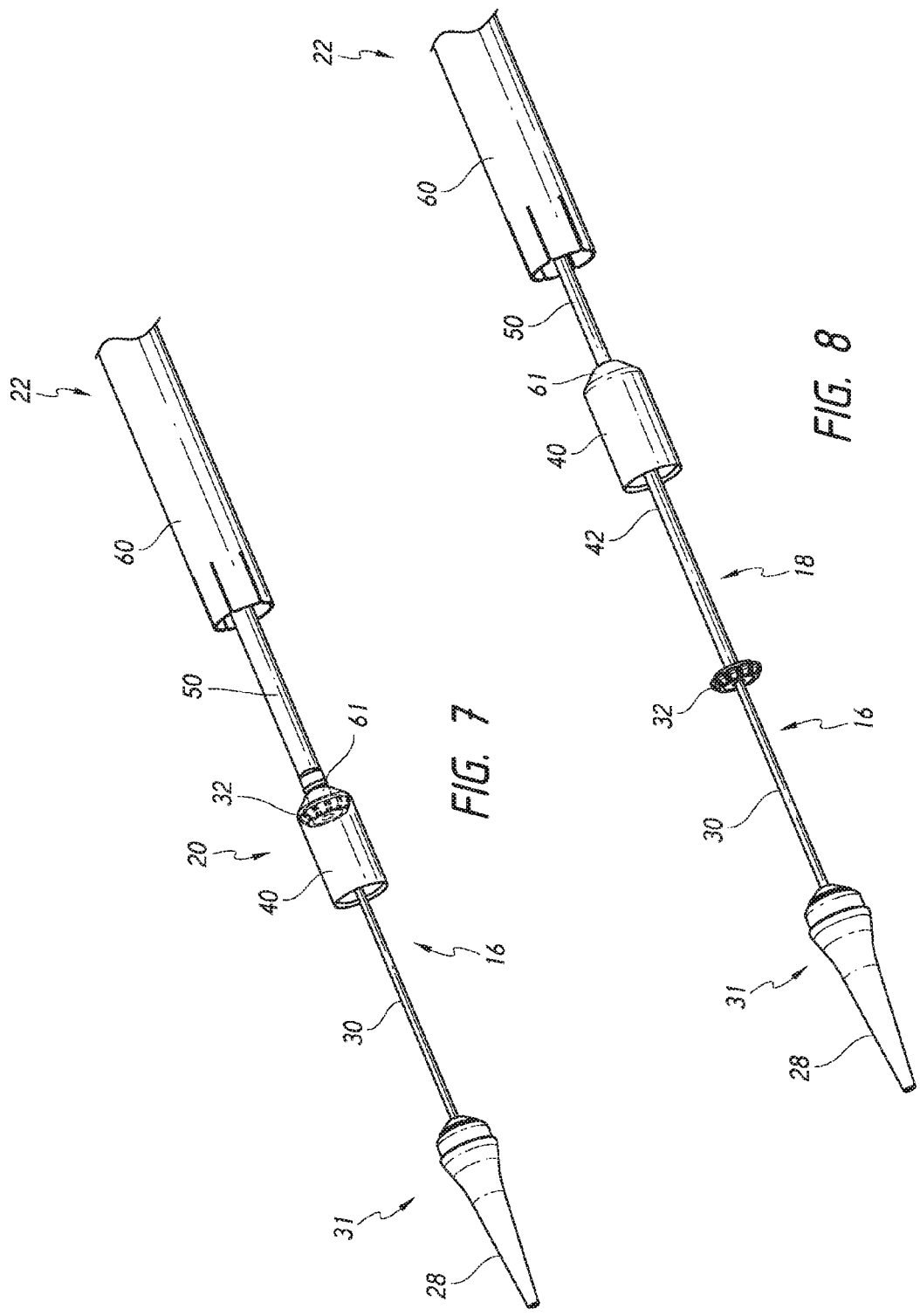

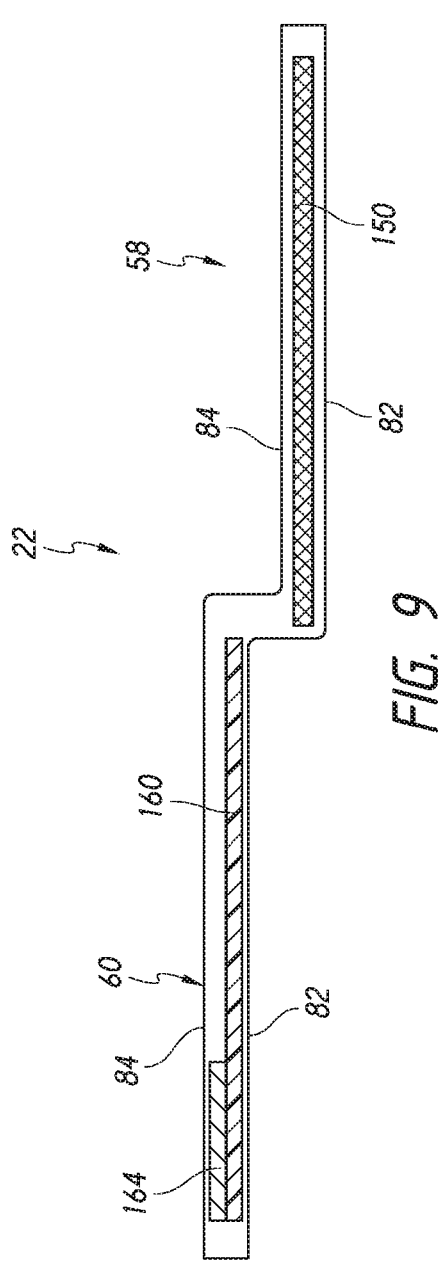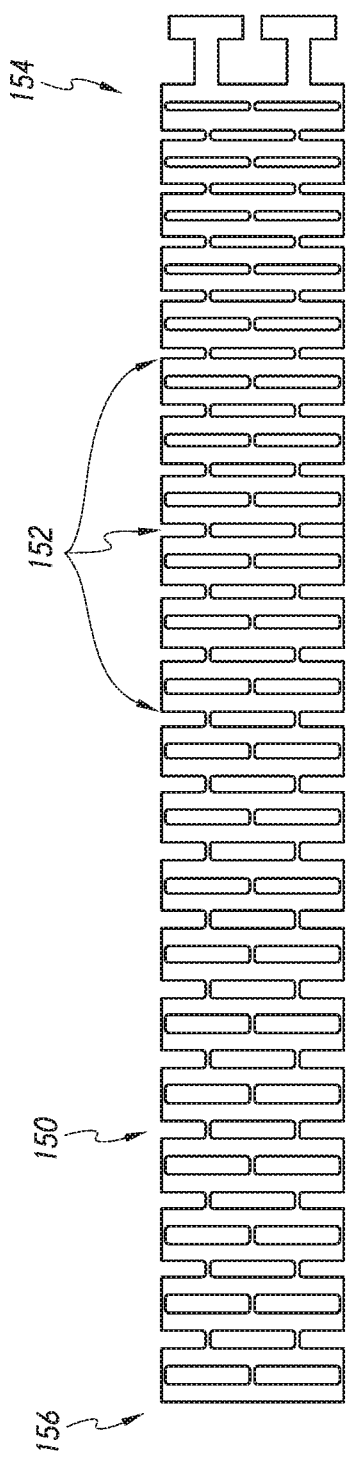

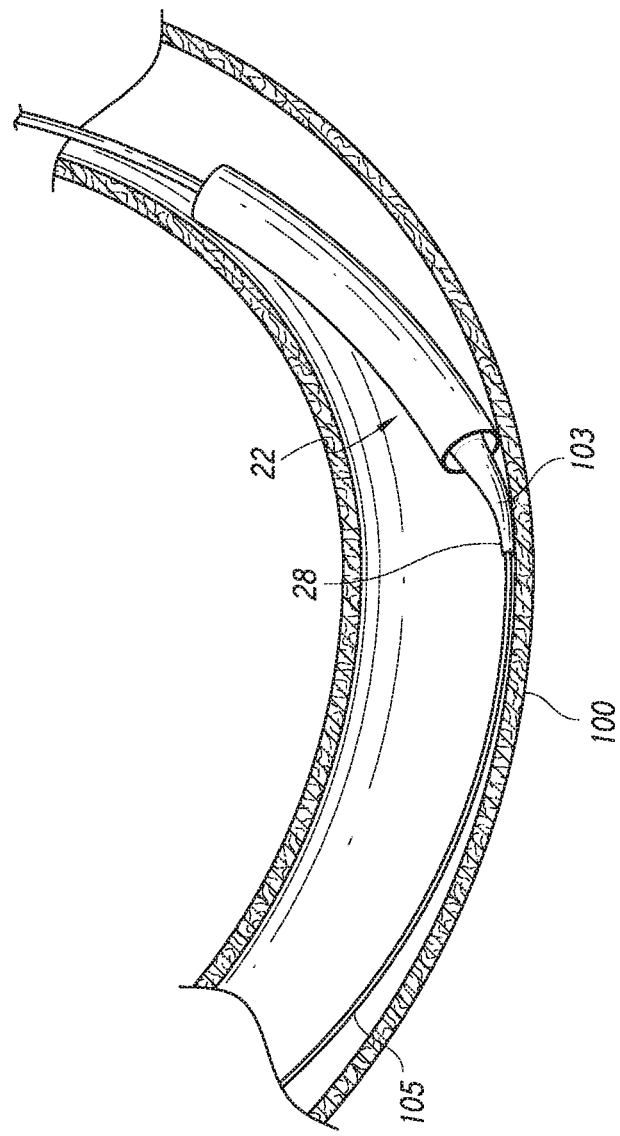

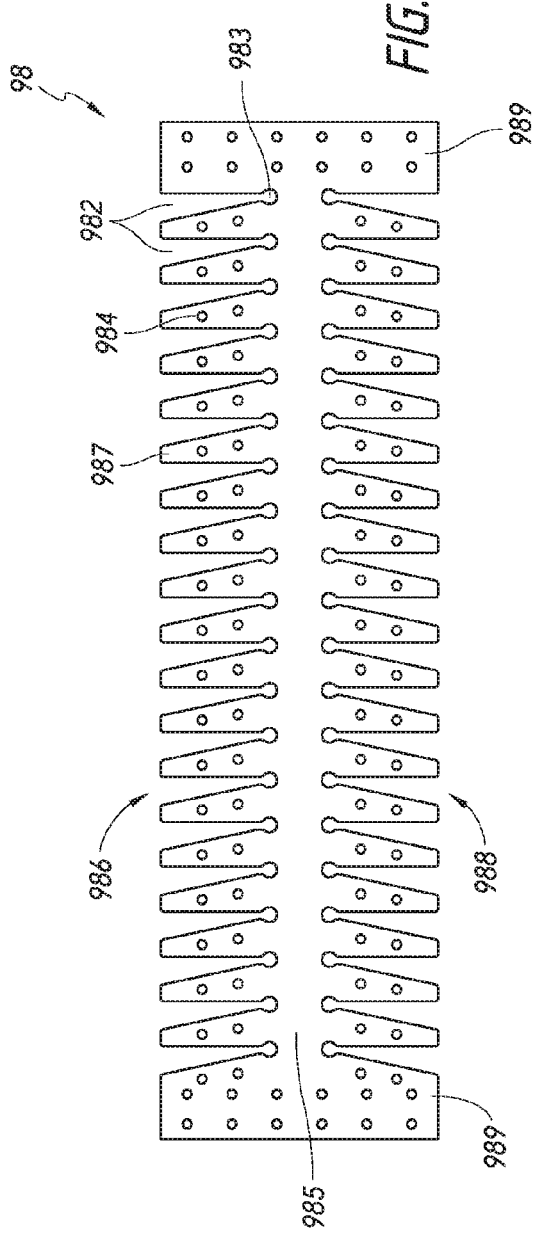
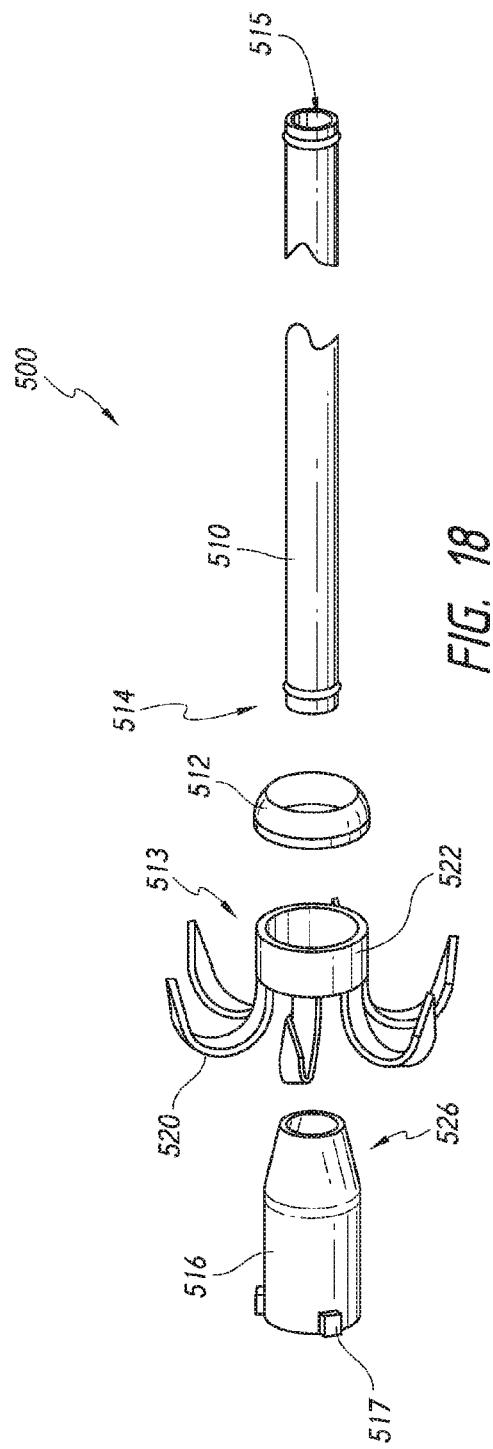

REPLACEMENT MITRAL VALVE, DELIVERY SYSTEM FOR REPLACEMENT MITRAL VALVE AND METHODS OF USE

INCORPORATION BY REFERENCE TO ANY PRIORITY APPLICATIONS

This application claims the benefit of U.S. Provisional Application No. 62/155,405, filed Apr. 30, 2015, titled "FLEXIBLE DELIVERY DEVICE AND METHODS OF USE," U.S. Provisional Application No. 62/163,932, filed May 19, 2015, titled "DELIVERY DEVICE FOR REPLACEMENT MITRAL VALVE AND METHODS OF USE," U.S. Provisional Application No. 62/210,165, filed Aug. 26, 2015, titled "DELIVERY SYSTEM FOR REPLACEMENT MITRAL VALVE AND METHODS OF USE,", and U.S. Provisional Application No. 62/300,478, filed Feb. 26, 2016, titled "REPLACEMENT MITRAL VALVE, DELIVERY SYSTEM FOR REPLACEMENT MITRAL VALVE AND METHODS OF USE," the entirety of each of which is incorporated herein by reference.

BACKGROUND

Field

Certain embodiments disclosed herein relate generally to prostheses for implantation within a lumen or body cavity and delivery systems for a prosthesis. In particular, the prostheses and delivery systems relate in some embodiments to replacement heart valves, such as replacement mitral heart valves.

Background

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of prostheses including but not limited to replacement heart valves that can be compacted for delivery and then controllably expanded for controlled placement has proven to be particularly challenging. An additional challenge relates to the ability of such prostheses to be secured relative to intralumenal tissue, e.g., tissue within any body lumen or cavity, in an atraumatic manner.

Delivering a prosthesis to a desired location in the human body, for example delivering a replacement heart valve to the mitral valve, can also be challenging. Obtaining access to perform procedures in the heart or in other anatomical locations may require delivery of devices percutaneously through tortuous vasculature or through open or semi-open surgical procedures. The ability to control the deployment of the prosthesis at the desired location can also be challenging.

SUMMARY

Embodiments of the present disclosure are directed to a prosthesis, such as but not limited to a replacement heart valve. Further embodiments are directed to methods of delivering a prosthesis into a body cavity and/or securing a prosthesis to intralumenal tissue. In some embodiments, a replacement heart valve and methods for delivering a replacement heart valve to a native heart valve, such as a mitral valve, are provided. Embodiments of different delivery systems and methods are also disclosed herein.

The present disclosure includes, but is not limited to, the following numbered embodiments.

Embodiment 1

A flexible delivery system for replacement mitral valve implantation, the delivery system comprising an outer sheath comprising a proximal segment and a distal segment, wherein the distal segment is configured to cover a replacement mitral valve, wherein the distal segment is formed from two or more layers.

Embodiment 2

The flexible delivery system of Embodiment 1, wherein the distal segment is formed from an inner layer, an outer layer, and one or more intermediate layers positioned between the inner and outer layers.

Embodiment 3

The flexible delivery system of Embodiment 2, wherein the inner layer and outer layer comprises ePTFE.

Embodiment 4

The flexible delivery system of Embodiment 2 or 3, wherein the one or more intermediate layers comprises a nitinol hypotube.

Embodiment 5

The flexible delivery system of any of Embodiments 2-4, wherein the one or more intermediate layers comprises ePTFE.

Embodiment 6

The flexible delivery system of Embodiment 2 or 3, wherein the distal segment comprises a proximal portion and a distal portion, wherein the proximal portion comprises a first intermediate layer and the distal portion comprises a second intermediate layer located distal to the first intermediate layer.

Embodiment 7

The flexible delivery system of Embodiment 6, wherein the second intermediate layer comprises a nitinol hypotube and the first intermediate layer comprises ePTFE.

Embodiment 8

The flexible delivery system of Embodiment 6, wherein the second intermediate layer comprises ePTFE and the first intermediate layer comprises a nitinol hypotube.

Embodiment 9

The flexible delivery system of any of Embodiments 6-8, wherein a gap exists between the first intermediate layer and the second intermediate layer.

Embodiment 10

A transseptal delivery system for replacement mitral valve implantation, the delivery system comprising a nose cone shaft having a proximal end and a distal end and a lumen extending therethrough, a nose cone provided on the distal end of the nose cone shaft, an inner retention shaft slideably positioned over the nose cone shaft, the inner retention shaft having a proximal end and a distal end, an inner retention ring provided on the distal end of the inner retention shaft, the inner retention ring configured to receive struts at a proximal portion of a replacement mitral valve prosthesis, a mid shaft slideably positioned over the inner retention shaft, the mid shaft having a proximal end and a distal end, an outer retention ring provided on the distal end of the mid shaft, the outer retention ring configured to be positioned over the inner retention ring to hold the proximal portion of the replacement mitral valve prosthesis within the inner retention ring, and an outer sheath assembly slideably positioned over the mid shaft and over the outer retention ring, the outer sheath assembly configured to radially restrain a distal portion of the replacement mitral valve prosthesis when the proximal portion of the replacement mitral valve prosthesis is held by the outer retention ring within the inner retention ring.

Embodiment 11

The transseptal delivery system of Embodiment 10, wherein the outer sheath assembly is configured to slide over the nose cone.

Embodiment 12

The transseptal delivery system of Embodiment 10 or 11, further comprising a replacement heart valve prosthesis, wherein the replacement heart valve prosthesis comprises struts at a proximal portion thereof received within the inner retention ring and covered by the outer retention ring, and a distal portion covered by the outer sheath assembly.

Embodiment 13

The transseptal delivery system of Embodiment 12, wherein the replacement heart valve prosthesis further comprises a plurality of proximal anchors extending distally and a plurality of distal anchors extending proximally when the prosthesis is in an expanded configuration.

Embodiment 14

The transseptal delivery system of Embodiment 13, wherein the proximal anchors extend distally when in a delivery configuration within the outer sheath assembly.

Embodiment 15

The transseptal delivery system of Embodiment 13 or 14, wherein the distal anchors extend proximally when in a delivery configuration within the outer sheath assembly.

Embodiment 16

The transseptal delivery system of Embodiment 13 or 14, wherein the distal anchors extend distally when in a delivery configuration within the outer sheath assembly.

Embodiment 17

A flexible delivery system for replacement mitral valve implantation, the delivery system comprising: an outer sheath comprising a distal segment configured to cover a replacement mitral valve, wherein the distal segment is formed from an inner polymer layer and an outer polymer layer, and wherein the distal segment further comprises a proximal section comprising a hypotube sandwiched between the inner and outer polymer layers, and a distal section comprising an intermediate polymer layer sandwiched between the inner and outer polymer layers.

Embodiment 18

The flexible delivery system of Embodiment 17, wherein the distal section has a greater diameter than the proximal section.

Embodiment 19

The flexible delivery system of Embodiment 17 or 18, wherein the inner polymer layer, the outer polymer layer, and the intermediate polymer layer comprise ePTFE.

Embodiment 20

The flexible delivery system of any of Embodiments 17-19, further comprising a polymer reinforcement in the distal section that at least partially overlaps the intermediate polymer layer.

Embodiment 21

The flexible delivery system of Embodiment 20, wherein the polymer reinforcement comprises a fluorinated ethylene propylene insert.

Embodiment 22

The flexible delivery system of any of Embodiments 17-21, wherein the inner polymer layer and the outer polymer layer comprise ePTFE with generally longitudinally extending polymer chains, and the intermediate polymer layer comprises ePTFE having generally circumferentially extending polymer chains.

Embodiment 23

The flexible delivery system of any of Embodiments 17-22, wherein the hypotube comprises a plurality of circumferentially extending cuts along a longitudinal length thereof.

Embodiment 24

The flexible delivery system of any of Embodiments 17-23, further comprising a replacement mitral valve loaded within the distal section of the distal segment, wherein the replacement mitral valve comprises ventricular anchors that apply a radially outward force to the distal section of the distal segment.

Embodiment 25

A delivery system for replacement mitral valve implantation, the delivery system comprising an outer sheath assembly configured to radially constrain a first end of a replacement mitral valve, a mid shaft comprising a longitudinally pre-compressed polymer tube located within the outer sheath assembly, the mid shaft having a tubular outer retention ring located on a distal end of the mid shaft, the outer retention ring configured to radially constrain a second end of the replacement valve, and an inner retention shaft having an inner retention member located on a distal end of the inner retention member, the inner retention member configured to releasably couple with the second end of the replacement valve, wherein the pre-compressed polymer tube is configured so that deflection of the mid shaft does not substantially change the location of the outer retention ring relative to the inner retention member.

Embodiment 26

The delivery system of Embodiment 25, wherein the pre-compressed polymer tube comprises a pre-compressed HDPE tube.

Embodiment 27

The delivery system of Embodiment 25 or 26, wherein the mid shaft provides a distal force on the outer retention ring.

Embodiment 28

The delivery system of any of Embodiments 25-27, wherein the pre-compressed polymer tube is compressed at least ¼ inch.

Embodiment 29

The delivery system of any of Embodiments 25-28, wherein the outer retention ring is configured to cover at least ¼ of the replacement mitral valve.

Embodiment 30

The delivery system of any of Embodiments 25-29, wherein the outer retention ring is at least 15 mm in length.

Embodiment 31

A delivery system, the delivery system comprising a nose cone shaft comprising a proximal end and a distal end and a lumen extending therethrough, the nose cone shaft being configured to be delivered over a guidewire to a body location, and a nose cone connected to the distal end of the nose cone shaft, wherein the nose cone comprises an elongate hollow body that is distally tapered to facilitate bending of the nose cone when the nose cone is delivered over a guidewire and comes into contact with an internal body surface.

Embodiment 32

A flexible delivery system for replacement mitral valve implantation, the delivery system comprising an outer sheath comprising a proximal segment and a distal segment, wherein the distal segment is configured to cover a replacement mitral valve, wherein the distal segment is formed from two or more layers.

Embodiment 33

The flexible delivery system of Embodiment 32, wherein the distal segment is formed from an inner layer, an outer layer, and one or more intermediate layers positioned between the inner and outer layers.

Embodiment 34

The flexible delivery system of Embodiment 33, wherein the inner layer and outer layer comprises ePTFE.

Embodiment 35

The flexible delivery system of Embodiment 33 or 34, wherein the one or more intermediate layers comprises a nitinol hypotube.

Embodiment 36

The flexible delivery system of any of Embodiments 33-35, wherein the one or more intermediate layers comprises ePTFE.

Embodiment 37

The flexible delivery system of any of Embodiments 32-33, wherein the distal segment comprises a proximal portion and a distal portion, wherein the proximal portion comprises a first intermediate layer and the distal portion comprises a second intermediate layer located distal to the first intermediate layer.

Embodiment 38

The flexible delivery system of Embodiment 37, wherein the second intermediate layer comprises a nitinol hypotube and the first intermediate layer comprises ePTFE.

Embodiment 39

The flexible delivery system of Embodiment 37, wherein the second intermediate layer comprises ePTFE and the first intermediate layer comprises a nitinol hypotube.

Embodiment 40

The flexible delivery system of any of Embodiments 37-39, wherein a gap exists between the first intermediate layer and the second intermediate layer.

Embodiment 41

A delivery system for controlled deployment of a replacement mitral valve, the delivery system comprising a nose cone shaft comprising a proximal end and a distal end and a lumen extending therethrough, a nose cone connected to the distal end of the nose cone shaft, wherein the nose cone comprises an elongate hollow body that is distally tapered, an inner retention shaft slideably positioned over the nose cone shaft, the inner retention shaft comprising a proximal end and a distal end, an inner retention member provided on the distal end of the inner retention shaft, the inner retention member configured to engage struts at a proximal portion of a replacement mitral valve prosthesis, a mid shaft slideably positioned over the inner retention shaft, the mid shaft comprising a proximal end and a distal end, wherein the mid-shaft is at least partially composed of a pre-compressed HDPE material, an outer retention member provided on the distal end of the mid shaft, the outer retention member configured to be positioned over the inner retention member to hold the proximal portion of the replacement mitral valve prosthesis in engagement with the inner retention member, and an outer sheath assembly slideably positioned over the mid shaft and within a generally-rigid live-on sheath, the outer sheath assembly configured to extend over the outer retention member, the outer sheath assembly configured to radially restrain a distal portion of the replacement mitral valve prosthesis when the proximal portion of the replacement mitral valve prosthesis is held by the outer retention member in engagement with the inner retention member, wherein a distal portion of the outer sheath assembly is formed from an inner ePTFE layer and an outer ePTFE layer, the distal portion comprising a proximal section comprising a cut nitinol tube between the inner ePTFE layer and an outer ePTFE layer, and a distal section comprising an ePTFE insert located between the inner ePTFE layer and the outer ePTFE layer, the ePTFE insert having a polymer orientation approximately perpendicular to that of the inner ePTFE layer and an outer ePTFE layer, and a fluorinated ethylene propylene strip located on a distal end of the distal section, wherein the distal section has a larger diameter than the proximal section.

Embodiment 42

A replacement mitral valve prosthesis, comprising an expandable frame having a proximal end and a distal end and a longitudinal axis extending therebetween, wherein the expandable frame comprises a plurality of foreshortening cells, a plurality of distal anchors each extending distally from a distal portion of the expandable frame and curving to extend proximally at ends of each of the plurality of distal anchors, the distal anchors being shaped and configured to extend between chordae tendineae and behind native mitral valve leaflets when the expandable frame is expanded within a native mitral valve annulus, a plurality of proximal anchors extending distally from a proximal portion of the expandable frame and curving radially outwardly away from the frame, the proximal anchors being shaped and configured to be positioned in the left atrium when the expandable frame is expanded within a native mitral valve annulus, and a plurality of locking tabs each extending proximally from a proximal portion of the expandable frame and radially inwardly toward the longitudinal axis.

Embodiment 43

The replacement mitral valve prosthesis of Embodiment 42, wherein when the frame is in an expanded configuration, the frame has a width as measured perpendicular to the longitudinal axis that is greater than a height measured parallel to the longitudinal axis.

Embodiment 44

The replacement mitral valve prosthesis of Embodiment 42 or 43, wherein the frame comprises at least two rows of foreshortening cells.

Embodiment 45

The replacement mitral valve prosthesis of any of Embodiments 42-44, wherein the frame further comprises at least one row of hexagonal-shaped cells proximal to the foreshortening cells.

Embodiment 46

The replacement mitral valve prosthesis of Embodiment 45, wherein when the frame is in an expanded configuration, the proximal anchors extend distally within hexagonal-shaped cells and then curve radially outwardly outside of the hexagonal cells.

Embodiment 47

The replacement mitral valve prosthesis of Embodiment 46, wherein when the frame is in an expanded configuration, each of the hexagonal-shaped cells has a proximal end inclined radially-inwardly toward the longitudinal axis relative to a distal end of each hexagonal-shaped cell.

Embodiment 48

The replacement mitral valve prosthesis of any of Embodiments 42-47, wherein when the frame is in an expanded configuration, the ends of the proximal anchors extend substantially perpendicular to the longitudinal axis.

Embodiment 49

The replacement mitral valve prosthesis of any of Embodiments 42-48, wherein when the frame is in an expanded configuration, the ends of the distal anchors extend substantially parallel to the longitudinal axis.

Embodiment 50

The replacement mitral valve prosthesis of Embodiment 49, wherein when the frame is in an expanded configuration, the ends of the distal anchors are positioned radially outward of the ends of the proximal anchors.

Embodiment 51

The replacement mitral valve prosthesis of any of Embodiments 42-50, wherein the plurality of proximal anchors are equally spaced circumferentially around the expandable frame, and the plurality of distal anchors are equally spaced circumferentially around the expandable frame.

Embodiment 52

The replacement mitral valve prosthesis of any of Embodiments 42-51, wherein at least one of the proximal anchors comprises an eyelet.

Embodiment 53

The replacement mitral valve prosthesis of any of Embodiments 42-52, wherein when the frame is in an expanded configuration, the hexagonal-shaped cells comprise at least a portion that is substantially longitudinally non-foreshortening.

Embodiment 54

The replacement mitral valve prosthesis of any of Embodiments 42-53, further comprising a valve body attached to the expandable frame.

Embodiment 55

The replacement mitral valve prosthesis of any of Embodiments 42-54, further comprising an annular flap surrounding an exterior of the expandable frame positioned distal to the proximal anchors, the annular flap configured to expand with blood on an atrial side of a native mitral valve annulus when the expandable frame is expanded within a native mitral valve annulus.

Embodiment 56

A replacement mitral valve prosthesis, comprising an expandable frame having a proximal end and a distal end and a longitudinal axis extending therebetween, wherein the expandable frame in an expanded configuration comprises a distal portion comprising at least one row of diamond-shaped cells, wherein the diamond-shaped cells are configured to cause the distal portion to radially expand and longitudinally foreshorten when the expandable frame is expanded, and a plurality of distal anchors each extending distally from a distalmost corner of a diamond-shaped cell, the distal anchors curving to extend proximally at ends of each of the plurality of distal anchors, and a proximal portion comprising at least one row of hexagonal-shaped cells, each of the hexagonal-shaped cells formed from a proximal row of undulating struts, a pair of vertical struts attached to two distalmost valleys of the proximal row of undulating struts, and two proximalmost struts forming the diamond-shaped cells, wherein the at least one row of hexagonal-shaped cells is configured to be circumferentially expandable when the expandable frame is expanded, a plurality of proximal anchors extending from a proximalmost corner of the hexagonal-shaped cells, each of the plurality of proximal anchors extending distally and curving radially outwardly away from the hexagonal-shaped cells, and a plurality of locking tabs each extending proximally from the proximalmost ends of the hexagonal-shaped cells, the locking tabs having enlarged proximal ends, wherein the expandable frame is configured to be collapsible to a radially compacted configuration for delivery and expandable to a radially expanded configuration for implantation.

Embodiment 57

The replacement mitral valve prosthesis of Embodiment 56, further comprising two rows of diamond-shaped cells.

Embodiment 58

The replacement mitral valve prosthesis of Embodiment 56 or 57, wherein the plurality of locking tabs are inclined when the frame is in the expanded configuration so that the enlarged proximal ends are closer to the longitudinal axis than distal ends of the plurality of locking tabs.

Embodiment 59

The replacement mitral valve prosthesis of any of Embodiments 56-58, wherein the ends of the distal anchors are parallel to the longitudinal axis.

Embodiment 60

The replacement mitral valve prosthesis of any of Embodiments 56-59, wherein the plurality of proximal anchors comprises enlarged ends.

Embodiment 61

The replacement mitral valve prosthesis of Embodiment 60, wherein the enlarged ends extend substantially perpendicular to the longitudinal axis.

Embodiment 62

The replacement mitral valve prosthesis of any of Embodiments 56-61, wherein the proximal portion comprises a single row of hexagonal-shaped cells.

Embodiment 63

The replacement mitral valve prosthesis of any of Embodiments 56-62, wherein the enlarged proximal ends of the plurality of locking tabs are generally mushroom-shaped.

Embodiment 64

The replacement mitral valve prosthesis of any of Embodiments 56-63, wherein the plurality of distal anchors first extends generally distally and radially inward, then extends distally and radially outward, and then extends proximally and parallel to the longitudinal axis.

Embodiment 65

An expandable prosthesis comprising a row of hexagonal-shaped cells, a plurality of locking tabs, each locking tab extending proximally from a proximalmost corner of the hexagonal-shaped cells, a plurality of proximal anchors, each proximal anchor extending distally from a proximalmost corner of the hexagonal-shaped cells, such that each proximalmost corner of the row of hexagonal-shaped cells comprises one proximal anchor and one locking tab, a proximal row and a distal row of diamond-shaped cells distal to the row of hexagonal-shaped cells, each diamond-shaped cell in the proximal row of diamond shaped cells sharing two struts with a hexagonal-shaped cell and two struts with a diamond shaped cell in the second row of diamond-shaped cells, and a plurality of distal anchors, each distal anchor extending distally from a distalmost corner of a diamond-shaped cell in the first row of diamond shaped cells, the plurality of distal anchors curving proximally after extending distally.

Embodiment 66

A delivery system for replacement mitral valve implantation, the delivery system comprising a mid shaft comprising a tubular outer retention ring located on a distal end of the mid shaft, the outer retention ring configured to radially constrain a portion of a replacement mitral valve, an inner retention shaft having an inner retention member located on a distal end of the inner retention member, the inner retention member configured to releasably couple with a portion of the replacement mitral valve, a spring located within the tubular outer retention ring, and a cover attached to a distal end of the spring, the cover configured to cover at least a portion of the inner retention member, wherein the spring is configured to retain the cover at least partially over the inner retention member until the outer retention ring is translated relative to the inner retention member proximally a particular distance.

Embodiment 67

A delivery system for replacement mitral valve implantation, the delivery system comprising one or more delivery components configured to deliver a replacement mitral valve to a native mitral valve, and a guide sheath having a lumen and a distal end with an open or openable wall, the distal end of the guide sheath being articulable to a plurality of shapes suitable for guiding the one or more delivery components to the native mitral valve, wherein the one or more delivery components are configured to pass through the lumen of the guide sheath and out the open or openable wall.

Embodiment 68

A guidewire assembly for replacement mitral valve implantation, the guide wire comprising a guidewire having a proximal end and a distal end, and an anchor mechanism attached or attachable to the distal end of the guide wire, the anchor mechanism comprising a tubular component having a lumen, the lumen configured to receive the distal end of the guide wire, and a plurality of hooks extending outwardly from the tubular component, wherein tips of the plurality of hooks are configured to extend distally in a compressed position and extend proximally in a released position, wherein the anchor mechanism is configured to anchor to tissue.

Embodiment 69

The guidewire assembly of Embodiment 68, further comprising a catheter configured to hold the plurality of hooks in the compressed position, wherein removing the catheter allows the plurality of hooks to translate into the released position Embodiment 70

A method of using the guidewire assembly of Embodiment 68 or 69, comprising delivering the guidewire with the anchor mechanism attached thereto through a native mitral valve into a chamber of the heart, anchoring the anchor mechanism to a wall of the heart, and advancing one or more delivery components carrying a replacement mitral valve over the guidewire to the native mitral valve.

BRIEF DESCRIPTION OF THE DRAWINGS

These and other features, aspects and advantages are described below with reference to the drawings, which are intended to illustrate but not to limit the invention.

FIGS. 5A-D illustrate a distal end of the delivery system of FIG. 1 including a spring retention cover.

FIG. 7 show components of the delivery system of FIG. 6 with the outer sheath assembly moved proximally.

FIG. 8 show components of the delivery system of FIG. 7 with the mid shaft assembly moved proximally.

FIG. 9 illustrates a schematic, cross-sectional view of an outer sheath assembly.

FIG. 10 illustrates a hypotube incorporated into the outer sheath assembly of FIG. 9.

FIG. 11 shows a hollow nose cone bending upon impact with a surface.

FIG. 17 illustrates an embodiment of a distal tip of a guide sheath in a flat view.

FIG. 18 illustrates an exploded view of an embodiment of an anchored guidewire which can be incorporated into embodiments of the delivery system.

DETAILED DESCRIPTION

The present specification and drawings provide aspects and features of the disclosure in the context of several embodiments of replacement heart valves, delivery systems and methods that are configured for use in the vasculature of a patient, such as for replacement of natural heart valves in a patient. These embodiments may be discussed in connection with replacing specific valves such as the patient's aortic or mitral valve. However, it is to be understood that the features and concepts discussed herein can be applied to products other than heart valve implants. For example, the controlled positioning, deployment, and securing features described herein can be applied to medical implants, for example other types of expandable prostheses, for use elsewhere in the body, such as within an artery, a vein, or other body cavities or locations. In addition, particular features of a valve, delivery system, etc. should not be taken as limiting, and features of any one embodiment discussed herein can be combined with features of other embodiments as desired and when appropriate. While certain of the embodiments described herein are described in connection with a transfemoral delivery approach, it should be understood that these embodiments can be used for other delivery approaches such as, for example, transapical approaches. Moreover, it should be understood that certain of the features described in connection with some embodiments can be incorporated with other embodiments, including those which are described in connection with different delivery approaches.

Delivery System

Figure 1:
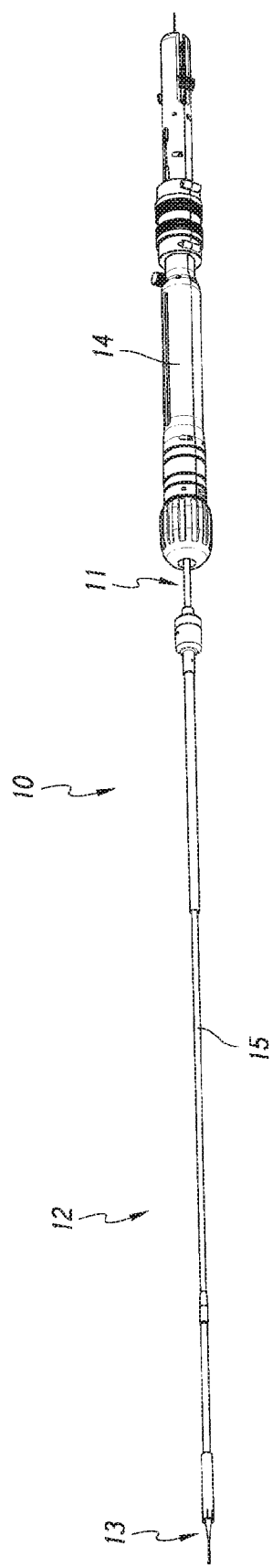
FIG. 1 shows an embodiment of a delivery system.

With reference to FIG. 1, an embodiment of a delivery system or system 10 is shown. The delivery system can be used deploy a prosthesis, such as a replacement heart valve, within the body. Replacement heart valves can be delivered to a patient's heart mitral valve annulus or other heart valve location in various ways, such as by open surgery, minimally-invasive surgery, and percutaneous or transcatheter delivery through the patient's vasculature. While the delivery system 10 is described in connection with a percutaneous delivery approach, and more specifically a transfemoral delivery approach, it should be understood that features of delivery system 10 can be applied to any other delivery system described herein, including delivery systems which are described in connection with a transapical delivery approach. Further examples of devices, systems and methods are described in U.S. Provisional Application No. 62/163,932, filed May 19, 2015, the entirety of which is incorporated by reference. In particular, delivery system 10 as described herein can have components, features, and/or functionality similar to those described with respect to delivery systems, devices and methods described in at least paragraphs [0006]-[0037] and [0078]-[0170] of U.S. Provisional Application No. 62/163,932, filed May 19, 2015, including the description relating to FIGS. 1-40B, and all of these descriptions are expressly incorporated by reference herein. Moreover, delivery system 10 as described herein can have components, features, and/or functionality similar to those described with respect to the systems, devices and methods described with respect to paragraphs [0171]-[0197] of U.S. Provisional Application No. 62/163,932, filed May 19, 2015, including the description relating to FIGS. A1-A5, B1-B6, C1-C2 and 41A-42B, and all of these descriptions are expressly incorporated by reference herein.

The delivery system 10 can be used to deploy an expandable prosthesis 70 (shown in FIG. 3), such as a replacement heart valve as described elsewhere in this specification, within the body. The delivery system 10 can receive and/or cover portions of the expandable implant or prosthesis 70 such as a first end 301 and second end 303 of the prosthesis 70. For example, the delivery system 10 may be used to deliver a prosthesis 70, where the prosthesis 70 includes a first end 301 and a second end 303, and wherein the second 303 end is configured to be deployed or expanded before the first end 303. The delivery system 10 can be relatively flexible. In some embodiments, the delivery system 10 is particularly suitable for delivering a replacement heart valve to a mitral valve location through a transseptal approach (e.g., between the right atrium and left atrium via a transseptal puncture).

Figure 2:
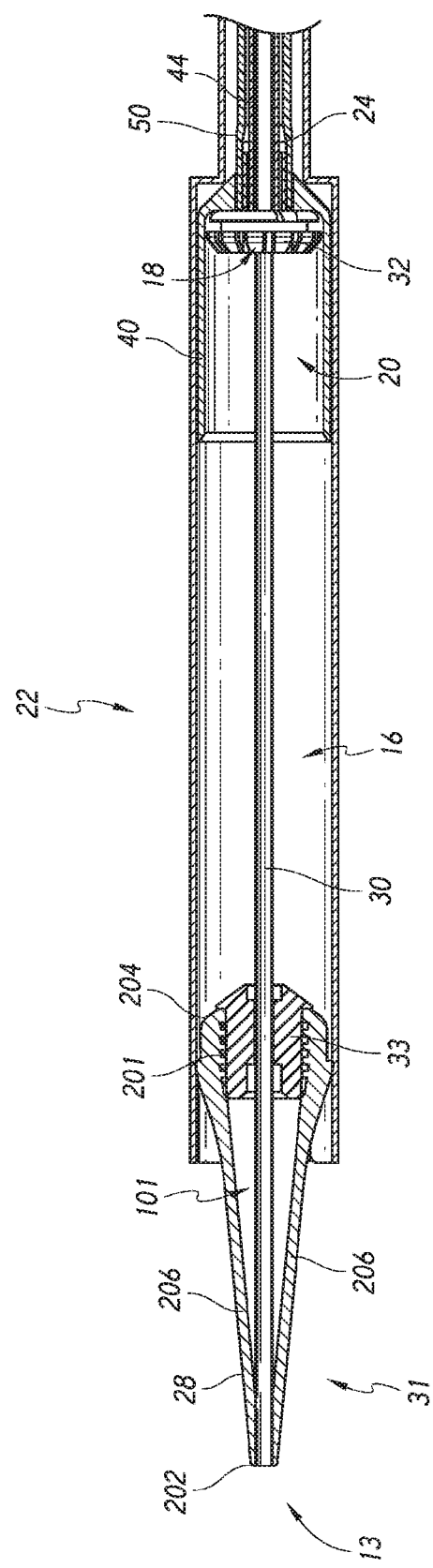
FIG. 2 shows a cross-sectional view of a distal end of the delivery system of FIG. 1.

As shown in FIGS. 1 and 2, the delivery system 10 can include an elongate shaft assembly 12 comprising a proximal end 11 and a distal end 13, wherein a handle 14 is coupled to the proximal end of the assembly 12. The elongate shaft assembly 12 can be used to hold the prosthesis 70 for advancement of the same through the vasculature to a treatment location. The elongate shaft assembly 12 can include an implant retention area 16 at its distal end shown in FIG. 2, though it could be in other locations as well, that can be used for this purpose. In some embodiments, the elongate shaft assembly 12 can hold an expandable prosthesis 70 in a compressed state at implant retention area 16 (shown in FIG. 2) for advancement of the prosthesis 70 within the body. The elongate shaft assembly 12 may then be used to allow controlled expansion of the prosthesis 70 at the treatment location. Further, the delivery system 10 can have a live-on sheath 15. The live-on sheath 15 can extend away from the handle 14 partially down a length of the proximal end 11 of the elongate shaft assembly 12. The live-on sheath 15 can be made of a relatively rigid material to provide for structural of the elongate shaft assembly 12 while preventing unwanted radial motion or bending of the elongate shaft assembly 12.

As shown in cross-sectional view of FIG. 2 without prosthesis 70, the elongate shaft assembly 12 can include one or more subassemblies such as an inner assembly 18, a mid shaft assembly 20, an outer sheath assembly 22, and nose cone assembly 31 as will be described in more detail below.

As shown, the outer sheath assembly 22 can form a radially outer covering, or sheath, to surround an implant retention area 16. Moving radially inward, the mid shaft assembly 20 can be composed of a mid shaft 50 with its distal end attached to outer retention member 40, such as an outer retention ring. Moving further inwards, the inner assembly 18 can be composed of an inner retention shaft 24 and an inner retention member 32. Further, the most radially-inward assembly is the nose cone assembly 31 which includes the nose cone shaft 30 having the distal end connected to the nose cone 28.

The elongate shaft assembly 12, and more specifically the nose cone assembly 31, inner assembly 18, mid shaft assembly 20, and outer sheath assembly 22, can be configured to deliver a prosthesis positioned within the implant retention area 16 to a treatment location. One or more of the subassemblies can then be moved to allow the prosthesis to be released at the treatment location. For example, one or more of the subassemblies may be movable with respect to one or more of the other subassemblies. The handle 14 can include various control mechanisms that can be used to control the movement of the various subassemblies as will also be described in more detail below. In this way, the prosthesis can be controllably loaded onto the delivery system 10 and then later deployed within the body.

Figure 3:
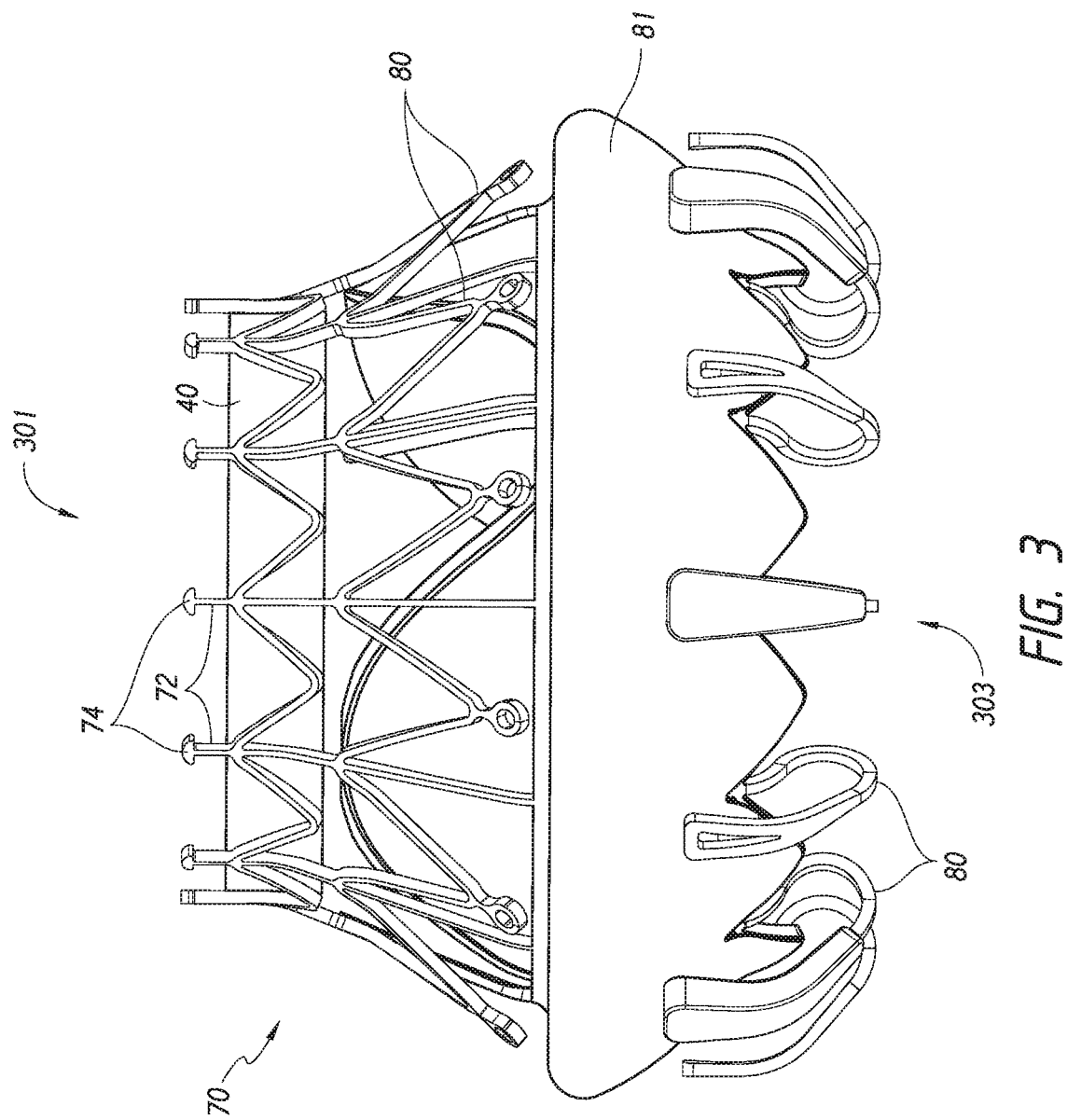
FIG. 3 shows an embodiment of a valve prosthesis that may be delivered using the delivery systems described herein.
Figure 4:
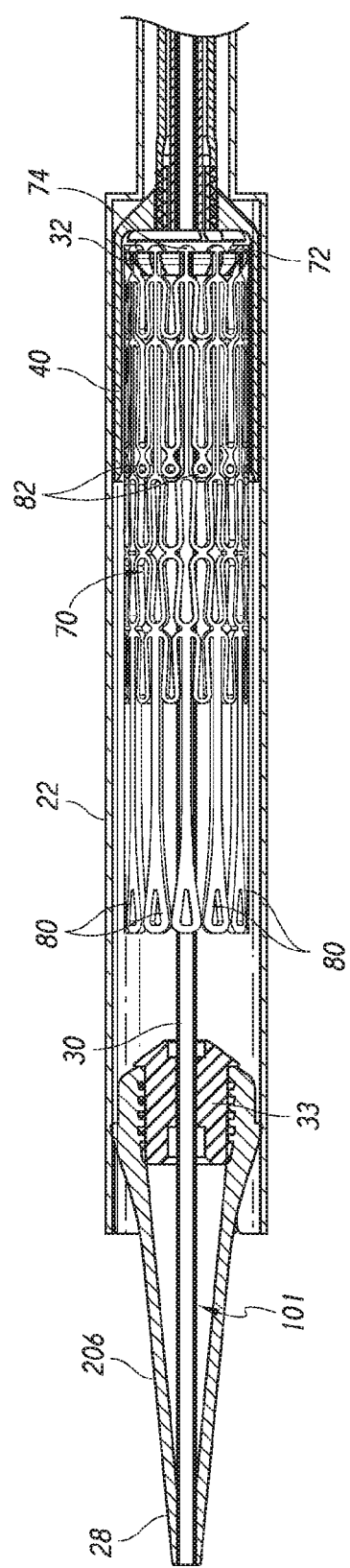
FIG. 4 shows the distal end of the delivery system of FIG. 2 loaded with the valve prosthesis of FIG. 3.

As mentioned, FIG. 2 illustrates an embodiment of the system 10 showing the subassemblies, but does not contain the prosthesis 70. FIG. 3 shows an example of the prosthesis 70 with FIG. 4 showing the prosthesis 70 inserted into the implant retention area 16. For ease of understanding, in FIG. 4, the prosthesis 70 is shown with only the bare metal frame illustrated. The implant or prosthesis 70 can take any number of different forms. A particular example of frame for a prosthesis is shown herein, though it will be understood that other designs can also be used. The prosthesis 70 can include one or more sets of anchors, such as distal (or ventricular) anchors 80 extending proximally when the prosthesis frame is in an expanded configuration and proximal (or atrial) anchors 82 extending distally when the prosthesis frame is in an expanded configuration. The prosthesis 70 can include struts 72 topped by mushroom-shaped tabs 74 on its first end 301. Further, the prosthesis 70 can include an annular flap surrounding the prosthesis 70 generally on the second end 303.

Additional details and example designs for a prosthesis are described in U.S. Pat. Nos. 8,403,983, 8,414,644, 8,652,203 and U.S. Patent Publication Nos. 2011/0313515, 2012/0215303, 2014/0277390, 2014/0277422, 2014/0277427, the entirety of these patents and publications are hereby incorporated by reference and made a part of this specification. Further details and embodiments of a replacement heart valve or prosthesis and its method of implantation are described in U.S. Patent Publication No. 2015/0328000, filed May 19, 2015, the entirety of which is hereby incorporated by reference and made a part of this specification. Further discussion on the annular flap 81 can be found in U.S. Patent Publication No. 2015/0328000, hereby incorporated by reference in its entirety.

As will be discussed below, the inner retention member 32, the outer retention member 40, the outer sheath assembly 22 as illustrated in FIG. 4 can cooperate to hold the replacement heart valve 70 in a compacted configuration. The inner retention member 32 is shown engaging struts 72 at the proximal end of the heart valve 70. For example, slots located between radially extending teeth on the inner retention member 32 can receive and engage the struts 72 which may end in mushroom-shaped tabs 74 on the proximal end of the heart valve 70. The mushroom-shaped tabs 74 can be retained within a circumferential gap/ring located proximal to the teeth. The outer retention member 40 can be positioned over the inner retention member 32 so that the proximal end of the replacement heart valve 70 is trapped therebetween, securely attaching it to the delivery system 10.

As shown in FIG. 4, the distal anchors 80 can be located in a delivered configuration where the distal anchors 80 point generally distally (as illustrated, axially away from the main body of the prosthesis frame and away from the handle 14 of the delivery system 10). The distal anchors 80 can be restrained in this delivered configuration by the outer sheath assembly 22. Accordingly, when the outer sheath 22 is withdrawn proximally, the distal anchors 80 can flip positions to a deployed configuration (e.g., pointing generally proximally). FIG. 4 also shows the proximal anchors 82 extending distally in their delivered configuration within the outer sheath assembly 22 and within the outer retention member 40. In other embodiments, the distal anchors 80 can be held to point generally proximally in the delivered configuration.

The delivery system 10 may be provided to users with a prosthesis 70 preinstalled. In other embodiments, the prosthesis 70 can be loaded onto the delivery system shortly before use, such as by a physician or nurse.

Figure 6:
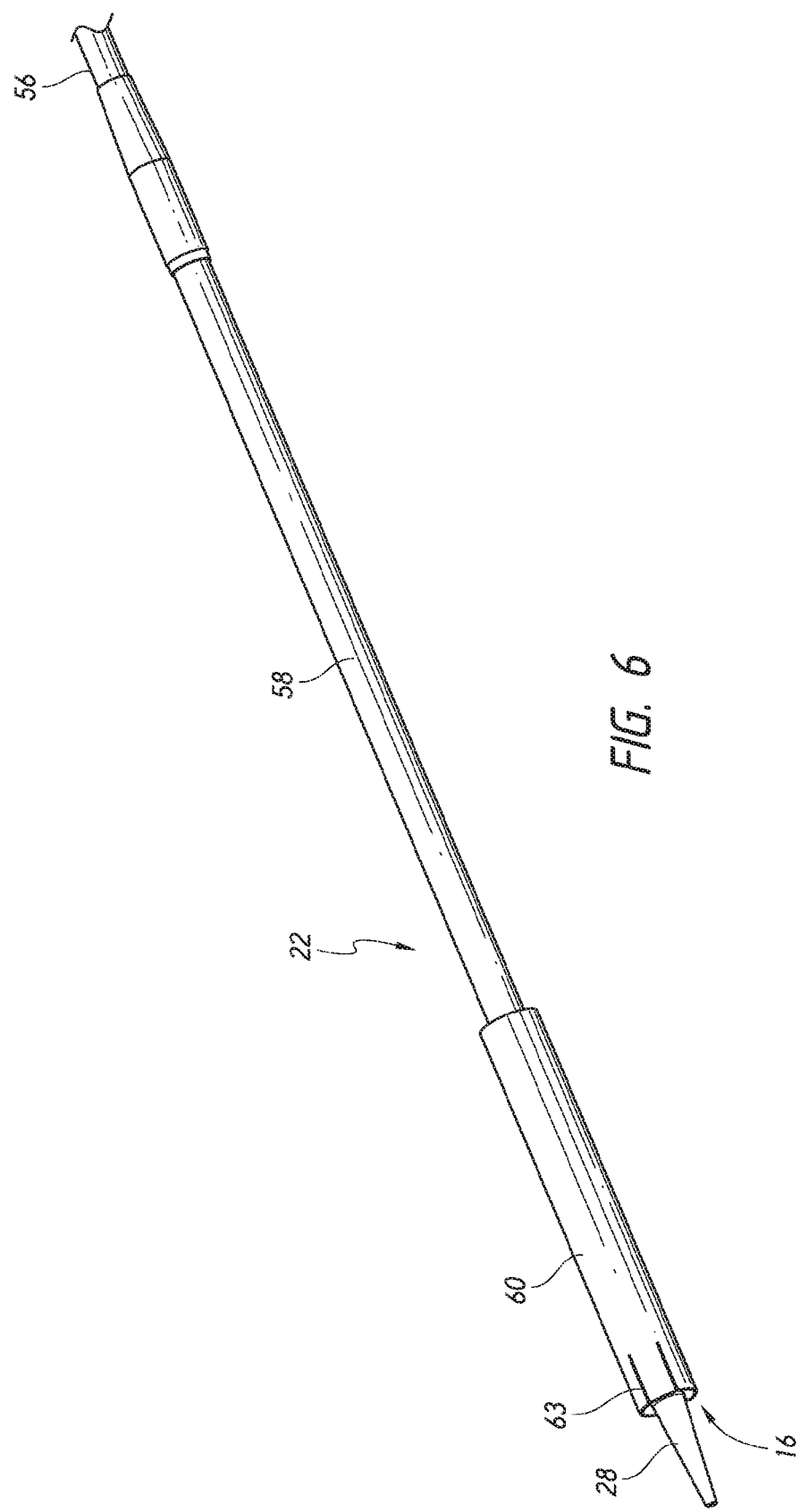
FIG. 6 shows a perspective view of the distal end of the delivery system of FIG. 1.

FIG. 6-8 illustrate further views of delivery system 10 with different assemblies moved away translated and described in detail.

The outer sheath assembly 22 will now be described, which is shown in FIG. 6. Specifically, FIG. 6 shows an outer sheath assembly 22 in its distal most position relative to nose cone 28. The outer sheath assembly 22 is disposed so as to be slidable over the inner assembly 18, the mid shaft assembly 20, and the nose cone assembly 31. Like the nose cone assembly 31, inner assembly 18 and the mid shaft assembly 20, the outer sheath assembly 22 can be a single piece tube or multiple pieces connected together to provide different characteristics along different sections of the tube. As has been mentioned, in some embodiments it can be desirable, and/or needful, for the delivery system 10 to have greater flexibility at the distal end of the device, where flexibility is not as necessary for the proximal end. The illustrated outer sheath assembly 22 has a first segment 56, a second segment 58, and a third segment 60, where the first segment 56 is proximal to the second segment 58, and the second segment 58 is proximal to the third segment 60. The third segment 60 of the outer sheath assembly 22 is shown in contact with the proximal end of the nose cone 28. In this position, the prosthesis 70 can be held within the outer shaft assembly 22 for advancement of the same through the vasculature to a treatment location.

The first segment 56 may be a tube and is preferably formed plastic, but could also be a metal hypotube or other material. In some embodiments, the tube 56 is formed of a polyether block amide (PEBA) or other type of a thermoplastic elastomer (TPE). In particular, the tube 56 can be a wire braided reinforced PEBA which can enhance pushability and trackability.

The second segment 58 can be a metal hypotube which in some embodiments may be cut or have slots. The tube 58 can be covered or encapsulated with a layer of ePTFE, PTFE, or other material so that the outer surface of the outer sheath assembly is generally smooth. The third segment 60 can be a tube formed of a plastic or metal material. In a preferred embodiment, the third segment 60 is formed of ePTFE or PTFE. In some embodiments this sheathing material can be relatively thick to prevent tearing and to help maintain a self-expanding implant in a compacted configuration. In some embodiments the material of the third segment 60 is the same material as the coating on the cut hypotube 1058. The full construction of the second segment 58 and third segment 60 are discussed in detail below with respect to FIG. 9.

In some embodiments the third segment 60 can include one or more wings or tabs 63, shown in FIG. 6, extending distally from a distal end of the third segment 60. The tabs 63 can be configured to bend, curve, or fold radially outward from the third segment 60. The one or more tabs 63 can facilitate loading of a replacement valve within the third segment 60 when the replacement valve is initially loaded into the delivery system 10. In some embodiments, the one or more tabs 63 can be removed prior to use within a patient, as shown in FIG. 11. The one or more tabs 63 can be formed by cutting the third segment 60 via methods including, but not limited to, laser cutting.

FIG. 7 illustrates the delivery system 10 with the outer sheath assembly 22 pulled back proximally, thus exposing or partially exposing the mid shaft assembly 20 including a portion of or all of a prosthesis (not shown) in the implant retention area 16. Like the nose cone assembly 31, inner assembly 18 and outer sheath assembly 22, the mid shaft assembly 20 can be a single piece tube or multiple pieces connected together to provide different characteristics along different sections of the tube. As has been mentioned, in some embodiments it can be desirable, and/or needful, for the delivery system 10 to have greater flexibility at the distal end of the device, where flexibility is not as necessary for the proximal end. The illustrated mid shaft assembly 20 has a first segment (not shown) near handle 14, a second segment or mid shaft 50 distal to the first segment, and a third segment 40 distal the mid-shaft 50 being the outer retention member 40. The first segment can extend distally away from the handle 14 and be connected to the second segment or mid shaft 50 at the distal end of the first segment. As shown in FIG. 7, the distal end of the second segment 50 can attach to the outer retention member 40 (e.g., third segment). Each of the segments can be a tube, for example a metal or polymer tube, such as described with respect to the outer sheath assembly 22.

Through the use of the handle, the mid shaft assembly 20 can translate or slide over the inner assembly 18, which thereby causes the outer retention member 40 to slide over the inner assembly 18 and encircle the inner retention member 32 described below. As shown in FIG. 4, the outer retention member 40 encircles a portion of the prosthesis 70, in particular the first end 301, thus preventing the prosthesis 70 from expanding. Further, the mid shaft assembly 20 can be translated proximally with regards to the inner assembly 18 into the outer sheath assembly 22, thus exposing a first end 301 of the prosthesis 70 held within the outer retention member 40. A taper 61 may be provided at the proximal end of the outer retention member 40 to allow it to more easily slide into the outer sheath assembly 22, specifically the third segment 60. In this way the outer retention member 40 can be used to help secure a prosthesis 70 to or release it from the delivery system 10. While not shown, the mid shaft assembly 20 can include an outer retention member lock that may be used to connect the outer retention member 40 to the mid shaft 50. This lock can be located directly proximal to the outer retention member 40 and can be attached to both the mid shaft 50 and the outer retention member 40, thus keeping the outer retention member 40 in the correct position on the mid shaft 50. The lock can be located radially inside the outer retention member 40. The lock can, for example, be a generally tubular piece having a threaded surface that can thread with the outer retention member 40. However, other attachment mechanisms between the lock and the outer retention member 40, such as complementary shaped pieces or adhesives, can be used as well. The outer retention member 40 can have a cylindrical or elongate tubular shape, and may sometimes be referred to as an outer retention ring.

The mid shaft 50 itself can be made of, for example, high density polyethylene (HDPE), as well as other appropriate materials as described herein. The mid shaft 50 can be formed of a longitudinally pre-compressed HDPE tube, which can provide certain benefits. For example, the pre-compressed HDPE tube can apply a force distally onto the outer retention member 40, thus preventing accidental, inadvertent, and/or premature release of the prosthesis 70. Specifically, the distal force by the mid shaft 50 keeps the distal end of the outer retention member 40 distal to the inner retention member 32, thus preventing the outer retention member 40 from moving proximal to the inner retention member 32 before it is desired by a user to release the prosthesis 70. This can remain true even when the delivery system 10 is being bent at a sharp angle. Further, the pre-compressed HDPE tube allows the delivery system 10 to remain flexible in order to bend to a particular section, while still applying a distally directed force on the outer retention member 40. The pre-compressed HDPE tube can be reduced a length of about 1/8, 1/6, 1/4, 1/2, or 1 inches from its natural state to form the pre-compressed HDPE tube. In other embodiments, the mid shaft 50 can comprise a spring to hold the outer retention member 40 in place.

In some embodiments, a spring can be used to cover the prosthesis 70 to prevent accidental, inadvertent, and/or premature release of the prosthesis 70. The spring can be used in conjunction to the pre-compressed HDPE tube described above, or as a replacement of such a tube. An embodiment of the spring retention section is shown with respect to FIGS. 5A-D.

Figure 5A:
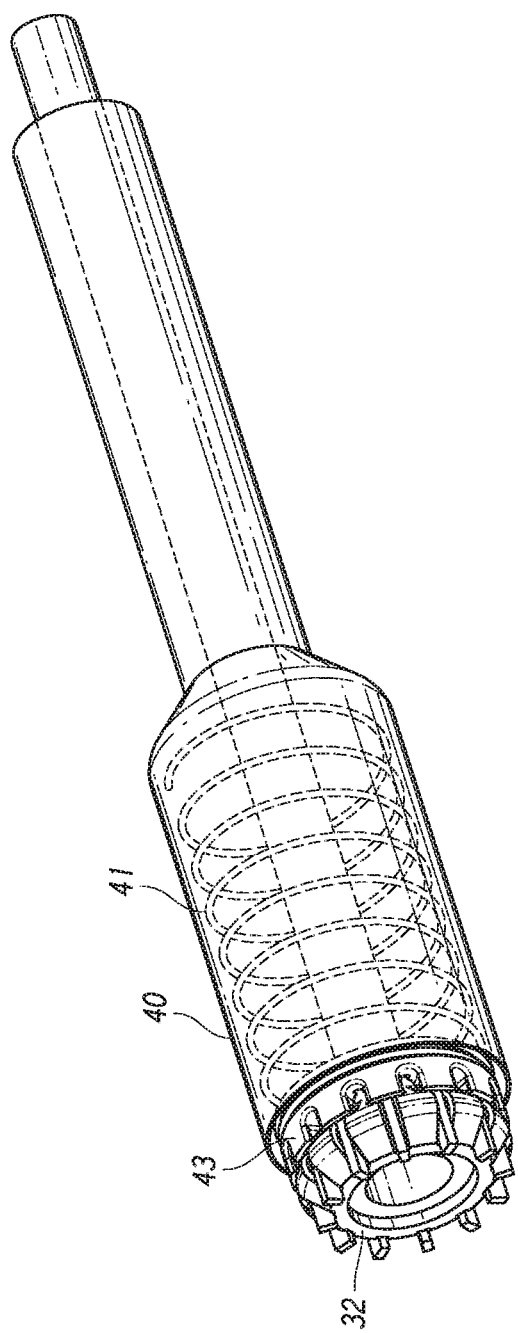

As shown in FIG. 5A, the spring 41 can be attached to an inner surface/diameter of the outer retention member 40 and can include a disc or cup-shaped cover 43 on its distal end. In some embodiments, the spring 41 can be attached to the proximal inner surface of the outer retention member 40. In the uncompressed/relaxed position (shown in FIG. 5D), the spring 41 may extend to the distal end (or farther) of the outer retention member 40. The spring 41 can be configured to curl around the inner surface of the outer retention member 40.

In some embodiments, the spring 41 can be designed such that the spring length in the relaxed position is greater than or equal to the length of the outer retention member 40. In some embodiments, the spring length in the relaxed position can be greater than or equal to 1 mm, 2 mm, 3 mm, 4 mm, or 5 mm longer than the length of the outer retention member 40 for safety, though the particular excess length greater than the length of the outer retention member 40 is not limiting.

As mentioned, a cover 43 can be attached to a distal end of the spring 41. The cover 43 can be generally cylindrical, and shaped in a similar manner as the outer retention member 40. In some embodiments, the cover 43 can be ring shaped, donut shaped, etc. In particular, the cover 43 can be sized and configured to at least partially cover the inner retention member 32. Accordingly, the cover 43 can have an outer diameter greater than the outer diameter of the inner retention member 32. Further, the cover 43 can contain a lumen for the inner retention shaft 24 to pass through. In some embodiments, the cover 43 can abut a proximal surface of the inner retention member 32 on a distal surface of the cover 43.

The cover 43 can act as a secondary temporary outer retention member 40 in case the outer retention member 40 is prematurely withdrawn proximally, thereby exposing the inner retention member 32, in particular the slots in the inner retention member 32. Specifically, when the inner retention member 32 moves forward or juggles, such as because of slop or bending of the delivery system 10, the cover 43 attached to the spring 41 can remain forward to cover the inner retention member 32, preventing inadvertent release of the prosthesis 70. Thus, if the outer retention member 40 is accidentally pulled back over the inner retention member 32, the cover 43 still remains over the inner retention member 32 preventing accidental release. It is only on the application of further proximal force to the outer retention member 40 that would uncover the inner retention member 32, thus allowing release of the prosthesis 70.

FIG. 5B shows a view of the spring 41 within the outer retention member 40 in the loaded configuration. At this point, the spring 41 is compressed and is configured to expand distally upon release, which allows the cover 43 to remain over the inner retention member 32. In some embodiments, the spring 41 can also provide a distal force on the inner retention member 32.

FIG. 5C shows a view where the outer retention member 40 is withdrawn backwards due to pending or slop. If this were to occur without the spring 41 and cover 43, the inner retention member 32 would be uncovered, thus causing release of the prosthesis 70. However, as shown, the cover 43 is still maintained over the inner retention member 32, thus preventing release of the prosthesis.

Figure 5D:
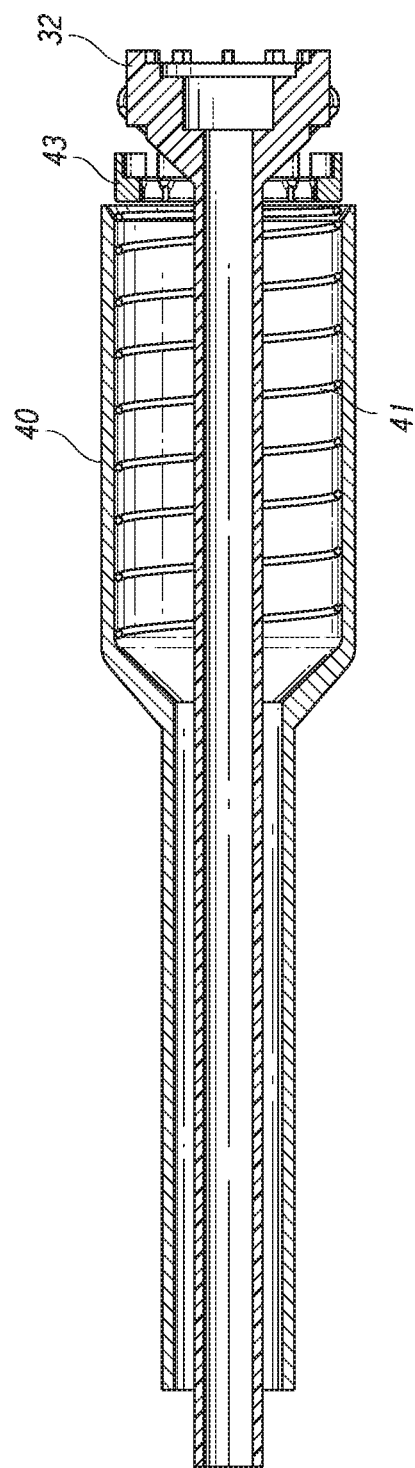

FIG. 5D shows the outer retention member 40 pulled even farther back from the previous position. At this point, the spring 41 is in a fully relaxed/uncompressed position/length and is in its expanded condition. Thus, the spring will now translate along with the outer retention member 40. As shown in the figure, as the outer retention member 40 is now drawn back proximally, the inner retention member 32 is uncovered, thus allowing the prosthesis 70 to be released.

Further, in some embodiments, as shown in FIG. 4, the outer retention member 40 can cover a substantial length of the prosthesis 70 which can help avoid accidental release of the prosthesis 70. The long outer retention member 40 can be used in conjunction with the spring 41 and/or pre-compressed HDPE tube, all of which can be used to prevent inadvertent release. For example, the outer retention member 40 can cover over ⅛, ¼, ⅓, or ½ of the prosthesis 70. In addition, the outer retention member 40 can cover a substantial length of the atrial anchors 82. For example, the outer retention member 40 can cover over 75%, over 80%, over 85%, or over 90% of the atrial anchors 82. The outer retention member 40 can be about 15, 16, 17, 18, 19, or 20 mm in length or a range between those lengths. In some embodiments, the outer retention member 40 can be between about 10 and about 30 mm in length.

FIG. 8 shows approximately the same view as FIG. 7, but with the mid shaft assembly 20, including the outer retention member 40 and mid shaft 50, retracted proximally, thereby exposing the inner assembly 18 (including the inner retention member 32 attached to inner retention shaft 42) and nose cone assembly 31 (including the nose cone shaft 30 attached to the nose cone 28).

As mentioned the inner assembly 18 can be composed of the inner retention shaft 42 with the inner retention member 32 attached to the distal end of the inner retention shaft 42. Similar to the assemblies above, the inner retention shaft 42 can comprise a tube, such as a hypodermic tube or hypotube (not shown). The tube can be made from one of any number of different materials including nitinol, stainless steel, and medical grade plastics. The tube can be a single piece tube or multiple pieces connected together. Using a tube made of multiple pieces can allow the tube to provide different characteristics along different sections of the tube, such as rigidity and flexibility.

In some embodiments a first segment (not shown) of the inner assembly 18 can be made of a hypotube can extend along a majority of the length of the inner assembly 18. For example, metal hypotube extends from within the handle 14 at the proximal end towards the distal end up until a second segment of the inner assembly 18 before the implant retention area 16. The hypotube can provide column strength (pushability) to the inner assembly. A second segment 42 of the inner assembly 18 can be made of a more flexible material. For example, the second segment 42 can comprise a wire such as a multi-stranded wire, wire rope, or wire coil. The wire can surround a more flexible tube, such as a plastic tube, or it may be formed as a tube without any additional inner materials or core. Thus, in some embodiments, the wire can be a hollow core wire rope. The wire can provide the inner assembly 18 with strength, but it can also provide more flexibility to allow for navigating the curvosities of the vasculature, such as within the heart.

The inner assembly 18 can also include a prosthesis retention mechanism such as an inner retention member 32 at a distal end of the second segment 42 that can be used to engage with the prosthesis, as discussed with respect to FIG. 4. For example, the inner retention member 32 may comprise an inner retention ring that includes a plurality of slots configured to engage with struts 72 on the prosthesis 70. The inner retention member 32 can also be considered to be part of the implant retention area 16, and may be at the proximal end of the implant retention area 16. With struts 72 or other parts of a prosthesis 70 engaged with the inner retention member 32, the outer retention member 40 can cover both the prosthesis 70 and the inner retention member 32 to secure the prosthesis on the delivery system 10 (shown in FIG. 4).

Further, as shown in FIG. 8, the nose cone assembly 31 may comprise an elongate member, and in some embodiments, may have a nose cone 28 on the distal end of a nose cone shaft 30. The nose cone 28 can be made of Pebax or polyurethane for atraumatic entry and to minimize injury to venous vasculature. The nose cone 28 can also be radiopaque to provide for visibility under fluoroscopy.

The nose cone shaft 30 may include a lumen sized and configured to slidably accommodate a guidewire so that the delivery system 10 can be advanced over the guidewire through the vasculature. The nose cone shaft 30 may be connected from the nose cone 28 to the handle, or may be formed of different segments such as the other assemblies. Further, the nose cone shaft 30 can be formed of different materials, such as plastic or metal, similar to those described in detail above.

This view also illustrates that the nose cone shaft 36 can be slidably disposed within the inner assembly 18, thus allowing the nose cone shaft 28 (and thus nose cone 28) and the inner retention member 32 to move separately from one another during deployment and use.

The inner and outer retention rings and the delivery system generally may be similar to those disclosed in U.S. Pat. Nos. 8,414,644 and 8,652,203, the entire contents of both of which are hereby incorporated by reference herein and made a part of this specification. This is inclusive of the entire disclosure, including other apparatuses and methods described therein, and is not in any way limited to the disclosure of the inner and outer retentions and/or the delivery system.

Outer Sheath Assembly Construction

As shown in the illustrated embodiments of FIG. 2, the outer sheath assembly 22 can include a lumen extending therethrough to allow the sheath assembly 22 to be moveable or slideable relative to components contained therein. As shown in more detail in FIG. 9, the outer sheath assembly 22 can include a third segment 60 and a second segment 58, the second segment 58 being proximal to the third segment 60. The third segment 60 may be larger in inner diameter and outer diameter than the second segment 58, and may be sized in length and inner diameter to receive a prosthesis 70 as described herein in a collapsed configuration. These two segments can each have a different diameter, thereby forming the stepped configuration shown in FIG. 9.

It should be noted that the second segment 58, relative to the overall length of the delivery system 10, is still generally positioned at a distal portion of the delivery system 10 while the delivery system 10 is being used to deliver the replacement valve towards the in situ implantation site. Moreover, the outer sheath assembly 22 may include other segments positioned proximal of the second segment 58. Such segments may, for example, couple the second segment 58 to a handle of the delivery system 10. The third segment 60 can be positioned radially outward from a prosthesis 70 when the delivery system 10 is in an initial, delivery configuration such that the prosthesis 70 is maintained in the delivery system 10 in an undeployed configuration.

The outer sheath assembly 22 can include a lumen running therethrough to allow the sheath assembly 22 to be moveable or slideable relative to components contained therein. The walls forming the third segment 60 and/or the walls forming the second segment 58 can be formed from one or more materials, such as PTFE, ePTFE, PEBAX, ULTEM, PEEK, urethane, nitinol, stainless steel, and/or any other biocompatible material. Preferably, the third segment 60 is formed from one or more materials which allow the third segment 60 to be compliant and flexible while still maintaining a sufficient degree of radial strength to maintain a replacement valve within the third segment 60 without substantial radial deformation which could increase friction between the third segment 60 and a replacement valve contained therein, sufficient column strength to resist buckling of the third segment 60, and sufficient tear resistance to reduce the likelihood that the prosthesis 70 causes the third segment 60 to tear. Flexibility of the third segment 60 can be advantageous, particularly for a transseptal approach. For example, while being retracted along a curved member, the third segment 60 can follow the curved member without applying significant forces upon the curved member which may cause the curved member to decrease in radius. Rather, the third segment 60 can bend and/or kink as it is being retracted along such a curved member such that the radius of the curved member is maintained. Lack of flexibility in the third segment 60 can cause the distal portion of the delivery system 10 to straighten as the third segment 60 is retracted along the curved member. This straightening could cause the third segment 60 of the delivery system 10 to move thereby placing the third segment 60 in misalignment relative to the in situ implantation site, thereby also moving and placing the prosthesis 70 contained in the third segment 60 of the delivery system 10 in misalignment relative to the in situ implantation site.

In some embodiments, the wall of the third segment 60 and/or the wall of the second segment 58 can be formed as a composite with one or more layers. In some embodiments, the construction of the walls in the different segments can be different. This can advantageously provide different structural characteristics for both the third and second segments 60, 58. In some embodiments, the construction of the walls in the different segments can be the same. As shown in the illustrated embodiment of FIG. 9, the wall can include an inner layer 82 and an outer layer 84. The inner layer 82 and/or the outer layer 84 can both be formed from ePTFE. The two layers can be two discrete layers bonded together, or can be a single layer that comprises the same material with intermediate layers, discussed below, sandwiched within. One or more additional layers can be positioned between the inner layer 82 and/or the outer layer 84 to further modify the structural characteristics of the wall. For example, the wall can include a first intermediate layer (e.g., ePTFE insert 160), a second intermediate layer (e.g., hypotube 150) and a third intermediate layer (e.g., fluorinated ethylene propylene tube 164). This can advantageously allow the outer sheath assembly 22 to have structural characteristics which differ throughout the length of the assembly 22. Moreover, the layered structure described herein can allow the outer sheath assembly 22 to be compliant and flexible while still maintaining a sufficient degree of radial strength, column strength, and tear resistance. Examples of the intermediate layers are disclosed below.

As shown in the embodiment in FIG. 10 showing a flat pattern of the hypotube 150, a hypotube 150 can have a plurality of spaced slots 152 extending along the length from a distal end 156 to a proximal end 154 of the hypotube 150 with the slots increasing in width towards the distal end 156. In this manner, the flexibility of the hypotube 150 can be greater near the distal end 156 of the hypotube 150 as compared to the proximal end 154. In some embodiments, this can be reversed such that the slots increase in width from the distal end 156 towards the proximal end 154. In such an embodiment, the flexibility of the hypotube 150 can be greater near the proximal end 154 of the hypotube 150 as compared to the distal end 156. In some embodiments, the hypotube 150 can be designed such that a portion between the distal and proximal ends 156, 154 can have a greater degree of flexibility or a lesser degree of flexibility than the distal and proximal ends 156, 154. The hypotube 150 can be embedded within any desired portion of the outer sheath assembly 22, such as within the second segment 58, the third segment 60, or both. For example, as shown in FIG. 9, a hypotube 150 may be embedded into an ePTFE layer or layers forming the second segment 58 of the outer sheath assembly 22.

The hypotube 150 can provide structural rigidity, while the cuts can provide for flexibility in the hypotube. For example, they hypotube 150 can be a laser cut nitinol tube designed to allow adequate flexibility but with sufficient column strength to provide finite control for stepwise retraction of the outer sheath during deployment. The remaining material can form a series of interconnected "H"s that are offset by 90 degrees. As another example, the hypotube 150 can be cut into a series of rings with small connecting members extending between the rings. For example, two equally spaced connecting members can be used to connect two rings and the subsequent connecting members can be offset 90 degrees. Other numbers of connecting members such as one, two, three, four, etc. can also be used.

Further, an ePTFE insert 160 can be incorporated as an intermediate layer as well. The ePTFE insert 160 can have a generally tube like shape or can be formed as a partial tube. The ePTFE insert 160 can be located in a section away from the nitinol hypotube 150. For example, as shown in FIG. 9, if the nitinol hypotube 150 is in the second segment 58, the ePTFE insert 160 can be in the third segment 60, though this positioning can be reversed.

The ePTFE insert 160 can be formed of the same material as the inner layer 82 and outer layer 84 (e.g., ePTFE). However, the ePTFE insert 160 can be formed so that it has a polymer chain alignment approximately perpendicular to that of the inner and outer layers 82/84. For example, if the polymer chains of the inner and outer layers 82/84 are aligned distally-to-proximally, the polymer chains of the ePTFE insert 160 can be aligned radially. This will allow the outer sheath assembly 22 to have both tensile and compressive strength, while still allowing the outer sheath assembly 22 to remain flexible. In some embodiments, the ePTFE insert 160 can have polymer chains that have different orientation throughout. The ePTFE insert 160 can have a different thickness from the inner/outer layers 82/84 as well. For example, as shown in the illustrated embodiment, the ePTFE insert 160 can be thicker than the ePTFE of the inner layer 82 and outer layer 84 of the wall. However, other materials and configurations of the insert can be used.

Further, the third segment 60 can additionally include a reinforcement material, such as fluorinated ethylene propylene (FEP) tube 164 between inner and outer layers 82/84 as an intermediate layer, as shown in FIG. 9. As shown in FIG. 9, the FEP tube 164 can be on top of the ePTFE insert 160 or hypotube 150, whichever is located in the third segment 60. Further, the FEP tube 164 can be adjacent to or spaced apart from the ePTFE insert 160 or hypotube 150, whichever is located in the third segment 60. The FEP tube 164 can overlap the ePTFE insert 160 as well. The FEP tube 164 can be more rigid than the ePTFE insert 160, and thus can provide for more structural support at the distal end of the third segment 60. For example, the FEP tube 164 can provide for strength against the movement of the distal anchors 80 which press outwards against the outer sheath assembly 22 in the retracted position. The FEP tube 164 can be located at the far distal end of the third segment 60 or can be spaced away from the distal end of the third segment 60.

It is contemplated that the intermediate layers can be spaced apart longitudinally such that a gap exists between the intermediate layers or the intermediate layers can be positioned adjacent one another. A spaced apart configuration is shown in FIG. 9 which includes a hypotube 150 spaced apart from an ePTFE insert 160. This can be advantageous if the inner and outer layers 82/84 provide sufficient structural characteristics, such as radial strength, column strength, and tear resistance along certain portions of the third segment 60 and further flexibility is desired in such portions. For example, in some embodiments, the ePTFE insert 160 can be positioned along a portion of the third segment 60 which is subject to more stresses, such as axial, radial, and/or hoop stresses, due to components and structures contained within the third segment 60. In embodiments where a prosthesis 70 is positioned within the third segment 60, the ePTFE insert 160 and/or FEP tube 164 can be positioned along portions where the prosthesis 70 exerts greater amounts of force upon the third segment 60. For example, with respect to prosthesis 70, the ePTFE insert 160 and/or FEP tube 164 can be positioned along a portion of the third segment 60 which covers the distal anchors 80 or other portions which extend significantly radially outward relative to other portions of the prosthesis 70 as shown in FIG. 9. The portions of the wall which do not have an intermediate layer can serve as bending or kinking points for the outer sheath assembly 22. In some embodiments, the inner layer 82 and the outer layer 84 can be in contact within such gaps. In some embodiments, a gap can be maintained between the inner layer 82 and the outer layer 84.

Other types of materials and structures are also contemplated for the intermediate layers, including the FEP tube 164 and ePTFE insert 160, including, but not limited to, FEP, ePTFE, PTFE, PEBAX, ULTEM, PEEK, urethane, stainless steel, and other biocompatible materials. In some embodiments, the material may serve as a marker to assist the user in properly positioning the delivery system 10 at an in situ implantation location. For example, the material can be radiopaque. Moreover, these materials can be formed as fibers, wires, rings, wraps, braided structures, coils, springs, ribs, laser cut structures, and the like. In some embodiments, such as those utilizing fibers, wires and/or wraps, the direction of the fibers, wires and/or wraps can be advantageously chosen to obtain desirable structural characteristics along certain directions without compromising desirable structural characteristics along other directions. It is also contemplated that fewer or greater numbers of intermediate layers, can be used. For example, in some embodiments, there can be no intermediate layers, one intermediate layer, two intermediate layers, three, intermediate layers, or more. In some embodiments, there can be one or more additional layers between the intermediate layer and the inner and/or outer layers 82/84.

The above intermediate layers can advantageously allow the outer sheath assembly 22 to have structural characteristics which differ throughout the length of the assembly 22. Moreover, the layered structure described herein can allow the outer sheath assembly 22 be compliant and flexible while still maintaining a sufficient degree of radial strength, column strength, and tear resistance.

In some embodiments, the outer sheath assembly 22 can include one or more additional layers applied to an inner surface of the inner layer 82 and/or an outer surface of the outer layer 84. For example, additional layers can be positioned on an inner surface of the inner layer 82. These additional layers can provide additional reinforcement to specific portions of the outer sheath assembly 22, such as those which may be subject to a greater amount of stress due structural features of the replacement valve contained therein.

As noted above, fewer or greater numbers of intermediate layers can be used. One or more of these intermediate layers can be positioned in a spaced relationship similar to intermediate layers. It is contemplated that the wall can include one or more ring structures as intermediate layers with these one or more ring structures spaced apart from each other, thereby providing sufficient structural characteristics throughout the outer sheath assembly 22 while also maintaining a significant amount of flexibility.

The different layers described herein can be attached via mechanical fasteners, such as screws, rivets, sutures and any other type of mechanical fastener as desired, chemical fasteners such as adhesives and any other type of chemical fastener as desired, fastening techniques such as sintering, welding, and any other type of fastening technique as desired, and/or a combination of such fasteners and techniques. For example, in some embodiments, the layers can be sintered together.

The structural characteristics of the wall of the outer assembly can be further modified after the wall is formed with the layers described herein. For example, the wall can incorporate one or more cutouts, such as holes or slots, disposed along the wall. Such cutouts can be advantageously positioned in areas where further flexibility is desired and/or where the wall is subject to lesser degrees of stresses. In this manner, specific portions of the wall can be designed to bend and/or kink due to increased flexibility along these regions. Other types of structural features can be formed along the wall, including, but not limited to, ribs. These structural features, such as holes, slots, and ribs, can be formed by a variety of methods including laser cutting, etching, machining, and the like.

Nose Cone Construction

With reference back to the embodiment of FIG. 2, the nose cone 28 can have a generally tapered distal end. The nose cone 28 can have an elongated shape. The nose cone 28 can have a length, measured from the distalmost end to a proximalmost end, of between approximately 5 mm to 50 mm, between approximately 10 mm to approximately 40 mm, between approximately 15 mm to approximately 25 mm, approximately 20 mm, any other lengths within these ranges, and any other lengths as desired.

With reference particularly to the embodiment of FIG. 2, the outer diameter of the nose cone 28 at its proximal end can be similar to, or equal to, the inner diameter of an outer sheath assembly 22. As shown in the illustrated embodiment of FIG. 2, the nose cone 28 has an outer diameter which is similar to the inner diameter of the outer sheath assembly 22. This can form a generally smooth transition in diameter between the nose cone 28 and the outer shaft and/or the outer component if and when the nose cone 28 is brought into contact with the outer shaft and/or the outer component. In some embodiments, the nose cone 28 can have an outer diameter of approximately 30, Fr, 31 Fr or 32 Fr and the outer sheath assembly 22 can have an inner diameter of approximately 30 Fr, 31 Fr or 32 Fr.

Moreover, as shown in FIG. 2, the nose cone 28 can be generally hollow, e.g., having a cavity 101 through a portion of the nose cone 28. The cavity 101 can extend from a distal tip 202 of the nose cone 28 to the proximal portion 204 of the nose cone 28. As shown, the cavity 101 can expand in diameter along with the nose cone 28 in a distal-to-proximal direction thus keeping the walls 206 of the nose cone 28 at approximately the same thickness throughout the nose cone 28. In some embodiments, a nose cone insert 33 can be used to keep the walls 206 of the nose cone 28 open at its proximal end 204. The nose cone insert 33 can be connected to the nose cone shaft 30 or can be slidable on the shaft 30. Further, the nose cone 28 can be formed from a lower durometer material such as urethane, PEBAX, polysilicone and any other biocompatible material as desired. In some embodiments, the nose cone 28 can include threading 201 for attachment to a threaded portion of the nose cone shaft 30. In some embodiments, the nose cone 28 can be a single unit formed from a single material.

The hollow and flexible nose cone 28 can provide significant advantages while passing through the vasculature of a patient, especially in the transfemoral approach. Specifically, the blood vessels that the system 10 passes through will not necessarily be straight, and thus it can be advantageous for the system 10 to follow the blood vessels without any undue damage or catching. As shown in FIG. 11, the cavity 101 within the nose cone 28 can allow the nose cone to easily kink/bend/deflect/deform 103 when the nose cone 28 comes in contact with a bodily surface, such as the inner diameter of a blood vessel 100. This bend 103 can allow the nose cone 28 to bend and follow along a surface of the blood vessel 100 without doing any damage to the blood vessel 100.

Accordingly, as the nose cone 28 follows guidewire 105 through blood vessels in the body, the hollow nose cone 28 will bend 103 in order to continue following the blood vessel. This can advantageously reduce damage to the blood vessel 100 while still maintaining control of the device 10 so that it does not get caught.

Delivery Method

Methods of use of the delivery system in connection with a replacement mitral valve will now be described. In particular, the delivery system 10 can be used in a method for percutaneous delivery of the replacement mitral valve to treat patients with moderate to severe mitral regurgitation. The below methods are just a few examples of the how the delivery system may be used. It will be understood that the delivery systems described herein can be used as part of other methods as well.

Figure 12:
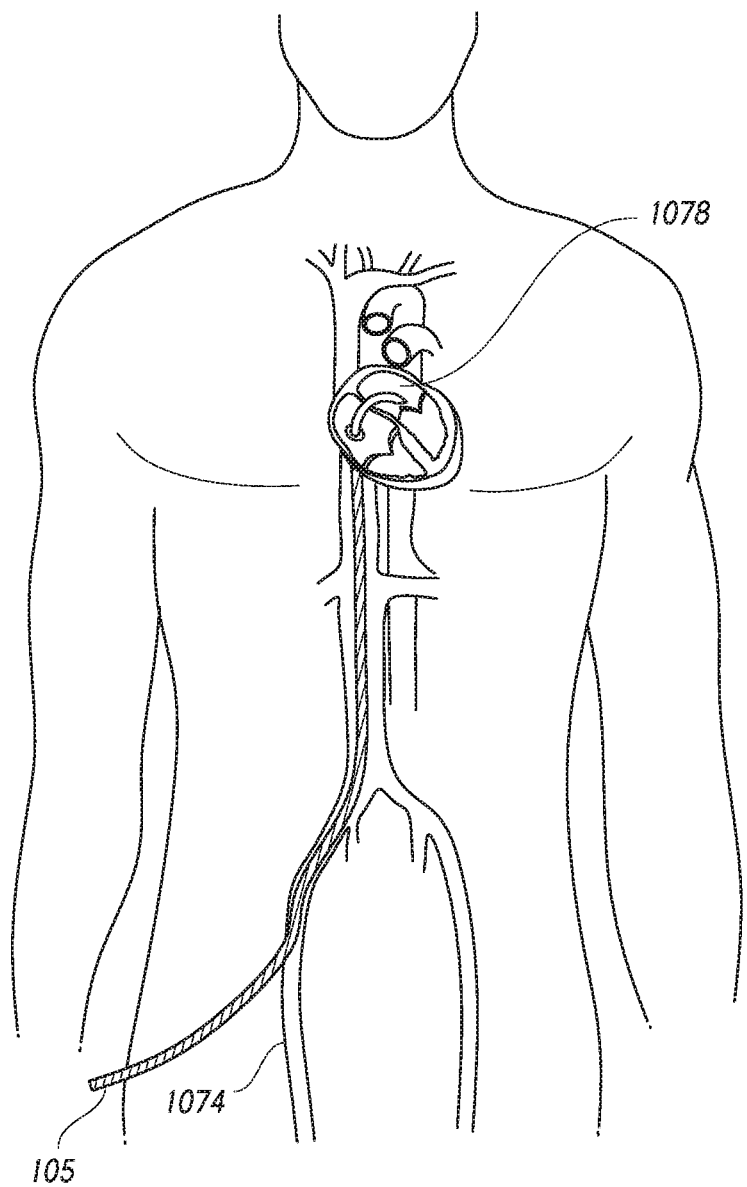
FIG. 12 illustrates a schematic representation of a transfemoral delivery approach.

As shown in FIG. 12, in one embodiment a guidewire 105 can be placed in the ipsilateral femoral vein 1074 and advanced to the right atrium. A transseptal puncture using known techniques can then be performed to obtain access to the left atrium. The guidewire 105 can then be advanced in to the left atrium and then to the left ventricle. FIG. 12 shows a guidewire 105 extending from the ipsilateral femoral vein 1074 to the left atrium 1078. A guidewire snare can be placed in the descending aorta through the ipsilateral femoral artery. The guidewire 105 can be advanced into the ascending aorta and then the snare can be used to snare the guidewire 105. The guidewire snare can then be withdrawn to externalize the guidewire from the ipsilateral femoral artery. The physician now has access to both ends of the guidewire. It will be understood that one or more introducer sheaths, catheters and/or guidewires may need to be used to get a guidewire externalized at both the ipsilateral femoral vein and the ipsilateral femoral artery. In addition, the initial guidewire 105 discussed above may not be the same as the ultimate externalized guidewire. As will be explained in more detail below, having an externalized guidewire can be useful for positioning the delivery system, especially the distal end of the delivery system, and for helping the delivery system turn some corners. Some embodiments may not use an externalized guidewire. For example, a steerable catheter may be used instead of the externalized guidewire.

With the guidewire 105 in place, the delivery system 10 can be advanced over the guidewire. The delivery system 10 can then be advanced to the right atrium, through the septal puncture and the left atrium 1078 and into the left ventricle. A steering snare may be used to help advance and position the delivery system correctly. In addition, tension can be applied to one end of the externalized guidewire to help advance and position the delivery system. Further, the nose cone 28 can be hollow, as described above, allowing the nose cone 28 to follow along the curving path of the body. This can be particularly useful to get the delivery system 10 to make the bend from extending up into the right atrium and then extending down into the left ventricle.

The construction and flexibility of the delivery system 10 can allow it to make the relatively sharp turns described above, in particular the turns from entering the right atrium to the septum and then from the septum to the mitral valve. It should be understood that the bending experienced by the delivery system 10 especially between the right atrium and the mitral valve are relatively complex and are generally not in a single plane. This part of the delivery system 10 may experience bending between 110-180 degrees and typically between 130-160 degrees, of course this is dependent on the actual anatomy of the patient.

Specifically, a method of operating the delivery system 10 and releasing an intralumenal frame assembly, such as prosthetic 70, to intralumenal tissue at an in situ target location is disclosed. The steps of this method can be carried out while the intralumenal frame assembly is in a radially compacted state within an outer member, such as outer sheath assembly 22. In some embodiments, the longitudinal axis of the frame assembly, which runs between the first and second ends of the intralumenal frame assembly, can be parallel to and/or concentric with the longitudinal axis of one or more shafts of the delivery system 10. The steps of this method can be used to transeptally deliver a replacement heart valve to a mitral valve location.

A proximal segment of the delivery system 10 can be flexible such that it can be manipulated into a curved configuration via forces exerted upon the proximal segment. For example, the proximal segment can be manipulated into a curved configuration as the proximal segment travels over a curved guidewire. In this manner, the third segment 60 can be oriented in a direction different from that of second 58 or third 60 segments. This can advantageously allow delivery of a replacement valve to an in situ implantation site, such as a native mitral valve, via a wider variety of approaches, such as a transseptal approach.

The delivery system 10 can be in a preliminary configuration with the outer sheath assembly 22 covering the prosthesis 70. In this configuration, the delivery system 10 has a relatively compact form factor which facilitates delivery of the implant to the in situ target location. As mentioned, the outer sheath assembly 22 extends through a transseptal puncture towards the native mitral valve. In order to properly orient the distal segment relative to the native mitral valve, the proximal segment is manipulated into a curved or rounded configuration. Accordingly, the outer sheath assembly 22 can form a curved or rounded configuration thereby allowing the distal portion of the delivery system 10 to remain in proper position relative to the native mitral valve. The delivery system 10 can retract the outer sheath assembly 22 such that the entirety of the prosthesis 70 is exposed. Portions of the prosthesis remain attached to the delivery system 70 via mechanisms similar to inner retention member 32 and outer retention member 40 described in connection with delivery system 10.

Though the entire elongate shaft assembly 12 may be experiencing some bending or flex, typically it is predominantly the second segments 42, 50, and 58 of the subassemblies that will be experiencing most of the bending. This can be both when making the turns as the delivery system is being advanced, and also when the prosthesis is being positioned at the mitral valve. The nose cone 28 can also be flexible and may be bent during turning and at various other times during the procedure, such as described above with respect to FIG. 11.

The second segments of the assemblies can have a bendable length that is substantially aligned with one another. The second segments may each have a bendable length of at least between about 3.5 to 4 inches (8.9 to 10.2 cm). In some embodiments, the second segment 58 of the outer sheath assembly 22 can have a bendable length of about 3⅝ inches (9.2 cm), the second segment 50 of the mid shaft assembly 20 can have a bendable length of about 4¾ inches (12.1 cm), and the second segment 42 of the inner assembly 18 can have a bendable length of about 5.5 to 6 inches (14 to 15.2 cm). In some embodiments, the relative bendable lengths of the second segments can increase going from the outermost subassembly to the innermost subassembly of the elongate shaft assembly 12.

The delivery system 10 can include a radially-compacted replacement mitral valve (e.g., prosthesis 70) that has been preloaded within the implant retention area 16. With the distal end of the delivery system 10 within the left ventricle, the operator can begin to deploy the prosthesis 70. Throughout the procedure, the prosthesis 70 can be allowed to expand partially or in full. Using one or more of the delivery system 10, the guidewire 105, and a snare, the distal end of the delivery system 10 can be positioned to be substantially perpendicular to the plane of the mitral annulus. It can also be positioned so that the tips of the distal anchors 80 on the prosthesis 70 are midway between a plane formed by the top of the mitral annulus 106 and a plane formed by the tops of the papillaries 110. The chordae tendineae 110 extend between the native leaflets 108 attached to the mitral annulus 106 and the papillaries 110. The implanted prosthesis, and structures of the heart 83, are shown with respect to FIG. 13 and discussed below.

In some embodiments, a handle 14 can control all or part of the expansion of the prosthesis 70. The user can then begin rotating a retraction knob to retract the outer sheath assembly 22 until the distal anchors 80 begin to extend out from the outer sheath assembly 22. Retracting the outer sheath assembly 22 can allow the valve to self-expand. In other embodiments, such as described below, retraction of the outer sheath assembly 22 can cause the distal anchors 80 to flip from a delivery orientation where they extend distally to a deployed orientation where they extend proximally. In some embodiments, the outer sheath assembly 22 can be at least partially retracted. The distal anchors 80 can then be positioned between the chordae tendineae 110. The angle and depth of the distal anchors 80 then be adjusted to engage one or more leaflet 108 of the mitral valve. Thus, the distal anchors 80 can be move back towards the annulus 106 and in some embodiments may engage the leaflet 108 and/or the ventricular side of the annulus 106. At the same time, the first end 301 of the prosthesis 70 can remain retained by the delivery system 10 in an at least partially radially compacted state. This can allow the position of the prosthesis 70 to still be readily adjusted.

In some embodiments, the distal anchors 80 can be positioned first at one side of the left ventricle to engage the chordae tendineae 110 and one valve leaflet 108 before engaging the other side and the other leaflet 108. As the mitral valve is a bicuspid valve, the delivery system 10 can be used to attach the distal anchors 80 first to the posterior leaflet and then to anterior leaflet. This second part can be done after the prosthesis 70 is expanded or further expanded by further retracting the outer sheath assembly 22.

In some embodiments, the entrance route of the delivery system 10 into the left atrium can bias the delivery system 10 towards one side of the mitral valve. For example, the delivery system 10 may be biased towards the posterior leaflet of the mitral valve. This can facilitate securing the distal anchors 80 to the posterior side or the posterior leaflet first, prior to expanding or further expanding the replacement heart valve 70. The distal anchors 80 can then be secured to the anterior side of the mitral valve or to the anterior leaflet.

After the distal anchors 80 are released, the delivery system 10 and prosthesis 70 can be moved proximally, which in some embodiments, causes the distal anchors 80 to engage the native leaflets 108 and/or native valve annulus 106. In addition to physically moving the delivery system, this may also be done by pushing the guidewire 105 from the venous side towards the mitral annulus 106. Once the distal anchors 80 are properly placed, the delivery system 10 can then release the proximal anchors 82 and the proximal end of the prosthesis 70. This can allow further self-expansion of the prosthesis 70 so that the proximal anchors 82 engage the upstream or atrial side of the native annulus, and the prosthesis 70 is deployed in operational condition. This can be by fully retracting the outer sheath assembly 22, such as by rotating the control knob, until the prosthesis 70 has reached its fully expanded state. However, the proximal anchors 82 do not necessarily engage the native annulus 106, and may be positioned above the annulus 106 or engage the wall of the atrium 102.

While the delivery system 10 as described above involves retraction of an outer sheath assembly 22 to uncover and deploy a prosthesis 70 contained therein, in some embodiments the delivery system 10 can deploy a prosthesis 70 with little to no proximal retraction of the outer sheath assembly 22. For example, components of the outer sheath assembly 22 can be designed to separate, as discussed below, to allow for deployment of the prosthesis 70.

For example, in some embodiments, the third segment 60 of the outer sheath assembly 22 can incorporate one or more breakaway stitches to allow the third segment 60 to separate. Breakage of the breakaway stitch can be controlled by the user of the delivery system 10. For example, the handle 14 of the delivery system 10 can include an actuator which is coupled to a component which causes the stitch to break. In some embodiments, breakage can be keyed to specific activity related to use of the delivery system 10. For example, the breakaway stich can be designed to break after the outer sheath assembly 22 has been partially retracted relative to a replacement valve contained therein. This could, for example, be caused by changes in stresses along the distal segment as the distal segment is moved relative to the replacement valve. Other portions of the delivery system 10 can include similar structures and/or mechanisms.

In some embodiments, the third segment 60 of the outer sheath assembly 22 can be peeled away to uncover the replacement valve (e.g., prosthesis 70) contained therein. For example, the one or more tabs of the distal segment can be pulled proximally while the remaining portions of the distal segment is maintained in position. This can cause the third segment 60 to separate and expose the replacement valve contained therein. The one or more tabs can be attached to an actuator of the handle via one or more tethers, wires or sutures to allow the user to pull the tabs and control separation of the distal segment. Other portions of the delivery system 10 can include similar structures and/or mechanisms.

It will be understood that in some embodiments the prosthesis 70 may not be self expanding, and the partial and full deployment may be accomplished by one or more inflatable balloons or the like. In addition, one of more inflatable balloons may be a part of the delivery system, such as part of the inner assembly 18 and can positioned at the implant retention area 16 as part of the third segment 36.

Control mechanisms and components at the handle can be used to move different portions of the device 10. To move the outer sheath assembly 22 between the advanced position and the retracted position, a control mechanism is actuated, such as a retraction knob that is rotated. This causes a lead screw connected to the outer sheath assembly 22 to move proximally. Then, to move the mid shaft assembly 20, the control mechanism is pulled backwards. Springs can be used to give feedback to the user and to better control the movement of the mid shaft assembly 20 to thereby provide a controlled release of the prosthesis. In addition, the pre-compressed mid shaft 50 can maintain a continuous extension force between the inner assembly 18 and the mid shaft assembly 20 to keep the inner retention member 32 bottomed out inside the outer retention member 40 so that the distal tip of the delivery system 10 maintains maximum flexibility and freedom of motion and the prosthesis does not unlock and prematurely deploy.

The handle 14 can also include any number of luers that can allow all subassemblies to be perfused with saline. The perfusion of saline can eliminate or reduce air embolism risk due to catheter use and can also provide flushing capability for the delivery procedure.

Figure 13:
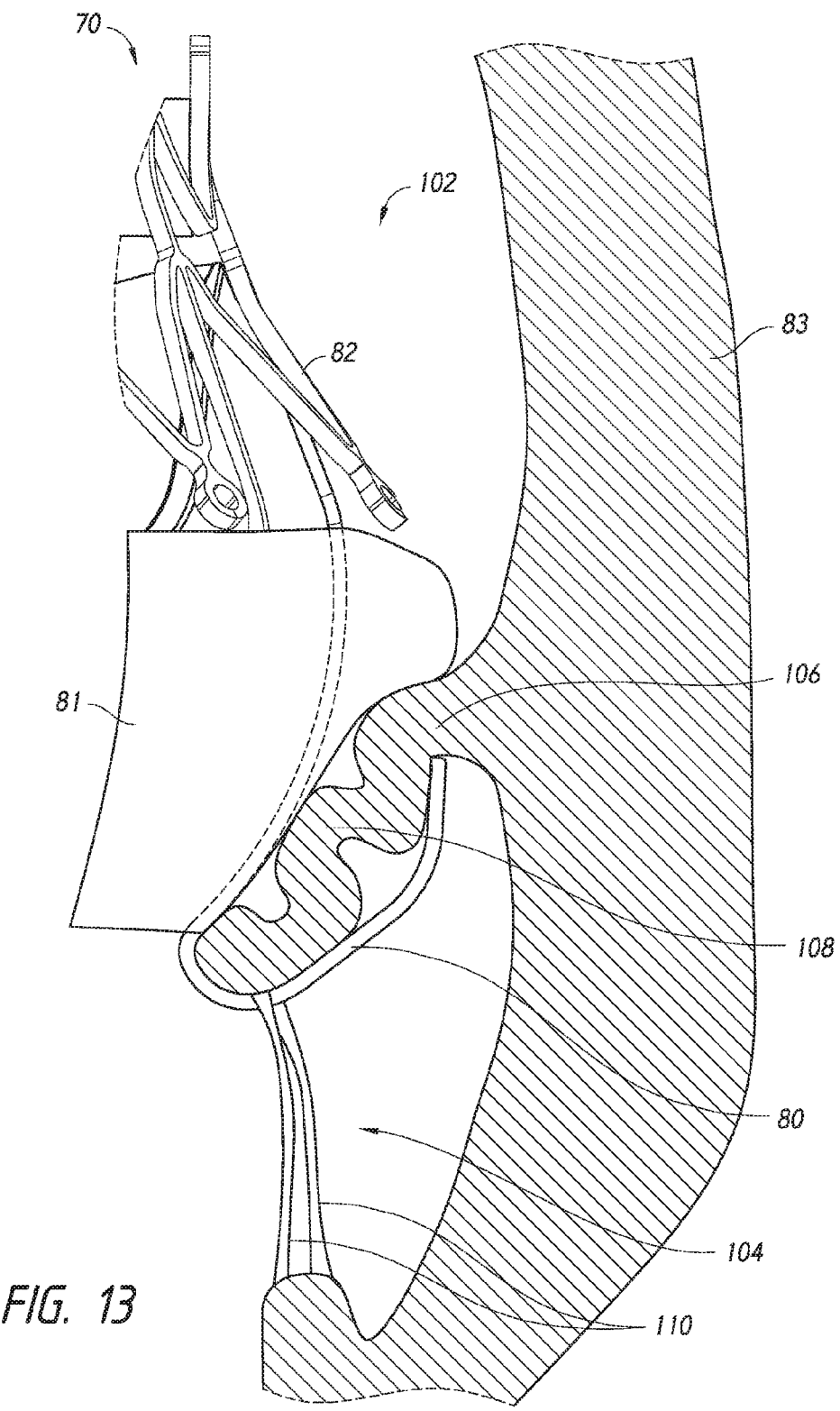
FIG. 13 illustrates a schematic representation of a valve prosthesis positioned within a native mitral valve.

Reference is now made to FIG. 13 which illustrates a schematic representation of an embodiment of a replacement heart valve (prosthesis 70) positioned within a native mitral valve of a heart 83. Further details regarding how the prosthesis 70 may be positioned at the native mitral valve are described in U.S. patent application Ser. No. 14/716,507, filed May 19, 2015, the entirety of which is hereby incorporated by reference, including but not limited to FIGS. 13A-15 and paragraphs [0036]-[0045]. A portion of the native mitral valve is shown schematically and represents typical anatomy, including a left atrium 102 positioned above an annulus 106 and a left ventricle 104 positioned below the annulus 106. The left atrium 102 and left ventricle 104 communicate with one another through a mitral annulus 106. Also shown schematically in FIG. 13 is a native mitral leaflet 108 having chordae tendineae 110 that connect a downstream end of the mitral leaflet 108 to the papillary muscle of the left ventricle 104. The portion of the prosthesis 70 disposed upstream of the annulus 106 (toward the left atrium) can be referred to as being positioned supra-annularly. The portion generally within the annulus 106 is referred to as positioned intra-annularly. The portion downstream of the annulus 106 is referred to as being positioned sub-annularly (toward the left ventricle).

As shown in the situation illustrated in FIG. 13, the replacement heart valve (e.g., prosthesis 70) can be disposed so that the mitral annulus 106 is between the distal anchors 80 and the proximal anchors 82. In some situations, the prosthesis 70 can be positioned such that ends or tips of the distal anchors 80 contact the annulus 106 as shown, for example, in FIG. 13. In some situations, the prosthesis 10 can be positioned such that ends or tips of the distal anchors 80 do not contact the annulus 106. In some situations, the prosthesis 70 can be positioned such that the distal anchors 80 do not extend around the leaflet 108. Further, the prosthesis 70 can be at least partially surrounded by an annular flap 81 between the distal anchors 82 and the proximal anchors 82. This flap 81 can wrap around the frame of the prosthesis 70 and help position the prosthesis 70 in the desired position in the body.

As illustrated in FIG. 13, the replacement heart valve 70 can be positioned so that the ends or tips of the distal anchors 80 are on a ventricular side of the mitral annulus 106 and the ends or tips of the proximal anchors 82 are on an atrial side of the mitral annulus 106. The distal anchors 80 can be positioned such that the ends or tips of the distal anchors 80 are on a ventricular side of the native leaflets beyond a location where chordae tendineae 110 connect to free ends of the native leaflets. The distal anchors 80 may extend between at least some of the chordae tendineae 110 and, in some situations such as those shown in FIG. 13, can contact or engage a ventricular side of the annulus 106. It is also contemplated that in some situations, the distal anchors 80 may not contact the annulus 106, though the distal anchors 80 may still contact the native leaflet 108. In some situations, the distal anchors 80 can contact tissue of the left ventricle 104 beyond the annulus 106 and/or a ventricular side of the leaflets.

During delivery, the distal anchors 80 (along with the frame) can be moved toward the ventricular side of the annulus 106 with the distal anchors 80 extending between at least some of the chordae tendineae 110 to provide tension on the chordae tendineae 110. The degree of tension provided on the chordae tendineae 110 can differ. For example, little to no tension may be present in the chordae tendineae 110 where the leaflet 108 is shorter than or similar in size to the distal anchors 80. A greater degree of tension may be present in the chordae tendineae 110 where the leaflet 108 is longer than the distal anchors 80 and, as such, takes on a compacted form and is pulled proximally. An even greater degree of tension may be present in the chordae tendineae 110 where the leaflets 108 are even longer relative to the distal anchors 80. The leaflet 108 can be sufficiently long such that the distal anchors 80 do not contact the annulus 106.

The proximal anchors 82 can be positioned such that the ends or tips of the proximal anchors 82 are adjacent the atrial side of the annulus 106 and/or tissue of the left atrium 102 beyond the annulus 106. In some situations, some or all of the proximal anchors 82 may only occasionally contact or engage atrial side of the annulus 106 and/or tissue of the left atrium 102 beyond the annulus 106. For example, as illustrated in FIG. 13, the proximal anchors 82 may be spaced from the atrial side of the annulus 106 and/or tissue of the left atrium 102 beyond the annulus 106. The proximal anchors 82 could provide axial stability for the prosthesis 10. In some situations, some or all of the proximal anchors 82 may not contact an annular flap 81. This may occur when the annular flap 81 is in a collapsed configuration although it may also occur when the annular flap 81 is in an expanded configuration. In some situations, some or all of the proximal anchors 82 may contact the annular flap 81. This may occur when the annular flap 81 is in an expanded configuration although it may also occur when the annular flap 81 is in a collapsed configuration. It is also contemplated that some or all of the proximal anchors 82 may contact the atrial side of the annulus 106 and/or tissue of the left atrium 102 beyond the annulus 106

The annular flap 81 can be positioned such that a proximal portion of the annular flap 81 is positioned along or adjacent an atrial side of the annulus 106. The proximal portion can be positioned between the atrial side of the annulus 106 and the proximal anchors 82. The proximal portion can extend radially outward such that the annular flap 81 is positioned along or adjacent tissue of the left atrium 102 beyond the annulus 106. The annular flap 81 can create a seal over the atrial side of the annulus 106 when the flap 81 is in the expanded state.

Guide Sheath

Figure 14:
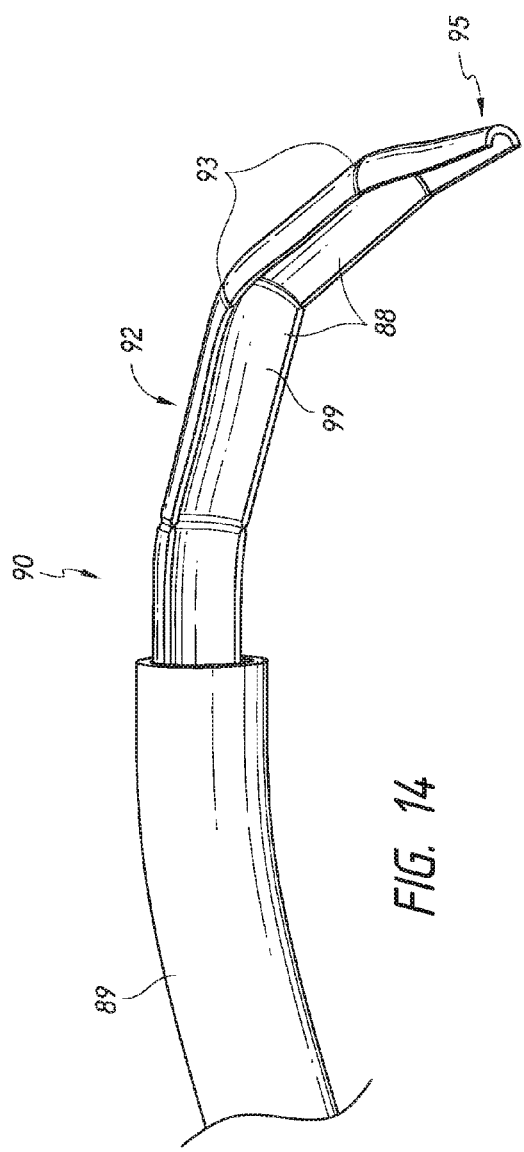
FIG. 14 illustrates a schematic representation of a distal end of an embodiment of the delivery system utilizing a guide sheath.

In some embodiments, a guide sheath can be used in conjunction with the delivery system 10 disclosed herein, such as shown in FIG. 1, to deliver a prosthesis 70 into the heart of a patient. FIG. 14 illustrates a schematic representation of an embodiment of such a guide sheath 90.

In particular, the guide sheath 90 can be configured to at least partially cover the distal end of the delivery system 10 during insertion of the delivery system 10 into the patient and prevent the delivery system 10 from injuring tissue during its insertion. Thus, in some embodiments the guide sheath 90 can be inserted into the proper location, such as by following a guide wire discussed above, and then the delivery system 10 can pass through the lumen of the guide sheath 90 and out or along a distal end of the guide sheath 90.

As shown in FIG. 14, in some embodiments the guide sheath 90 can comprise a modified distal tip. The guide sheath 90 may be formed of a thin tube, e.g. similar to a catheter, and can include a tube portion 89 proximal to a distal tip 92. In some embodiments, the tube portion 89 of the guide sheath 90 can comprise 80% to 95% of a length of the guide sheath 90. The distal tip 92 can be attached to the end of the tube portion 89, or can be integrally formed with the tube portion 89.

The guide sheath 90 can be formed of a plastic or metal material, and the particular material is not limiting. The distal tip 92 can be formed of the same or different material than the tube portion 89. In some embodiments, the distal tip 92 can be semi-rigid. The distal tip 92 may be pre-shaped to match the desired anatomy, and/or it may be articulable into a plurality of different shapes and adapt to anatomical structures. Further, in some embodiments an inner wall of the distal tip 92 can also be covered or encapsulated with a layer 99 of ePTFE, PTFE, or other material so that an inner surface of the distal tip 92 is generally smooth. The smooth PTFE inner lining 99 of the distal tip 92 can reduce friction when the delivery system 10 is advanced along the distal tip 92. In some embodiments, the layer 99 can be incorporated into the lumen of the tube portion 89.

As shown in FIG. 14, unlike the tube portion 89 of the guide sheath 90 which is fully enclosed, the distal tip 92 of the guide sheath 90 can have an open or openable wall/window/section/opening which directs the delivery system 10, and/or an expanding prosthesis 70, to the desired location. For example, if the tube portion 89 is positioned within a transseptal puncture, the distal tip 92 with open or openable wall may extend to the native mitral valve to provide a bearing surface for the delivery system and/or prosthesis to track along toward the native mitral valve.

Figure 15:
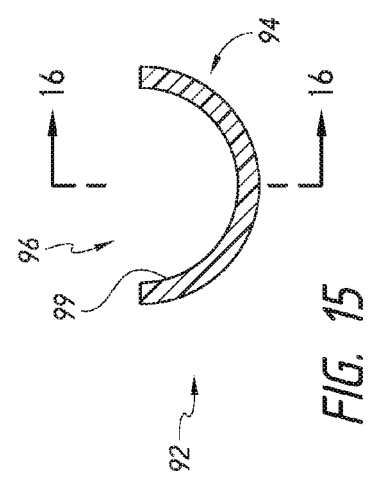
FIG. 15 illustrates an isolated cross-sectional view of a distal end of the guide sheath of FIG. 14.

FIG. 15 illustrates a cross-section of the distal tip 92 further illustrating the open wall. As shown, the distal tip 92 may not be a closed circle along at least a portion of the distal tip 92. For example, the cross section of the distal tip 92 can have a partial circle segment 94, e.g. a half-circle shape, with an open segment 96 (e.g., the open or openable wall/window/section/opening). However, the distal tip 92 may be more or less than a half-circle (such as ¼ circle or ¾ circle), and the particular circumferential distance is not limiting. The partial circle segment 94 can be rigid or semi-rigid. In some embodiments, the open or openable segment 96 of the distal tip 92 is located along the inner curvature of the distal tip 92. However, the open or openable segment may face other directions as well. In other embodiments, the distal tip 92 may have overlapping sections that open up as a device passes through the distal tip.

In some embodiments, the partial circle segment 94 can flatten (or unfold) to form an arc with a larger diameter than a diameter of the full circle cross-section of the guide sheath 90. Thus, the partial circle segment 94 may be able to change in dimension (e.g., widen out) under certain circumstances.

In some embodiments, a distalmost segment 95 of the distal tip 92 can form a full circle again, and thus the open segment 96 may not extend along the entire distal tip 92. In some embodiments, the open segment 96 may extend along the entire distal tip 92. In some embodiments, the distalmost segment 95 of the distal tip 92 can be tapered. In some embodiments, the distal tip 92 can terminate at a rounded atraumatic end to minimize tissue damage during implantation. In some embodiments, the distal tip 92 can have a lumen which can allow it to pass over a guidewire.

In some embodiments, the distal tip 92 can be pre-shaped to match a desired anatomical location. For example, the distal tip 92 can comprise a preset nitinol spine, such as discussed below, having a curvature that matches the desired anatomical location. Thus, the distal tip 92 can bend in the same direction as the curvature required for the delivery system 10 to travel from the septum hole to the mitral valve.

In some embodiments, as shown in FIG. 14, the distal tip 92 of the guide sheath 90 can have buckle points 93 between stiff sections 88 allowing the guide sheath 90 to conform with a patient's anatomy. The buckle points 93 can comprise one or more rings/segments of a weakened wall in the distal tip 92. The buckle points 93 can provide for multiple bending points, allowing for the distal tip 92 to bend at the buckle points 93 such as when the guide sheath 90 abuts against portions of a patient's vasculature system. The bendable distal tip 92 can advantageously allow the distal tip 92 to bend as the distal tip 92 is advanced through the vasculature of the patient, thus reducing or preventing damage to the patient. For example, if the distalmost segment 95 is delivered into the left ventricle or within the native mitral annulus, the distalmost segment 95 may be delivered so that it is supported by the more rigid native anatomical landmarks such as the left ventricle or the mitral annulus, and the distal tip 92 may bend in multiple locations as shown in FIG. 14 between the native mitral valve and the transseptal puncture. This allows for longer, stiffer implants to be utilized because the delivery path does not require as sharp of a turn once crossing the septum in order to reach the mitral valve.

Figure 16:
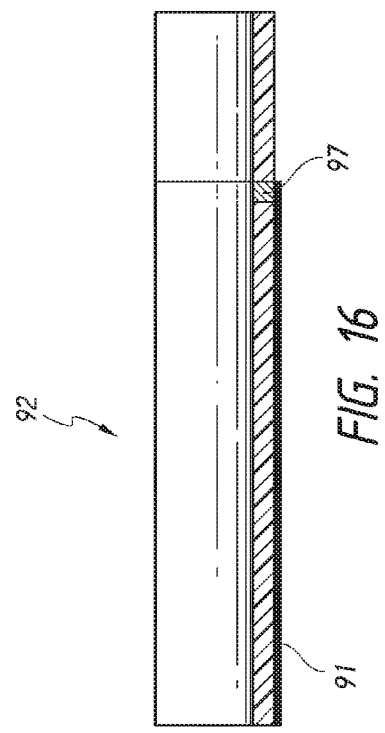
FIG. 16 illustrates a longitudinal sectional view along the distal end of the guided sheath of FIG. 14.

FIG. 16 illustrates a side cross-section of the distal tip 92 similar to the one shown in FIG. 14. FIG. 16 illustrates some additional components which can be used with the guide sheath 90, though may not be included in all embodiments. For example, the guide sheath 90 can include a pull wire 91 attached to an anchor ring 97 which can allow for some manipulation of the sheath 90 during the insertion through the vasculature of a patient by pulling and releasing the pull wire 91. The pull wire 91 can be coupled to the guide sheath 90 (either in the tube portion 89 or the distal tip 92) from a proximal end of the guide sheath 90 to the distal end. The anchor ring 97 can be located near the distal end of the distal tip 92 or near the distal end of the tube portion 89, though the particular location is not limiting. The pull wire 91 may be used to redirect the guide sheath during advancement of the guide sheath 90 through the vasculature of the patient, for example, when passing through an opening of the patient's anatomy or around a sharp turn. For example, the anchor ring 97 can transmit the pulling force of the pull wire 91 along a circumference of the guide sheath 90 to facilitate redirecting of the guide sheath 90. Further, the pull wire 91 and the anchor ring 97 can advantageously allow a straight guide sheath 90 instead of a guide sheath with a pre-curved distal tip to be used. The straight guide sheath can be more easily advanced through the patient's anatomy than the guide sheath with the pre-curved distal tip. When the distal tip 92 of the straight guide sheath 90 has been advanced to its desired location, the pull wire 91 may be pulled so that the distal tip 92 forms a tightened curve for tracking the delivery system 10. The pull wire 91 may be located on an outer or inner surface of the partial circle segment 94.

In some embodiments, the distal tip 92 can comprise an articulated spine 98, such as a laser-cut nitinol spine, that is semi-rigid. In some embodiments, the spine 98 can have a preset curvature for passing along the patient's vasculature. FIG. 17 illustrates a flat pattern view of the laser-cut spine 98. As shown, the laser-cut spine 98 can have slits 982 and/or perforations/holes/apertures 984. The slits 982 or perforations 984 can run in a radial and/or longitudinal direction. The slits 982 can extend from the outer perimeter of the spine 98 towards the interior. In some embodiments, the slits 982 can be generally triangular in shape, but can include a circular portion 983 where the slits 982 end at the central spine 985. In some embodiments, the slits 982 can be shaped so that the flanges 987 between the slits are angled in a particular direction (such as distal or proximal).

The perforations 982 can be located on the flanges 987. In some embodiments, the flanges 987 can each contain two perforations 982, with one perforation 982 located radially outward from the other preformation 982.

In some embodiments, the spine 98 can contain two end portions 989 on opposite longitudinal ends of the spine 98. The end portions 989 can be generally rectangular in shape, though one or both may be modified to accept one of the slits 982. Further, the end portions 989 may include a number of perforations 982.

In other embodiments, the wall of the distal tip 92 can also have cutouts of various shapes not discussed above, and the particular shapes are not limiting.

The laser-cut spine 98 can be rolled up to form a wall of the distal tip 92, which can be open (with an open segment) or openable (with overlapping walls that can be opened by expanding the spine 98 to remove the overlap). Specifically, the laser-cut spine 98 can be rolled up such that a first longitudinal edge 986 of the spine 98 does not touch a second longitudinal edge 988 of the spine 98, forming a partial circle segment similar to the partial circle segment 94 shown in FIG. 15. The laser-cut spine 98 can also be rolled up such that the first longitudinal edge 986 of the laser-cut spine 98 overlap with the second longitudinal edge 988 of the laser-cut spine 98, forming an openable distal tip with an overlapping section. The first and second longitudinal edges 986, 988 can move relative to each other so that the distal tip 92 can contract or expand, e.g. when a device passes through the distal tip 92. In some embodiments, the distal tip 92 may comprise a shape memory alloy or superelastic alloy with a memorized shape. In some embodiments, the distal tip 92 may be articulated by a pull wire, as discussed above. In some embodiments, the spine 98 may be covered by a layer of material, such as ePTFE, to form a rectangular shape so the slits 982 are covered.

In some embodiments, an expandable piece of cloth (not shown in FIG. 17) can line the open segment 96 of the distal tip 92 made from the rolled-up laser-cut spine 98. The cloth can expand when stiffer sections of the delivery system 10 pass through the distal tip 92. The stiff sections of the delivery system 10 may not bend along the curvature of the distal tip 92 and a portion of the stiff sections can partially protrude outside a lumen formed by the wall of the distal tip 92. The expandable cloth advantageously prevents the stiff sections from getting caught on the heart tissue (or other vascular tissue) and causing trauma.

Embodiments of the disclosed guide sheath 90 can be advantageous for insertion of the delivery system 10 to transseptally deliver a replacement heart valve to a mitral valve location, specifically by reducing or preventing any damage to the vasculature through the insertion of the delivery system 10 and by making it easier to track the delivery system 10 and implant 70 to the native mitral valve. Similar to the steps shown in FIG. 12, in one embodiment a guidewire (not shown) can be placed in the ipsilateral femoral vein and advanced to the right atrium. A transseptal puncture using known techniques can then be performed to obtain access to the left atrium. The guidewire can then be advanced in to the left atrium and then to the left ventricle. The guidewire can extend from the ipsilateral femoral vein to the left atrium. Unlike the steps shown in FIG. 12, the guide sheath 90 eliminates the need for snares for guidewire manipulation.

With the guidewire in place, the guide sheath 90 can be introduced into the body over the guidewire to the mitral valve from the left atrial septum. The guide sheath 90 can be positioned such that the tube portion 89 is positioned and crosses the transseptal puncture. Alternatively, the distal tip 92 may be placed in the transseptal puncture, where the openable wall would be compressed by the septum. The distal tip 92 can reach before, at or past the mitral valve. In one embodiment, an introducer sheath and/or catheter (not shown in FIGS. 14-17) may retain the semi-rigid distal tip 92 when the guide sheath 90 is introduced over the guidewire. In another embodiment, a standard introducer device (not shown in FIGS. 14-17) can be used to aid the introduction of the guide sheath 90 with the pre-shaped, such as pre-curved, distal tip 92. For example, the introducer device can be a rod or tube that is more rigid than the pre-shaped distal tip 92 and can be inserted into the lumen of the guide sheath 90 to hold the pre-shaped distal tip 92 straight before advancing the guide sheath 90 into the patient. The introducer device can be retracted after the guide sheath 90 has reached the desired location and the distal tip 92 can then resume its preset shape. The introducer device can advantageously allow easier introduction of the pre-shaped distal tip 92 of the guide sheath 90 across the septum. Once at its desired location, the distal tip 92 can be supported by more rigid native anatomical landmarks such as the left ventricular wall or the mitral valve annulus. The support from the anatomical landmarks can provide additional rigidity to the guide sheath 90 to help the delivery system 10 to make the turn toward the mitral valve after the delivery system 10 passes the septum puncture. In some embodiments, once the guide sheath distalmost segment 95 is supported by the native mitral valve or left ventricle, the distal tip 92 would be able to flex or bend as described above to provide a suitable delivery path.

The guide sheath 90 described herein advantageously serves several functions. In percutaneous procedures, it can be difficult to introduce a device through the anatomy to the desired location due to the length or size of the implant and the delivery device. Specifically, during transseptal mitral procedures, a sharp turn may need to be made across the septum in order for the implant and the delivery device to reach and cross the mitral valve. This can be especially difficult when attempting to introduce a long and stiff device, such as a transcatheter mitral valve.

Accordingly, the guide sheath 90 can eliminate the need for the distal portion 29 of the delivery system 10 to make a sharp turn to reach the desired location. The distal tip 92 of the guide sheath allows the delivery system 10 to utilize a diagonal length across the atrium as its limiting dimension for crossing instead of a horizontal distance across the atrium. For example, a long and rigid delivery component passing through the septal puncture into the left atrium will be limited by the horizontal distance across the atrium before it can be articulated vertically in order to pass through the mitral valve annulus. By comparison, when using a guide sheath 90 as described herein, the delivery system 10 can be advanced along a diagonal pathway in the left atrium. A diagonal pathway potentially allows even longer implant devices to be introduced into the desired location. Further, the guide sheath 90 also prevents the prosthesis 70 or the delivery system 10 from getting caught on the non-uniform heart tissue and potentially causing damage to the heart tissue.

As shown in FIG. 14, a lumen formed by the wall of the distal tip 92 allows the delivery system 10 to track along a curvature of the inner wall of the distal tip 92 as the delivery system 10 is directed to a desired position. Specifically, the closed segment of the distal tip 92 provides a bearing surface to be pushed against by the delivery system 10 and directs the elongate shaft assembly 12 to cross the mitral valve. The open segment 96 allows stiff sections of the delivery system 10 or the prosthesis 70 to pass without bending at the stiff sections. The open segment 96 also allows the distal tip 92 to flatten to a wider arc to keep the delivery system 10 contained. In embodiments of the distal tip 92 with the overlapping section, the overlapping section also aids in preventing the delivery system 10 from leaving the track.

Once the prosthesis 70 has been delivered to its desired location using the delivery system 10, it can be deployed using the methods described herein. In some embodiments, the distal tip 92 can be an attachment to a conventional catheter used to cross a transseptal puncture and remains during deployment of the prosthesis 70. Having the distal tip 92 as an attachment provides the advantage of not adding additional accessories to the procedure because the crossing catheter is a standard part of the procedure. In other embodiments, the guide sheath 90 is an independent unit. The guide sheath 90 can have a working length of about 80 cm and can act as both a femoral sheath and a septal working hole. The guide sheath 90 can advantageously be retracted once the delivery system 10 crosses the mitral valve so as to not avoid interfering with deployment of the prosthesis 70.

In some embodiments, a portion of the openable segment of the distal tip 92 instead of the full-circle section of the guide sheath 90 can span across the septum hole. Having an openable segment across the septum allows the space of the right atrium to be utilized for delivering even longer lengths can access the left atrium. The overlapping walls discussed above can be compressed by the septum and provide a smooth working surface across the septum hole while still guiding the long device.

In some embodiments, short devices can also require a specified septal puncture distance above the annulus in order to make the sharp turn toward the mitral valve. The guide sheath 90 can allow for septum punctures having lower than ideal heights and still guide the implant device to be coaxial with the mitral valve.

In some embodiments, the guide sheath may be used to provide a bearing surface to redirect any long implantable devices that are required to be advanced around corners in the patient's anatomy. For example, the guide sheath may be used to redirect a delivery device and implants to cross the tricuspid valves.

Anchored Guide Wire

Embodiments of the delivery system 10 can eliminate the need for snaring as discussed above through the use of an anchored guidewire shown in FIG. 18 instead of the guidewire 105.

Figure 20:
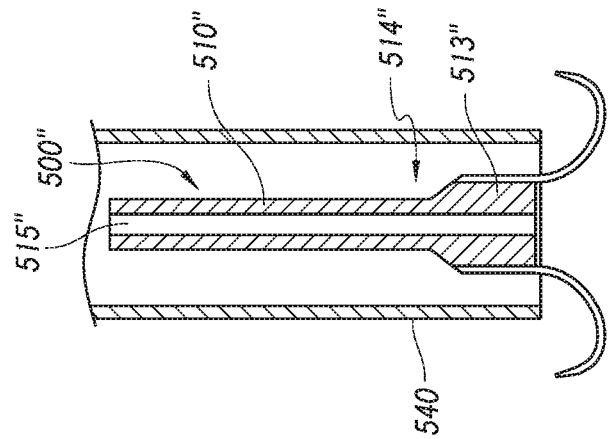
FIG. 20 illustrates a cross-sectional view of another embodiment of an anchored guidewire which can be incorporated into embodiments of the delivery system.
Figure 19:
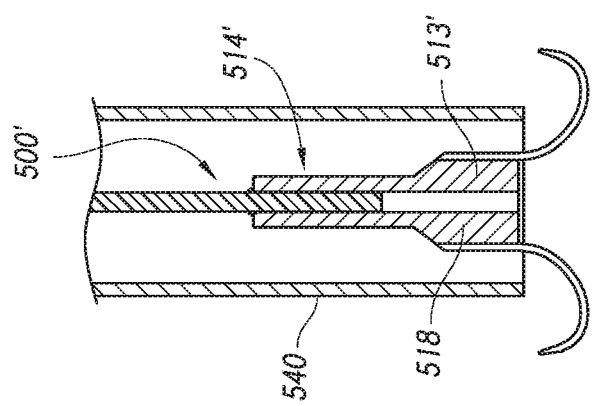
FIG. 19 illustrates a cross-sectional view of an embodiment of an anchored guidewire which can be incorporated into embodiments of the delivery system.

For example, an anchored guidewire 500, 500', 500" can comprise one or more anchors 514, 514', 514" attached to a guidewire to form an anchored guidewire 500, 500', 500" as shown in FIGS. 18-20. The anchors 514, 514', 514" can be coupled to the guidewire mechanically or via welding (such as in a lumen of the anchors 514, 514', 514" discussed below), or other methods of coupling known in the art. In some embodiments, the anchor 514, 514', 514" is made of nitinol, though the particular material is not limiting. The anchor 514, 514', 514" is configured to engage tissue, such as heart tissue in the left ventricular wall at or near the apex of the heart, and provide secure guidewire placement. In some embodiments, the anchor 514, 514', 514" can comprise a hook, barb, or other anchoring mechanisms.

FIG. 18 illustrates an exploded view of an embodiment of an anchored guidewire 500. As shown, the anchor 514 can include a torque shaft 510, an anchor connector 516 having a tapered proximal end 526, a retainer ring 512 configured to surround the tapered proximal end 526 of the anchor connector 516, and an anchor portion 513. The anchor portion 513 can have one or more hooks 520 (or 520' and 520") on a distal end of the anchor portion 513 and a ring portion 522 on a proximal end of the anchor portion 513. Further, the torque shaft 510, the retainer ring 512, the anchor portion 513, and the anchor connector 516 can have a lumen 515 extending through them.

To assemble the anchor 514, the anchor connector 516 can slide into the lumen of the anchor portion 513 from the distal end of the anchor portion 513. The anchor connector 516 can include a plurality of raised portions 517 on an outer surface proximate a distal end of the anchor connector 516. The raised portions 517 can abut the ring portion 522 of the anchor portion 513 on a distal end of the ring portion 522 to stop the anchor connector 516 from sliding past the anchor connector 516. The retainer ring 512 can then slide past the tapered proximal end 526 of the anchor connector 516 and abut the ring portion 522 of the anchor portion 513 on a proximal end of the ring portion 522. The retainer ring 512 can then be secured to the anchor connector 516 in a manner described above, for example, by welding. The torque shaft 510 can also slide into the lumen of the anchor connector 516 from the proximal end of the anchor connector 516 and be secured to the anchor connector 516 in a manner described above, for example, by welding. The guidewire can then be attached to the anchor 514, forming the anchored guidewire 500. The anchored guidewire 500 is configured to be used with the delivery system 10. The anchored guidewire 500 is also configured to be used with other delivery devices with a single lumen or multiple lumens.

FIG. 19 shows an embodiment of the anchored guidewire 500'. Similar to the anchored guidewire 500 in FIG. 18, the anchored guidewire 500' also can include an anchor portion 513' similar to the anchor portion 513. Unlike the anchored guidewire 500 in FIG. 18, the anchored guidewire 500' can also comprise a standard guidewire instead of the torque shaft 510 shown in FIG. 18. A distal end of the standard guidewire can be welded (or otherwise attached) to a housing 518 at a proximal end of the housing 518. The anchor portion 513' can be coupled to a distal end of the housing 518. The housing 518 can therefore replace the anchor connector 516, the torque shaft 510, and the retainer ring 512 shown in FIG. 18. In some embodiments, the housing 518 can be made of CoCr, though the particular material is not limiting. The anchored guidewire 500' is configured to be used with the delivery system 10. The anchored guidewire 500' is also configured to be used with other delivery devices with a single lumen or multiple lumens.

FIG. 20 shows yet another embodiment of the anchored guidewire 500". Similar to the anchored guidewire 500 in FIG. 18, the anchored guidewire 500" can include an anchor portion 513" similar to the anchor portion 513 in FIG. 18. The anchored guidewire 500" can also include a torque shaft 510" similar to the torque shaft 510 in FIG. 18 except that a distal end of the torque shaft 510" has an increased outer diameter so that the anchor portion 513" can be directly coupled to the distal end of the torque shaft 510" without the anchor connector 516 and the retainer ring 512 in FIG. 18. The anchored guidewire 500" is configured to be used with the delivery system 10. The anchored guidewire 500" is also configured to be used with other delivery devices with a single lumen or multiple lumens.

During a surgical procedure, a catheter 540, such as an articulating catheter (the distal end of which is shown in FIGS. 19 and 20) can first be introduced through a septum puncture, through the left atrium and then into the left ventricle until a distal tip of the catheter 540 presses against the wall of the left ventricle. For example, the distal tip of the catheter 540 presses against the wall of the left ventricle near the apex of the heart. The catheter 540 can have features that enable the catheter 540 to bend in one direction such that the catheter 540 can pass the septum puncture and then bend to cross the mitral valve.

The anchored guidewire 500, 500', 500" can then be inserted through the catheter 540 to reach the left ventricle. The hooks 520, 520', 520" of the anchor portions 513, 513', 513" can be deflected distally when the anchor portions 513, 513', 513" travel inside the catheter 540. Thus, as the anchored guidewire 500, 500', 500" is translated distally, the hooks 520, 520', 520" can pierce the heart tissue. The hooks 520, 520', 520" of the anchor portions 513, 513', 513" can then deflect radially outward and back proximally once outside of the catheter 540 to catch the wall of the left ventricle, thus keeping the anchored guidewire 500, 500', 500" stable.

In some embodiments, the anchored guidewire 500, 500', 500" can be pre-loaded into a lumen of the catheter 540, such as an articulating catheter (the distal end of which is shown in FIGS. 19 and 20), before the catheter 540 is introduced into the patient. For example, the anchored guidewire 500, 500', 500" can be pre-loaded such that the anchor portions 513, 513', 513" are located at a small distance, such as 2 mm-10 mm, proximally from a distal end of the catheter 540. Pre-loading the anchored guidewire 500, 500', 500" can advantageously allow the user, such as a surgeon, to advance the anchored guidewire 500, 500', 500" distally over a smaller distance for the anchor portions 513, 513', 513" to be pushed out of the catheter 540 and anchored into the wall of the left ventricle than having to advance the anchored guidewire 500, 500', 500" through an entire length of the catheter 540.

For the anchored guidewire 500, 500', 500" that has a lumen 515, 515", a separate guidewire can be inserted through the lumen 515, 515" prior to deploying the prosthesis 70. A balloon loaded on the separate guidewire can be inflated to detect any chordae tendineae when crossing the mitral valve. In some embodiments, the catheter 540 can have a balloon (not shown in FIGS. 19 and 20) on an outer wall of the catheter 540. Instead of having to insert the separate guidewire with the balloon, the balloon on the outer wall of the catheter 540 can be inflated to check for the presence of entangled chordae tendineae. The catheter 540 can then be removed and the delivery system 10, with the valve prosthesis 70 (with or without guide sheath 90), can be introduced over the anchored guidewire 500, 500', 500". When the delivery system 10 is about to cross the mitral valve, a user can apply tension on the anchor guidewire 500, 500', 500", such as by pulling on the anchored guidewire 500, 500', 500". The anchor portions 513, 513', 513" can provide an opposing force and cause a straightening of the anchored guidewire 500, 500', 500". The straightening can cause the delivery system 10 to bend downward toward the anchor portions 513, 513', 513" along the anchored guidewire 500, 500', 500". The torque shaft 510, 510" of the anchored guidewire 500, 500" or the standard guidewire of the anchored guidewire 500' can act as a rail, allowing the delivery system 10 to glide across the mitral valve.

Following deployment of the prosthesis 70, the catheter 540 can be reintroduced to abut against the heart tissue around the anchored guidewire 500, 500', 500". The anchored guidewire 500, 500', 500" can then be pulled into the catheter 540, compressing the hooks 520, 520', 520" within the catheter 540 to disengage the hooks 520, 520', 520" from the heart tissue and retract the anchored guidewire 500, 500', 500".

The anchored guidewire 500, 500', 500" allow for a recapturable method of gaining secure guidewire placement. The catheter 540 ensures that the user is able to place the anchor portions 513, 513', 513" in a desired location. The torque shaft 510, 510" of the anchored guidewire 500, 500" or the standard guidewire of the anchored guidewire 500' can act as a rail as opposed to other methods such as snaring, where the user must manipulate multiple devices in order for the delivery system 10 to cross the mitral valve.

Additional Embodiments of Prostheses and Replacement Valves

With reference to FIGS. 21-27, an embodiment of a prosthesis 1010 is shown. The illustrated prosthesis 1010 includes a frame 1020 that may be self-expanding or balloon expandable. The prosthesis 1010 may be a replacement valve that can be designed to replace a damaged or diseased native heart valve such as a mitral valve, as discussed above. The additional features of the replacement valve are not shown in FIGS. 21-27 in order to more clearly illustrate features of the frame 1020. It will also be understood that the prosthesis 1010 is not limited to being a replacement valve. In addition, it will be understood in FIG. 21, that only a front portion of the frame 1020 is shown for further ease of illustration.

Figure 21:
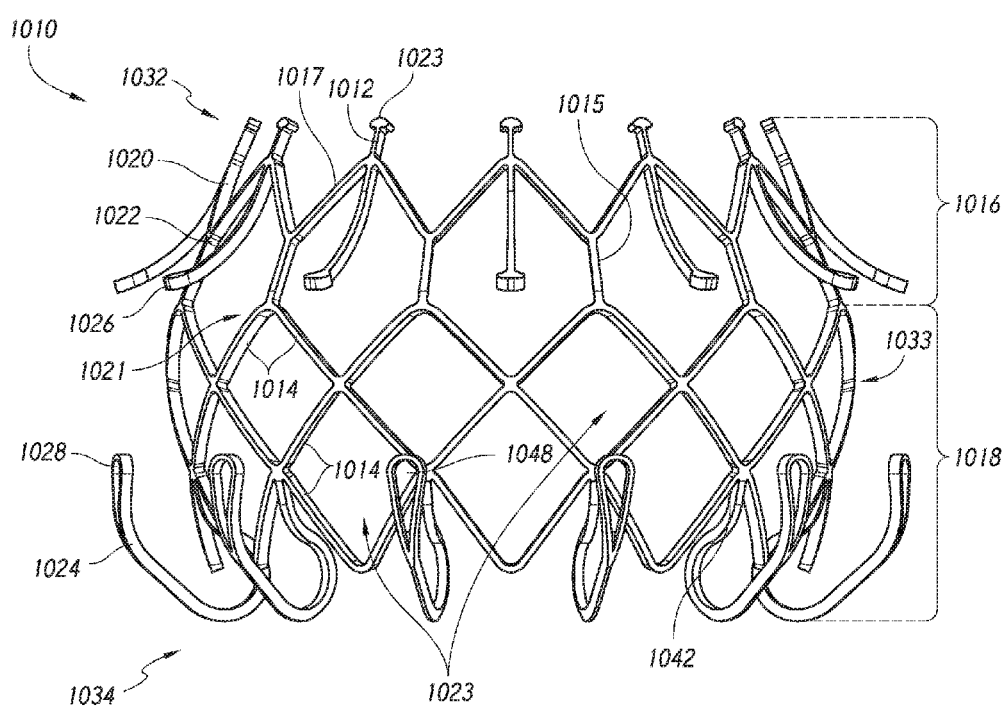
FIG. 21 shows a side view of an embodiment of a frame that may be delivered using the delivery systems described herein.
Figure 22:
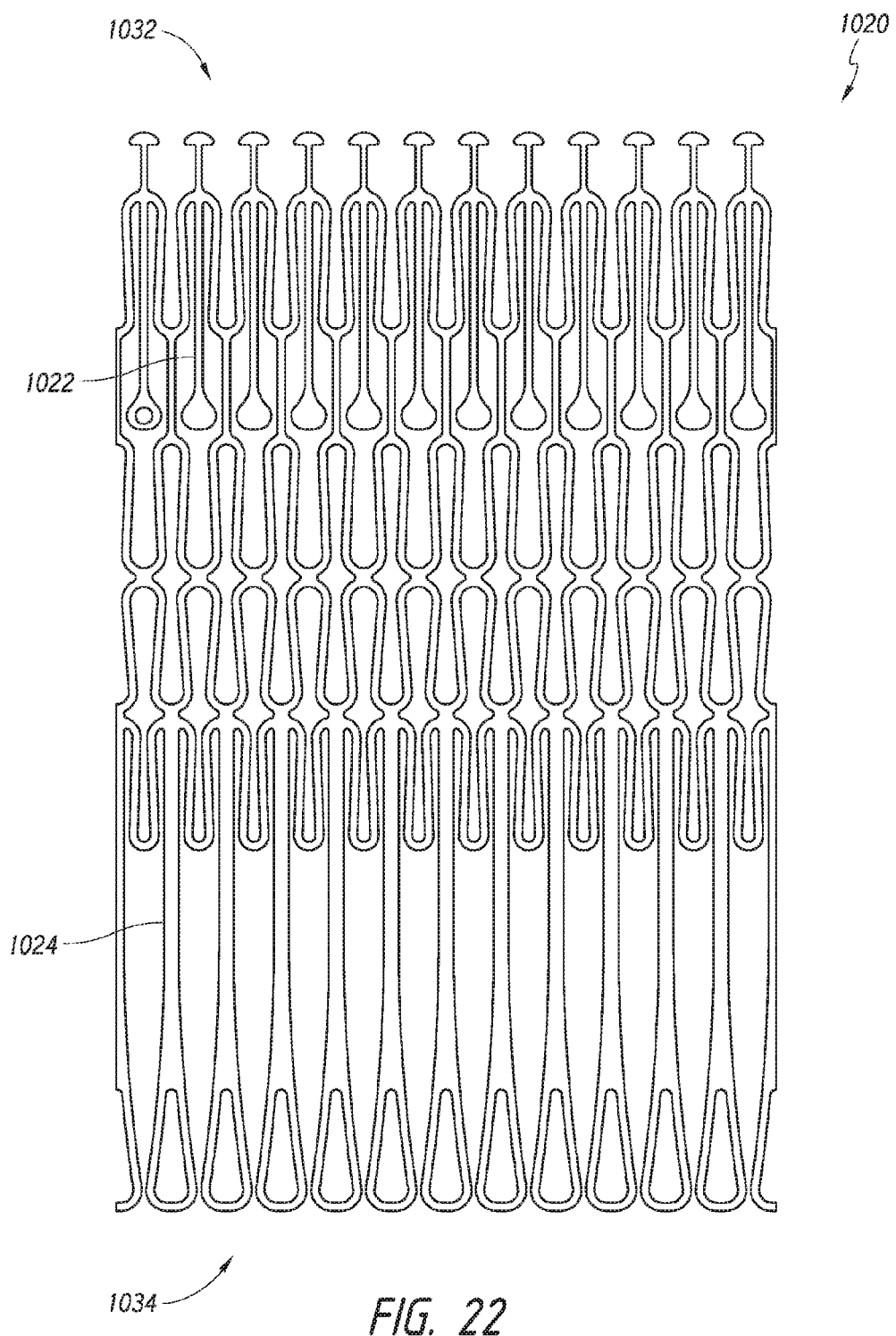
FIG. 22 shows a flat pattern of the frame of FIG. 21.
Figure 23:
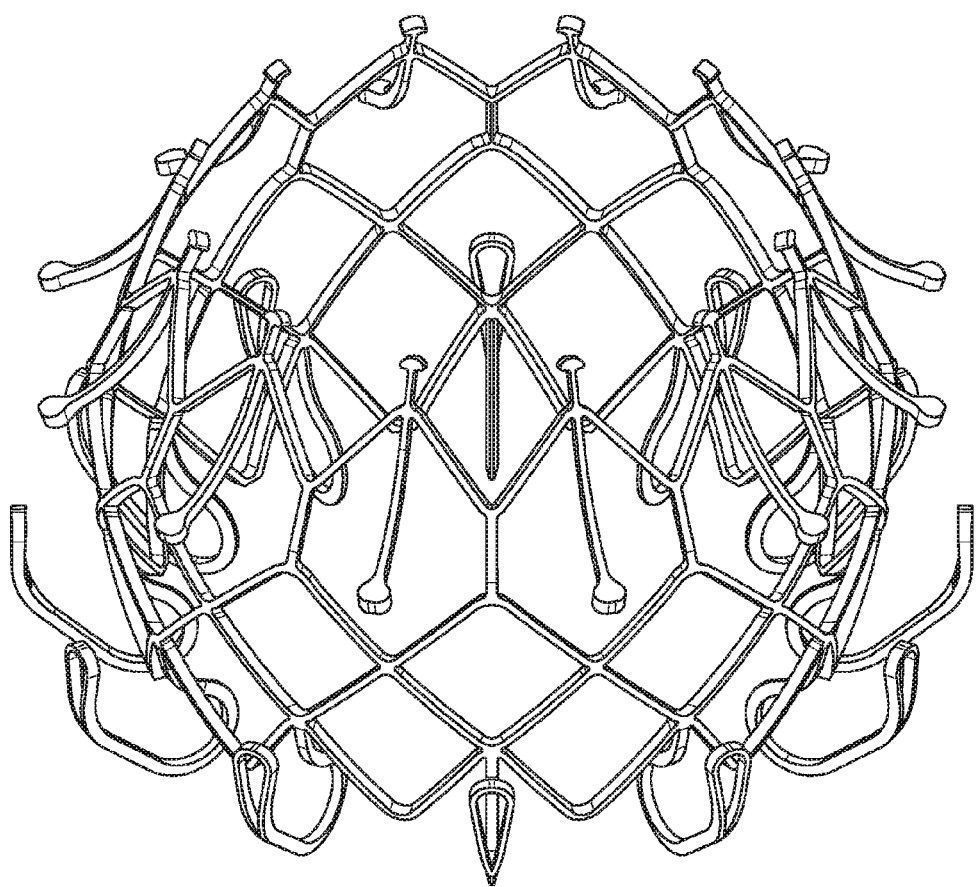
FIG. 23 shows a top perspective view of the frame of FIG. 21.
Figure 24:
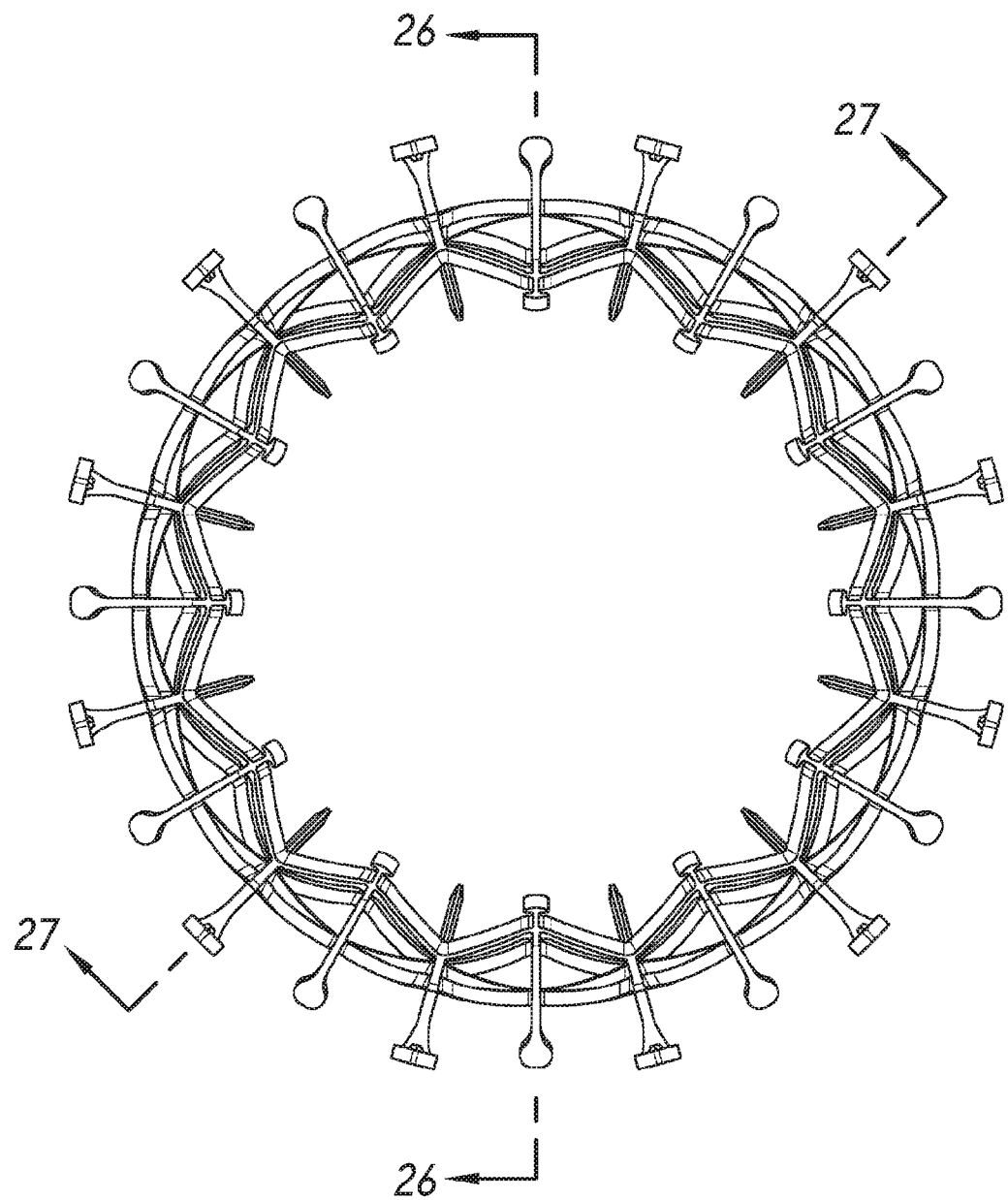
FIG. 24 shows a top view of the frame of FIG. 21.
Figure 25:
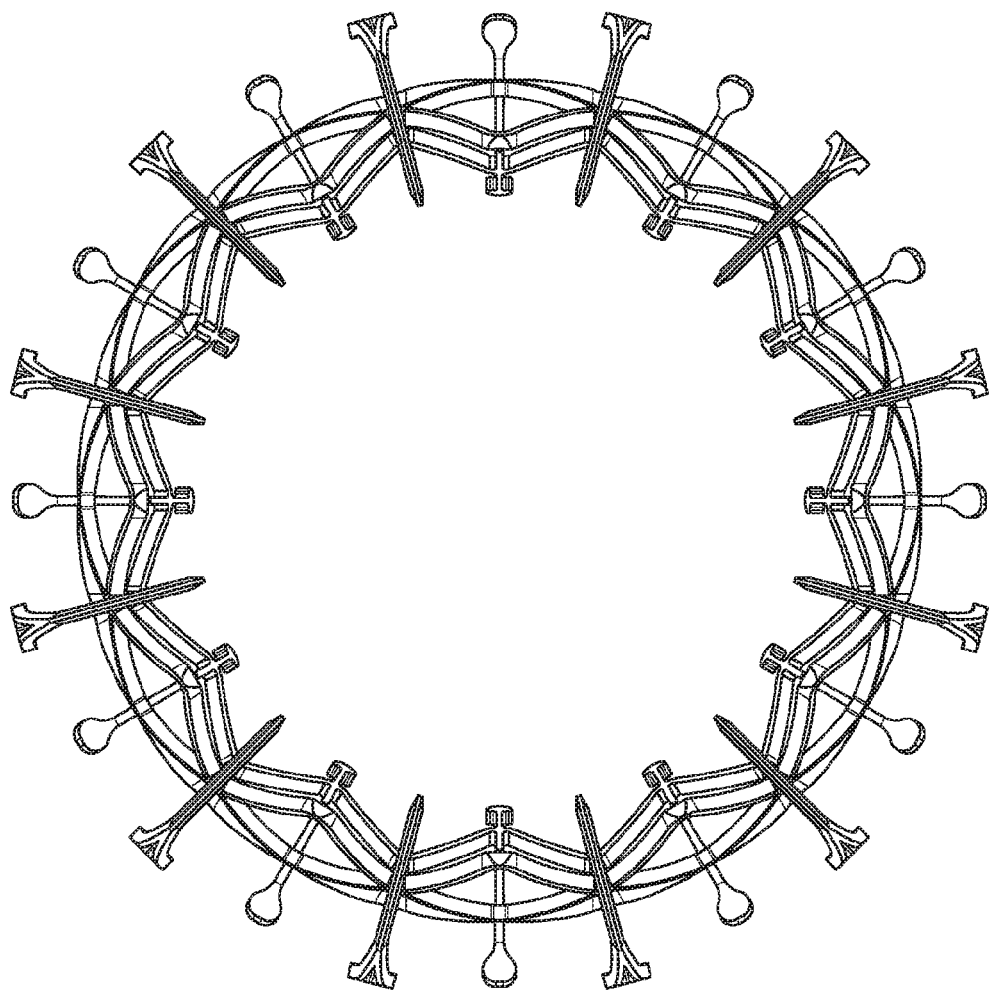
FIG. 25 shows a bottom view of the frame of FIG. 21.

The frame 1020 can be made of many different materials, but is preferably made from metal. In some embodiments, the frame 1020 can be made from a shape memory material, such as nitinol. A wire frame or a metal tube can be used to make the frame 1020. The wire frame of a metal tube can be cut or etched to remove all but the desired metal skeleton. In some embodiments a metal tube is laser cut in a repeating pattern to form the frame 1020. FIG. 22 illustrates the flat cut pattern of the frame shown in FIG. 22. As shown, one of the anchors 1022 can include an eyelet, which can help manufacturing with alignment. As the frame 1020 can be generally round and symmetric, the eyelet can serve as a reference position for frame dimensional measurements as well as alignment. However, the eyelet may not be included in all embodiments. Further, more eyelets can be included on the anchors 1022 as well, and the particular number of eyelets is not limiting. The flat pattern can be cut from a metal tube and then the tube can be shaped and/or bent to the expanded shape shown in FIG. 21. In some embodiments, the frame 1020 is self-expanding so that it naturally assumes the expanded shape or configuration. The frame 1020 can further be expanded and/or compressed and/or otherwise worked to have the desired shape or shapes, such as for introduction and implantation.

As shown, the frame when in an expanded configuration, such as in a fully expanded configuration, has a bulbous or slightly bulbous shape, with a middle portion 1033 being larger than the proximal 1032 and distal 1034 ends. In some embodiments, the inside diameter of the both ends can be the same, or it can be bigger on one end than the other, while still having a middle portion 1033 larger than both the proximal and distal ends 1032/1034. In some embodiments, the effective diameter of the distal frame end 1034 is smaller than the effective diameter of the middle portion 1033. The bulbous shape of the frame 1020 can advantageously allow the frame 1020 to engage a native valve annulus or other body cavity, while spacing the inlet and outlet from the heart or vessel wall. This can help reduce undesired contact between the prosthesis and the heart or vessel, such as the ventricular wall of the heart. In some embodiments, the frame 1020 may not have a bulbous portion, and can have substantially the same outer dimension along its entire length (e.g., cylindrical), or it may have one end larger than the other end. The prosthesis 1010 and frame 1020 may be similar to the replacement heart valves and associated frames disclosed in U.S. Pat. No. 8,403,983 and U.S. Publication Nos. 2010/0298931, 2011/0313515, 2012/0078353, 2014/0277390, 2014/0277422, and 2014/0277427 the entireties of each of which are hereby incorporated by reference and made a part of this specification. This is inclusive of the entire disclosure and is not in any way limited to the disclosure of the replacement heart valves and associated frames.

A number of struts collectively make up the frame 1020. FIG. 21 illustrates the frame in an expanded configuration with a number of proximal struts 1012 that extend substantially longitudinally to enlarged proximal ends 1013. A proximal row of circumferentially-expansible struts 1017 connects the proximal struts 1012, having a zig-zag or undulating shape such that between each proximal strut 1012, the struts 1017 form a V-shape. From the distal ends of each of the V's, vertical struts 1015 extend substantially longitudinally in a distal direction. The distal ends of the vertical struts 1015 then connect to a row of diamond-shaped cells 1023 formed by a plurality of circumferentially-expansible struts 1014 having a zig-zag or undulating shape. As illustrated, the proximalmost row of struts 1014 extend distally away from the distal ends of the vertical struts 1015 in a V-shape, thereby forming hexagonal-shaped cells 1021 bounded by the proximal row of struts 1017, the vertical struts 1015, and the proximalmost row of struts 1014. The embodiment of FIG. 21 further comprises a second, distal row of diamond-shaped cells 1023 further defined by additional circumferentially-expansible struts 1014, wherein the proximalmost corner of the second row of diamond-shaped cells 1023 coincides with the distalmost corner of the hexagonal-shaped cells 1021 and the side corners of the diamond-shaped cells in the first, proximal row.

The proximal struts 1012 and the vertical struts 1015 may be arranged so that they are parallel or generally or substantially parallel to a longitudinal axis of the frame. The proximal struts 1012 and the vertical struts 1015 can further be inclined relative to the longitudinal axis so that the proximal ends of the proximal struts 1012 are closer to the longitudinal axis than distal ends of the proximal struts 1012. The longitudinal axis of the frame 1020 may be defined as the central axis that extends through the center of the frame 1020 between the proximal 1032 and distal 1034 ends.

The illustrated embodiment includes one ring, or row of hexagonal or generally hexagonal cells 1021 shown in proximal portion 1016 of the frame 1020, and two rows of diamond-shaped cells 1023 shown in distal portion 1018. As discussed in more detail below, the proximal portion 1016 includes the portion of the hexagonal cells 1021 extending proximally from the distal end of vertical struts 1015 and may be considered to be or to include a substantially non-foreshortening portion. Foreshortening refers to the ability of the frame to longitudinally shorten as the frame radially expands. The distal portion 1018 includes the diamond-shaped cells 1023 extending distally from the distal ends of the vertical struts 1015 and may be considered a foreshortening portion. In some embodiments, the hexagonal cells 1021 can be irregular hexagons. For example, the hexagonal cells 1021 can be symmetrical about a vertical axis extending from proximal to distal ends of the hexagonal cell 1021. Vertical struts 1015 can form opposite sides, while circumferentially-expansible struts 1014 of two adjacent diamond-shaped cells 1023 in the proximalmost row can form a base of the hexagonal cell 1021 ending at a distalmost corner that is distal to the distal ends of the vertical struts 1015. These circumferentially-expansible struts 1014 can connect to the vertical struts 1015. Further, the proximal row of circumferentially-expansible struts 1017 can form the upper sides of the hexagonal cell 1021 that extend to a proximalmost corner of the hexagonal cell 1021 that is proximal to the proximal ends of vertical struts 1015. These circumferentially-expansible struts 1017 can connect to the proximal ends of the vertical struts 1015. In some embodiments, two of the sides of the hexagonal cells 1021 can be one length, while the other four sides of the hexagonal cells 1021 can be a greater length. In some embodiments, the two sides with the same length can be generally parallel to one another.

As described above, the frame 1020 has a proximal portion 1016 and a distal portion 1018. In FIG. 21 it can be seen that the proximal struts 1012 and the majority of the hexagonal cells 1021 are included in the proximal portion 1016, while circumferentially-expansible struts 1014 form the distal portion 1018 having a first, proximal row of diamond-shaped cells 1023 and a second, distal row of diamond-shaped cells 1023. As illustrated, adjacent cells between the proximal row and the distal row may share common struts. In some embodiments, the diamond-shaped cells 1023 in the second, distal row may have a larger longitudinal height than the diamond-shaped cells 1023 in the first, proximal row. When the frame is radially collapsed or compacted, the struts 1014 become more parallel with respect to the longitudinal axis of the frame, causing an outer diameter of the frame to decrease and the longitudinal length of the frame to increase in the distal portion 1018. As the frame moves from a compacted position to an expanded position, the longitudinal length of the frame can decrease due to foreshortening of the diamond-shaped cells 1023 in distal portion 1018. But, the frame length does not substantially change length in the proximal portion 1016 due to the vertical struts 1015, although the proximal row of circumferentially-expansible struts 1017 in the proximal portion 1016 may allow for some foreshortening.

The frame 1020 shown in FIG. 21 can have a relatively squat configuration, as opposed to, for example, the frame shown in FIG. 3. For example, the ratio of the width of the largest portion of the frame 1020 to the height (e.g., extending from the proximal 1032 to distal end 1034) of the frame 1020 when the frame is in its expanded configuration can be about 3:1, about 2.5:1, about 2.0:1, about 1.5:1, about 4:3, about 1.3:1, about 1.25:1, or about 1.0:1. Thus, in some embodiments the width at the largest portion of the frame 1020 can be greater than the height. Generally, the frame 1020 can have a larger aspect ratio than the prosthesis 70 shown in FIG. 3. In some embodiments, the height of portion 1016 can be greater than, equal to, or less than the height of portion 1018. In some embodiments, the height of proximal portion 1016 can be approximately ½ the height of distal portion 1018. In some embodiments, the frame 1020 can have an overall height of about 32 mm (or about 32 mm), which can be shorter than the height of the prosthesis 70 shown in FIG. 3 having a height of 37 mm (or about 37 mm). The frame 1020 can have an inner diameter of 40 mm (or about 40 mm). In some embodiments, the frame 1020 can have a height of 29, 30, 31, 33, 34, 35, or 36 mm (or about 29, about 30, about 31, about 33, about 34, about 35, or about 36 mm).

Foreshortening of the frame 1020 can be used to engage and secure the prosthesis to intralumenal tissue in a body cavity, for example tissue at or adjacent a native valve, such as a native valve annulus and/or leaflets. Opposing anchors 1022, 1024 can be constructed on the frame 1020 so that portions of the anchors, such as tips or ends 1026, 1028, move closer together as the frame foreshortens. As one example, this can allow the anchors 1022, 1024 to grasp tissue on opposite sides of the native mitral annulus to thereby secure the prosthesis at the mitral valve. In some embodiments, one set of anchors (such as anchors 1024) are secured to or grasp tissue, while the other set of anchors (such as anchors 1022) are used to provide stabilization and help align the prosthesis, and may or may not directly engage tissue, as described further below.

The anchors 1022, 1024 and anchor tips 1026, 1028 are preferably located along the frame 1020 with at least part of the foreshortening portion positioned between the anchors so that a portion of the anchors will move closer together with expansion of the frame. As shown, distal anchors 1024 are connected to the distal portion 1018, and may extend from distalmost corners of the diamond-shaped cells 1023. As illustrated, the distal anchors 1024 extend distally from distalmost corners of the proximal row of diamond-shaped cells 1023, such that the second, distal row of diamond-shaped cells 1023 extend longitudinally alongside a portion of the distal anchors.

Preferably, each of the anchors 1022, 1024 is positioned or extends generally radially outwardly from the frame 1020 so that the anchor tips 1026, 1028 are generally spaced away or radially outward from the rest of the frame 1020 and from where the base of the anchors connect to the frame. For example, the anchor tips may be located radially outward from the middle portion 1033 of the frame, with the tips 1026 and 1028 being axially spaced from one another. The middle portion 1033, which has the largest cross-sectional dimension when the frame is radially expanded, can be defined by the proximalmost row of diamond-shaped cells 1023. The anchors 1022, 1024 can include a base located on the anchor on a side opposite the tip. The base can be for example where the anchor begins to extend from or away from the frame 1020.

Proximal anchors 1022 are shown having a single strut extending into the hexagonal cells 1021 of portion 1016. Thus, the anchor 1022 extends from a proximal intersection of two segments of the hexagonal cell 1021, for example, from the proximalmost corner of the hexagonal cells 1021. As shown, the proximal anchors 1022 extend generally distally into the hexagonal cells 1021 while curving outwards away from the frame 1020. Thus, the anchor 1022 extends radially outwardly from the frame 1020 as it extends generally distally towards the tip 1026. The tips 1026 of the proximal anchors 1022 can end after extending approximately half the length or more of the hexagonal cells 1021. Further, the tips 1026 can extend farther outwards than the main body of the frame 1020.

In some embodiments, the tip 1026 of the anchor 1022 also includes an enlarged or bulbed portion 1026, which can be generally circular in shape, though the particular shape is not limiting. As illustrated, the bulbed portion 1026 is located at the distal end, though the bulbed portion 1026 can be positioned in other locations along the anchor 1022. The bulbed portion 1026 can have a radius greater than the width of the rest of the anchor 1022, making the bulbed portion 1026 larger than the rest of the anchor 1022. As illustrated, the enlarged or bulbed portions can extend in a direction generally or substantially perpendicular to the longitudinal axis, caused for example by gradual bending of the anchor 1022 distally and radially outwardly.

As another example, the distal anchors 1024 are shown having looped ends 1048. The looped ends can be larger near the tip to form a type of elongated teardrop. In some embodiments, the tips 1028 may be substantially flat. The looped end may assist the frame in not getting caught up on structures at or near the treatment location. For example, each loop can be configured so that when the frame is deployed in-situ and expands, the movement of each loop from a delivered position to a deployed position avoids getting caught on the papillary muscles.

Each distal anchor 1024 is connected to the frame at a base 1042. As illustrated in FIG. 21, the base of the distal anchor may be at a location where the corners of adjacent cells meet, such that the base is proximal to the distal end 1034 of the frame. In other embodiments, the base of the distal anchor may be at a distal most corner of a cell, which corresponds to a distal most point on the frame The distal anchors as illustrated extend from the base 1042 generally distally before bending back around in an arcuate and/or bent segment where the distal anchor extends generally proximally and radially outwardly from the frame. As shown, the anchors 1024 may also extend generally distally and radially inwardly from the base with respect to the frame such that the distal most point on the prosthesis has a smaller inside diameter than where the base 1042 connects to the frame. The inside diameter at the distal most point can be the same or substantially the same as the inside diameter of the proximal end, or may be smaller. As illustrated, the anchors 1024 may extend distally from the base 1042 and bend or curve radially inwardly and then curve approximately in a half-circle first further radially inwardly, and then around so that the anchor extends radially outwardly. This half-circle can provide a space for the distal ends of the leaflets to be stored, such as in the configurations described below. The anchors may then extend in a linear segment radially outwardly and proximally. Finally, the anchor may extend towards the tip 1028 in a direction parallel or substantially parallel to the longitudinal axis. Thus, the anchor as illustrated is bent around about 180 degrees from its base so that the tip 1028 extends in the opposite, proximal direction, which may be parallel or substantially parallel to the longitudinal axis of the frame. For example, in FIG. 21 it can be seen that the distal anchors 1024 are bent near the tips 1028 such that the ends of the anchors point proximally and are generally parallel with the longitudinal axis of the frame. Alternatively, the tip 1028 may extend generally proximally but still extend radially outwardly inclined or at an acute angle relative to the longitudinal axis of the frame It will be understood that the anchors can have various other configurations, including the various embodiments that follow. In some embodiments, each of the anchors can extend radially outwardly from the frame at an anchor base and terminate at an anchor tip. The anchors can be connected to the frame at one of many different locations including apices, junctions, other parts of struts, etc. The anchors can comprise first, second, third, or more spaced apart bending stages along the length of each anchor. The anchors can also extend either distally or proximally before and/or after one or more of the bending stages. A portion of the anchor may extend with the frame before or after any bending stages.

The tips or ends 1013 of proximal struts 1012 can be enlarged relative to other portions of the tips 1013. For example, the ends of tips 1013 can have a generally "mushroom" shape. The proximal struts 1012 and enlarged tips 1013 can form locking tabs used to engage a locking mechanism of a delivery system for the prosthesis. In some embodiments, the longitudinal extensions 1012 and the mushroom tips 1013 can be inclined generally radially inward.

In the illustrated embodiment of FIGS. 23-27 there are twelve distal anchors positioned circumferentially around frame and twelve proximal anchors positioned circumferentially around the frame. In some embodiments there may be 6 proximal anchors and 12 distal anchors, or vice versa. Some embodiments may include different numbers of anchors.

Figure 26:
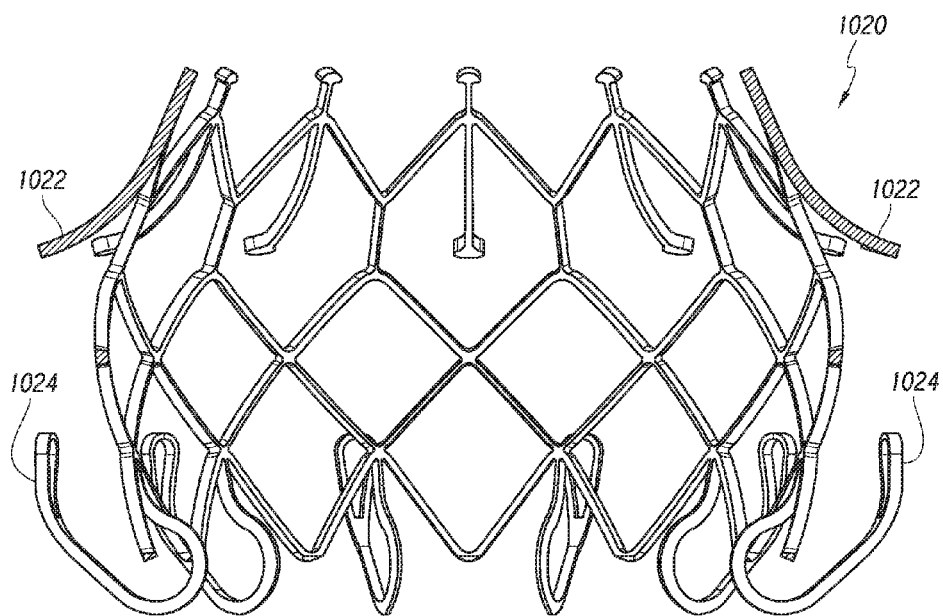
FIG. 26 shows a cross-sectional view of the frame of FIG. 21, through line 26-26 of FIG. 24.
Figure 27:
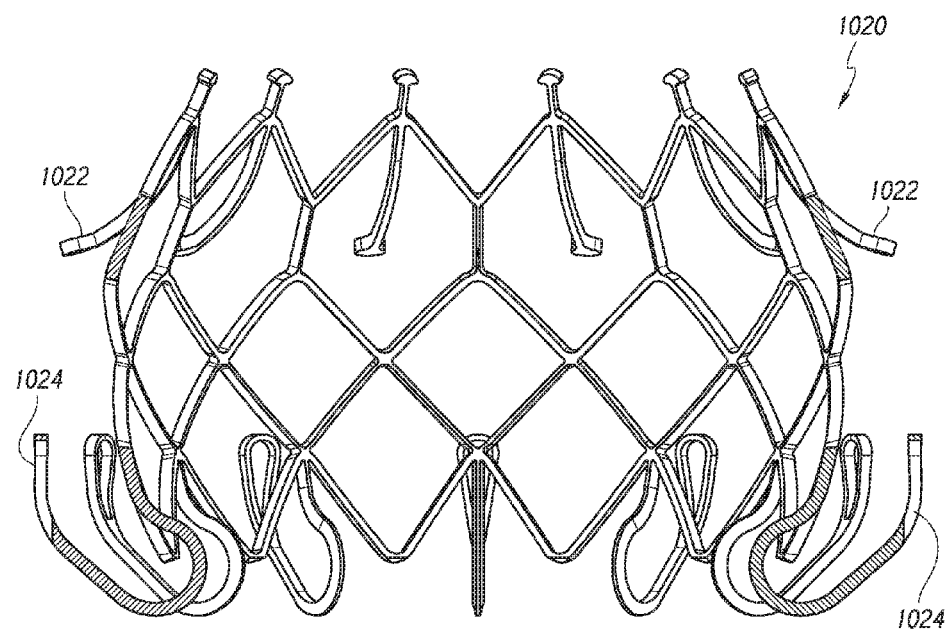
FIG. 27 shows a cross-sectional view of the frame of FIG. 21, through line 27-27 of FIG. 24.

In addition, the distal and proximal anchors may be arranged so the bases of the distal anchors and the bases of the proximal anchors are not circumferentially aligned, but rather are circumferentially offset from each other with the bases of the proximal anchors circumferentially located mid-way between adjacent bases of the distal anchors. As shown in FIGS. 26-27, which illustrate cross-sectional cuts for the frame 1020, the proximal anchors 1022 and distal anchors 1024 are not directly aligned with one another. For example, FIG. 26 illustrates a cross section through proximal anchors 1022 extending to the left and right of the frame 1020. As shown, while the proximal anchors 1022 are cut, the distal anchors 1024 are not. FIG. 27 illustrates the frame 1020 rotated so that the distal anchors 1024 are cut on the left and right sides of the frame 1020. Again, the proximal anchors 1022 are located circumferentially offset from the distal anchors 1024.

The anchor tips 1026 and 1028 as described above advantageously provide atraumatic surfaces that may be used to grasp intralumenal tissue without causing unnecessary or undesired trauma to tissue. For example, the proximal anchors tips 1026 and distal anchor tips 1028 may form flat, substantially flat, curved or other non-sharp surfaces to allow the tips to engage and/or grasp tissue, without necessarily piercing or puncturing through tissue.

Figure 28A:
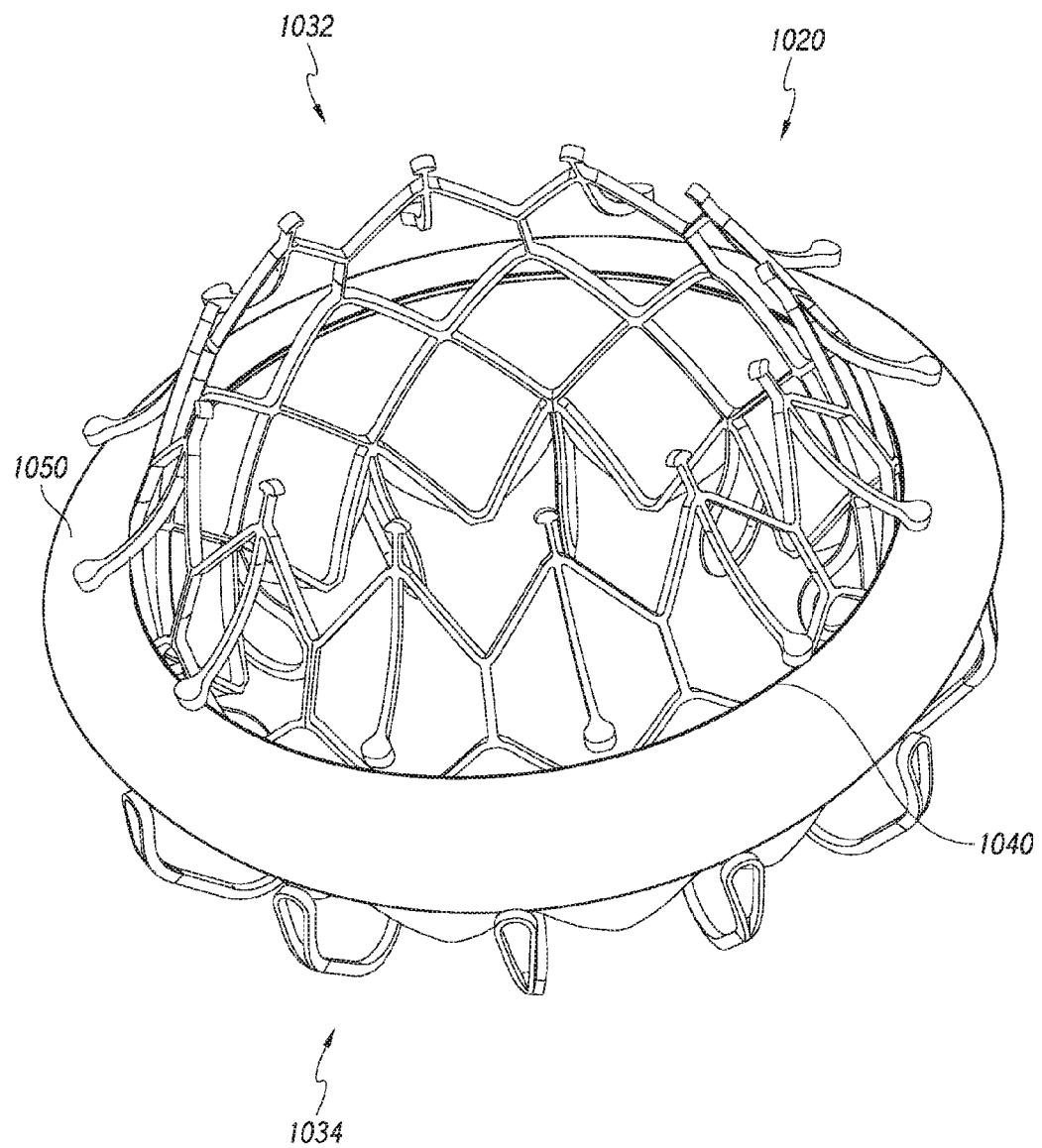
FIG. 28A-B show top and bottom perspective views of an embodiment of a replacement mitral valve comprising the frame of FIG. 21 and an outer skirt, with the valve body removed.
Figure 28B:
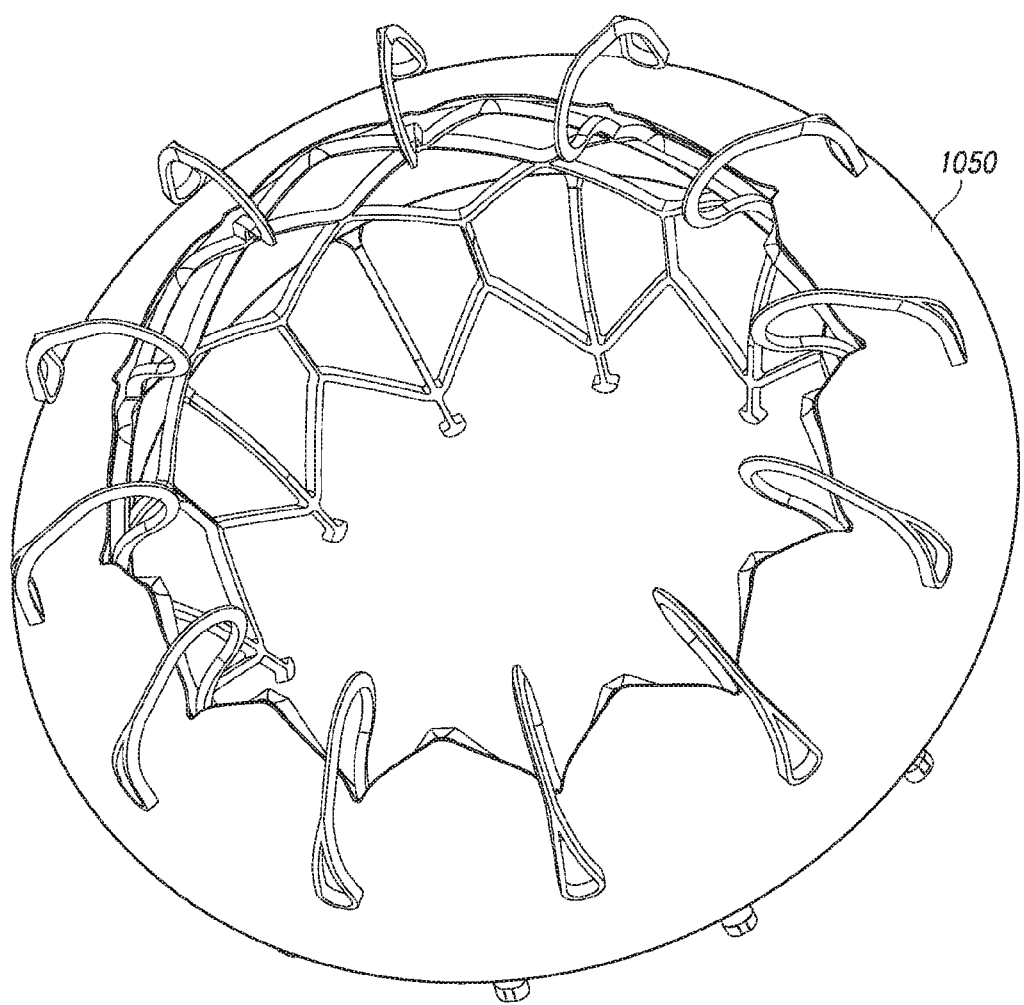
Figure 29:
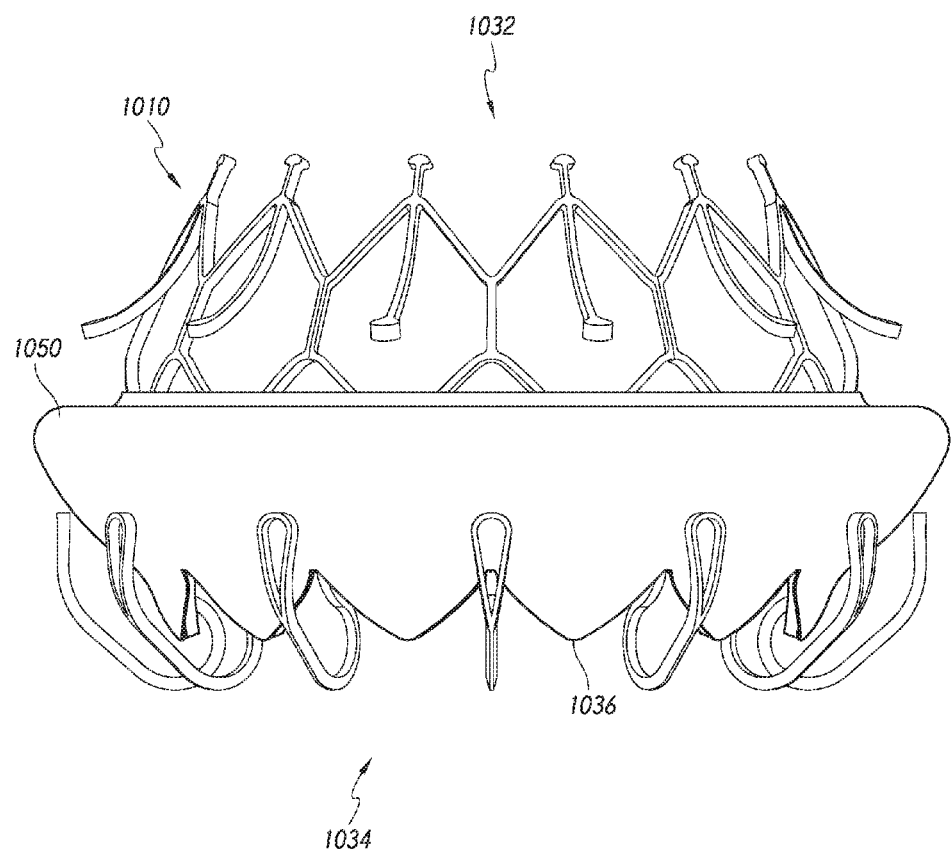
FIG. 29 shows a side view of the replacement mitral valve of FIGS. 28A-28B.

With reference to the embodiments of FIGS. 28A-29, a replacement heart valve such as a replacement mitral valve 1010 can include an annular flap 1050 which can be positioned around and secured to an exterior of the frame 1020. In the embodiments described herein, the valve body that includes the artificial valve leaflets that would be attached to the frame is not illustrated, but may be similar to the embodiments shown in U.S. Patent Publication No. 2015/0328000, hereby incorporated by reference. Further in the embodiments described herein, the flap that is discussed below may be similar to embodiments shown in U.S. Patent Publication No. 2015/0328000, hereby incorporated by reference. For example, the valve body can start from the proximalmost ends of the hexagonal cells 1021 described above, and can extend below the annular flap 1050. The annular flap 1050 can have a distal edge 1036 (shown in FIG. 29) secured at or proximate the distal end 1034 of the frame 1020 and extend to a proximal edge 1040 (shown in FIG. 28A) secured at or proximate an intermediate location on the frame 1020 between the proximal and distal ends 1032, 1034. In some embodiments, the distal edge 1036 of the annular flap 1050 can be provided with a shape that generally corresponds to the shape of the frame 1020. This can facilitate the securement of the flap 1050 to the frame 1020. For example, the distal edge 1036 can include a generally triangular pattern which follows the generally triangular, zig-zag or undulating pattern of the struts of frame 1020 along the distal end 1034 of frame 1010. Other shapes and/or patterns can be used along the distal edge 1036 of the annular flap 1050. In some embodiments, the distal edge 1036 of the annular flap 1050 can have no pattern. In some embodiments the distal edge 1036 does not follow the pattern of the struts of the frame 1020 and/or can have a different pattern from that of the struts.

In some embodiments, covers/cushions can be used to surround or partially surround the distal anchors 1024, specifically the tips 1028 of the distal anchors 1024, such as those described in U.S. Patent Publication No. 2015/032800, hereby incorporated by reference in its entirety. In some embodiments, the covers can either fit snuggly around the tips 1028 or can have extra padding so that the covers extend radially away from the frame 1020. In some embodiments, all of the distal anchors 1024 have the snug fitting covers. In some embodiments, all of the distal anchors 1024 have the padded covers. In some embodiments, some of the distal anchors 1024 have the padded covers and some have the snug covers. In some embodiments, not all of the distal anchors 1024 can have covers. In some embodiments, all of the distal anchors 1024 can have some sort of cover.

Reference is now made to FIGS. 30A-31B which illustrate schematic representations of an embodiment of a replacement heart valve 1010 positioned within a native mitral valve of a heart 83. A portion of the native mitral valve is shown schematically and represents typical anatomy, including a left atrium 102 positioned above an annulus 106 and a left ventricle 104 positioned below the annulus 106. The left atrium 102 and left ventricle 104 communicate with one another through a mitral annulus 106. Also shown schematically in FIGS. 30A-31B is a native mitral leaflet 108 having chordae tendineae 110 that connect a downstream end of the mitral leaflet 108 to the papillary muscle of the left ventricle 104. The portion of the replacement heart valve 1010 disposed upstream of the annulus 106 (toward the left atrium) can be referred to as being positioned supra-annularly. The portion generally within the annulus 106 is referred to as positioned intra-annularly. The portion downstream of the annulus 106 is referred to as being positioned sub-annularly (toward the left ventricle). In the illustrated embodiment, only a part of the foreshortening portion is positioned intra-annularly or sub-annularly, and the rest of the replacement heart valve 1010 is supra-annular. In some embodiments, all of the proximal portion 1016 can be super-annular, with the distal portion 1018 being intra-annular and/or sub-annular.

As shown in the situations illustrated in FIGS. 30A-31B, the replacement heart valve 1010 can be disposed so that the mitral annulus 106 is between the distal anchors 1024 and the proximal anchors 1022. In some situations, the prosthesis 1010 can be positioned such that ends or tips 1028 of the distal anchors 1024 contact the ventricular side of the annulus 106 as shown, for example, in FIGS. 30A-C. In some situations, the prosthesis 1010 can be positioned such that ends or tips 1028 of the distal anchors 1024 do not contact the annulus 106 as shown, for example, in FIGS. 31A-B, and may just contact a downstream side of the leaflet 108. In some situations, the prosthesis 1010 can be positioned such that the distal anchors 1024 do not extend around the leaflet 108 as illustrated, but rather are positioned radially inward of the leaflet. While FIGS. 30A-31B are described separately below, it should be understood that one or more of the situations illustrated in FIGS. 30A-31B may be present when the prosthesis 1010 is positioned at the implantation location, such as a native mitral valve. For example, in some situations the prosthesis 1010 may be positioned such that some distal anchors 1024 may contact the annulus 106 while other distal anchors 1024 may not.

With reference first to the situations illustrated in FIGS. 30A-31B, the replacement heart valve 1010 can be positioned so that the ends or tips 1028 of the distal anchors 1024 are on a ventricular side of the mitral annulus 106 and the ends or tips of 1026 the proximal anchors 1022 are on an atrial side of the mitral annulus 106. The distal anchors 1024 can be positioned such that the ends or tips 1028 of the distal anchors 1024 are on a ventricular side of the native leaflets radially outwardly beyond a location where chordae tendineae 110 connect to free ends of the native leaflets. The distal anchors 1024 may extend between at least some of the chordae tendineae 110 and, in some situations such as those shown in FIGS. 30A-C, can contact or engage a ventricular side of the annulus 106. It is also contemplated that in some situations, such as those shown in FIGS. 31A-B, the distal anchors 1024 may not contact the annulus 106, though the distal anchors 1024 may still contact the native leaflet 108. In some situations, the distal anchors 1024 can contact tissue of the left ventricle 104 beyond the annulus 106 and/or a ventricular side of the leaflets.

Figure 30A:
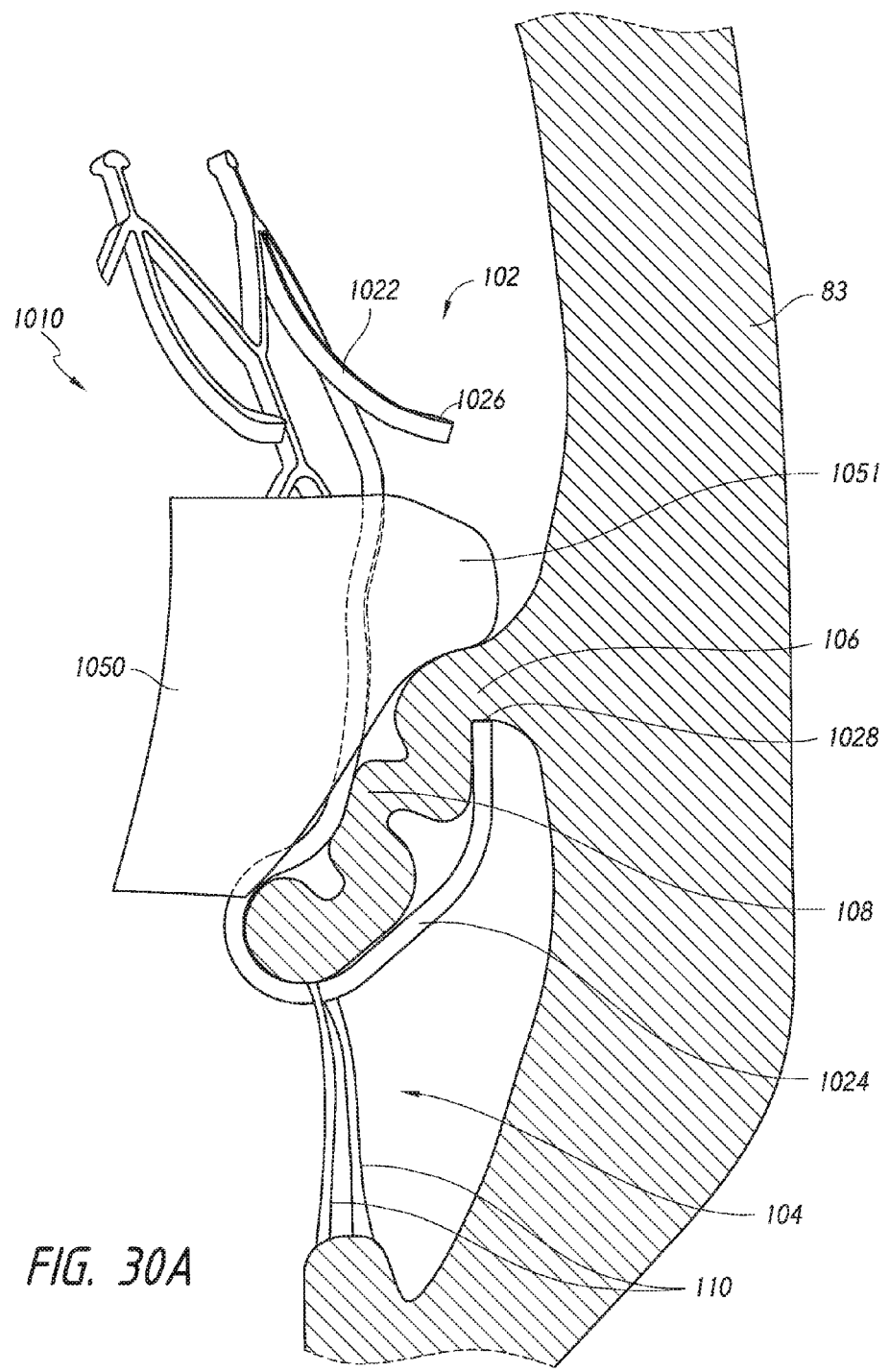
FIGS. 30A-C illustrate a schematic representation of the replacement mitral valve of FIGS. 28A-28B positioned within a native mitral valve.
Figure 30B:
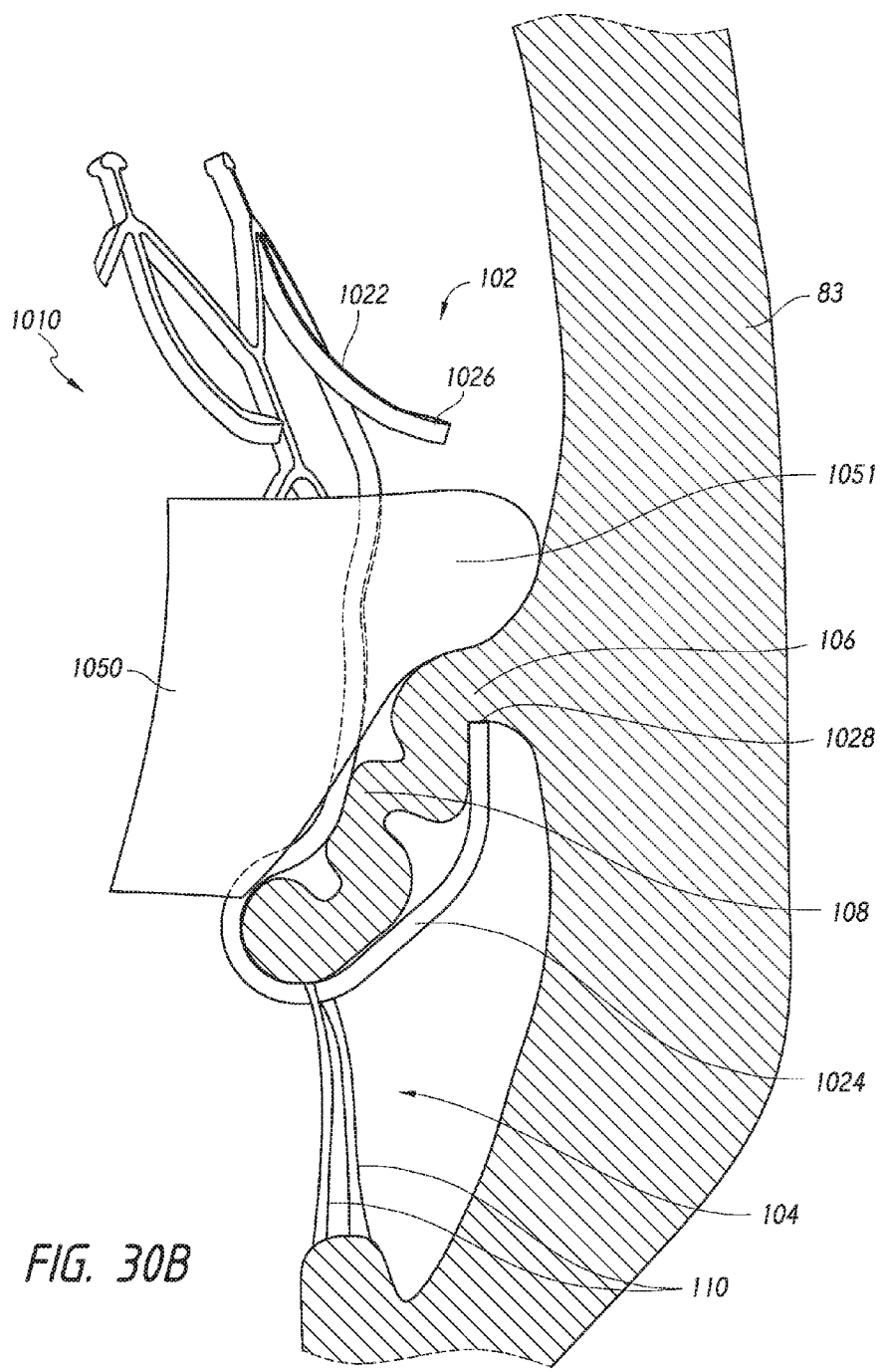
Figure 30C:
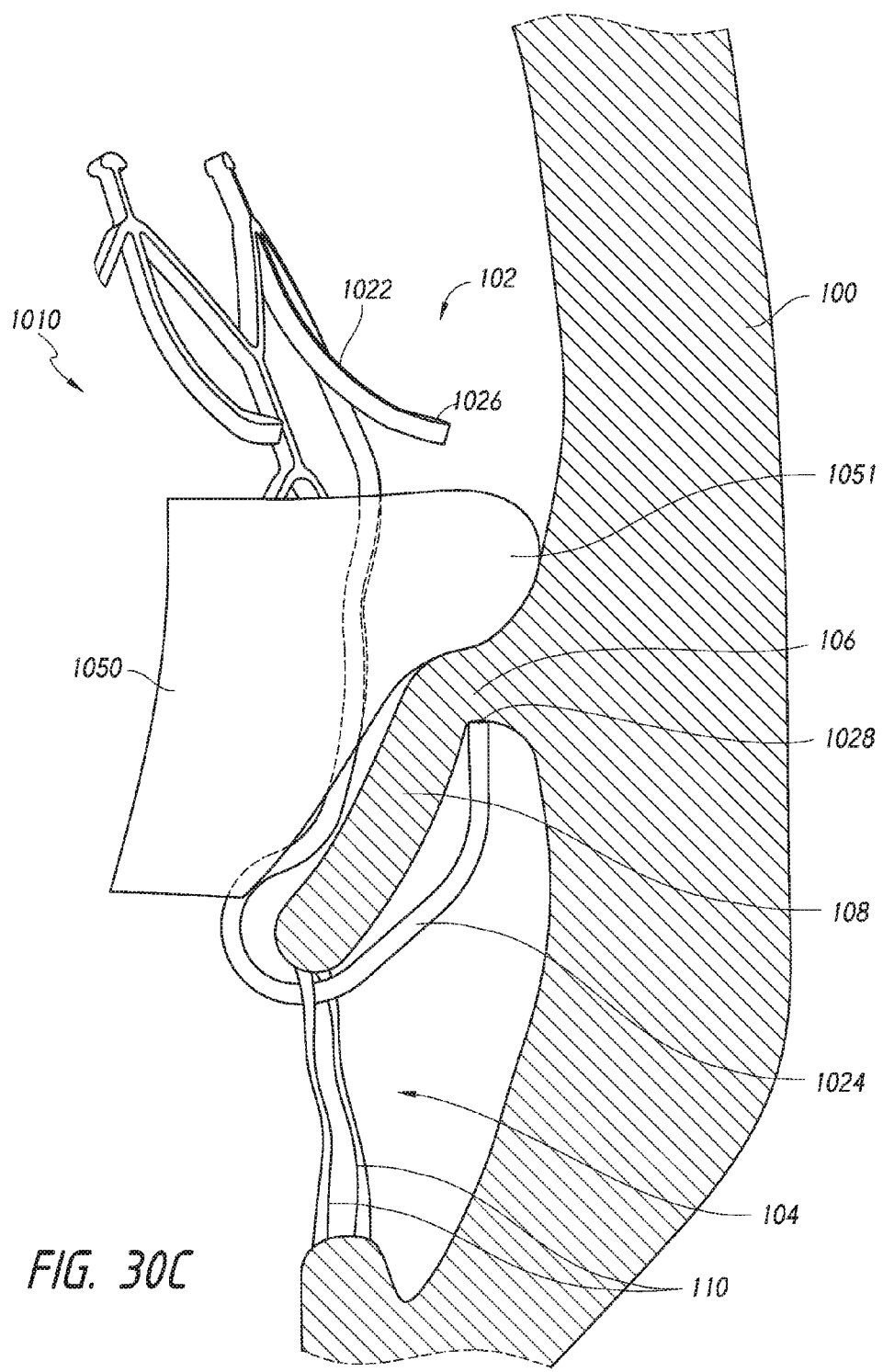
Figure 31A:
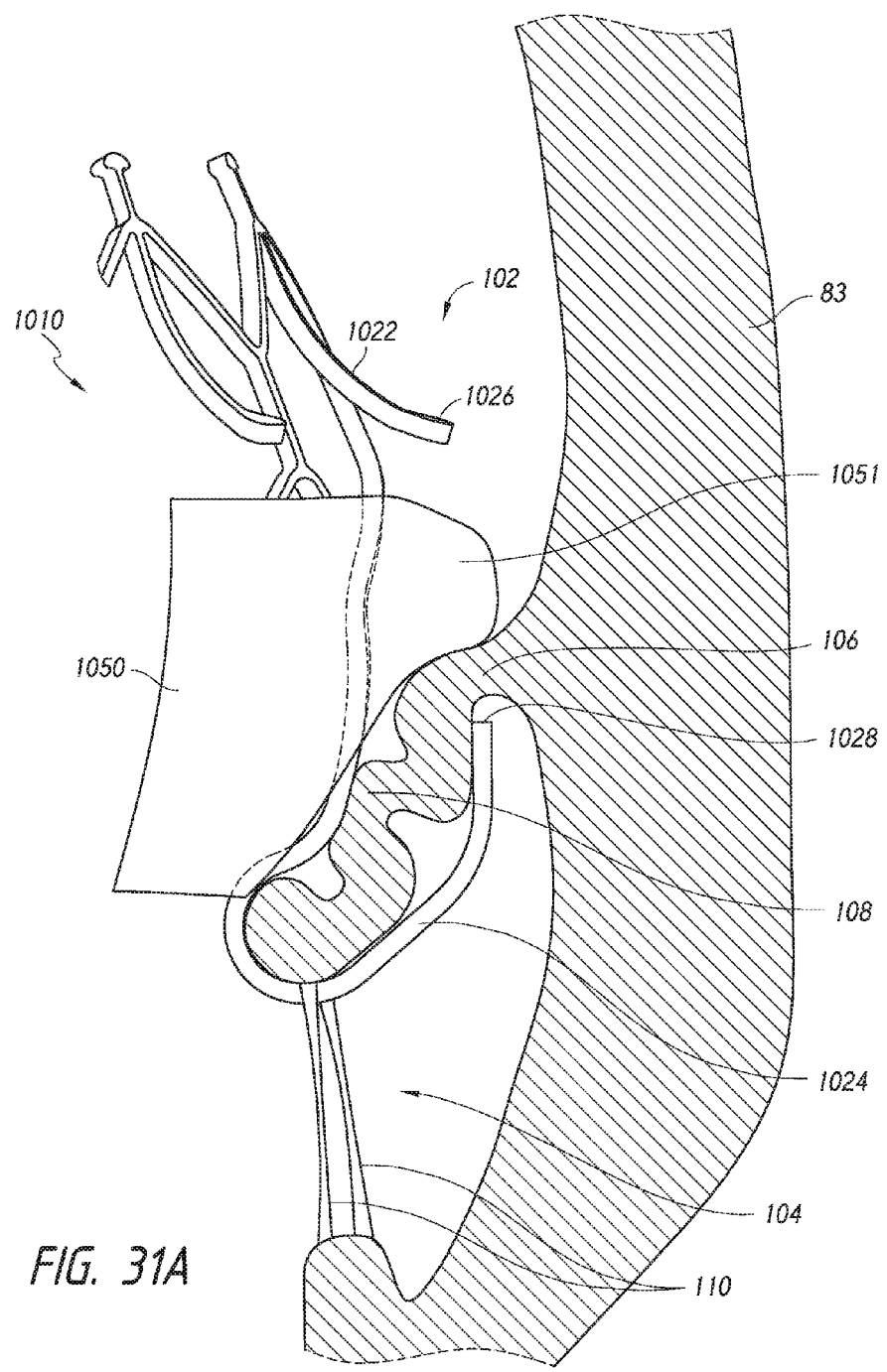
FIGS. 31A-B illustrates a schematic representation of a valve prosthesis positioned within a native mitral valve.
Figure 31B:
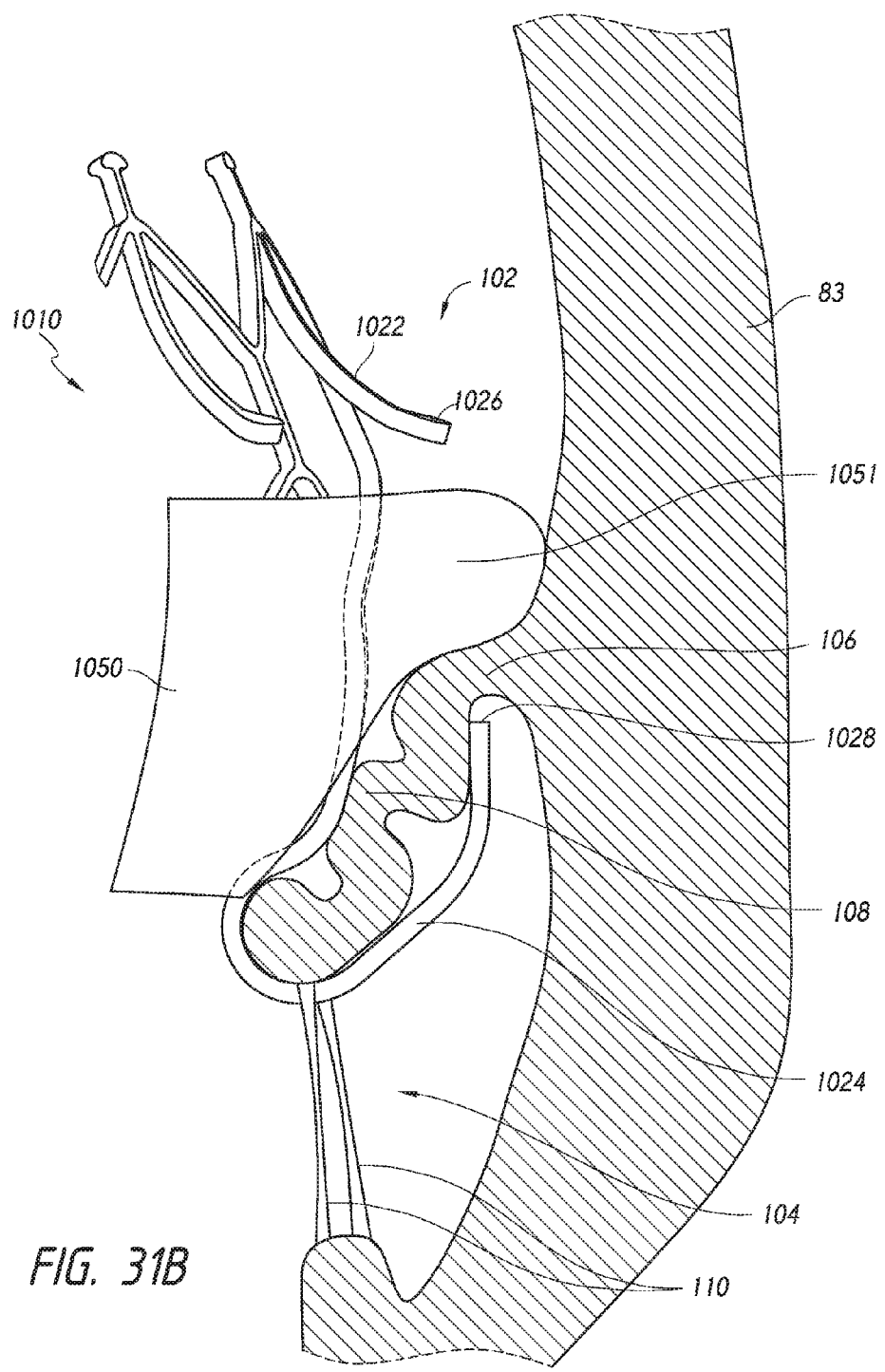

During delivery, the distal anchors 1024 (along with the frame 1010) can be moved toward the ventricular side of the annulus 106 with the distal anchors 1024 extending between at least some of the chordae tendineae 110 to provide tension on the chordae tendineae 110 after the prosthesis 1010 is finally delivered. The degree of tension provided on the chordae tendineae 110 can differ. For example, little to no tension may be present in the chordae tendineae 110 as shown in FIG. 30C where the leaflet 108 is shorter than or similar in size to the distal anchors 1024. A greater degree of tension may be present in the chordae tendineae 110 as shown in FIGS. 30A and 30B where the leaflet 108 is longer than the distal anchors 1024 and, as such, takes on a compacted form and is pulled proximally. An even greater degree of tension may be present in the chordae tendineae 110 as shown in FIGS. 31A-B where the leaflets 108 are even longer relative to the distal anchors 1024. As shown in FIGS. 31A-B, the leaflet 108 is sufficiently long such that the distal anchors 1024 do not contact the annulus 106.

The proximal anchors 1022 can be positioned such that the ends or tips 1026 of the proximal anchors 1022 are on or adjacent the atrial side of the annulus 106 and/or tissue of the left atrium 102 beyond the annulus 106. In some situations, some or all of the proximal anchors 1022 may only occasionally contact or engage atrial side of the annulus 106 and/or tissue of the left atrium 102 beyond the annulus 106. For example, as shown in FIGS. 30A-B, the proximal anchors 1022 may be spaced from the atrial side of the annulus 106 and/or tissue of the left atrium 102 beyond the annulus 106. The proximal anchors 1022 may be utilized to provide axial stability for the prosthesis 1010 and prevent off-axis orientation. Further, the proximal anchors 1022 can act as a safety feature with our without utilizing them for axial stability and off-axis orientation. For example, if the prosthesis 1010 is improperly deployed so that the valve body is deployed too low toward the left ventricle 104, the anchors 1022 can prevent the valve body from falling into the left ventricle 104. In some situations, such as those shown in FIGS. 30A and 31A, some or all of the proximal anchors 1022 may not contact the annular flap 1050. This may occur when the annular flap 1050 is in a collapsed configuration although it may also occur when the annular flap 1050 is in an expanded configuration. It is also contemplated that some or all of the proximal anchors 1022 may contact the atrial side of the annulus 106 and/or tissue of the left atrium 102 beyond the annulus 106. The particular curve of the anchors 1022 discussed above can prevent trauma to tissue of the heart 83, and can also help with stabilization of the prosthesis 1010 in the heart 83. [0134] With continued reference to the situations illustrated in FIGS. 30A-31B, the annular flap 1050 can be positioned such that a proximal portion 1051 of the annular flap 1050 is positioned along or adjacent an atrial side of the annulus 106. The proximal portion 1051 can be positioned between the atrial side of the annulus 106 and the proximal anchors 1022. The proximal portion 1051 can extend radially outward such that the annular flap 1050 is positioned along or adjacent tissue of the left atrium 102 beyond the annulus 106. The annular flap 1050 can create a seal over the atrial side of the annulus 106 when the flap 1050 is in the expanded state.

The flap 1050 can transition from the collapsed state to the expanded state during systole when pressure in the left ventricle 104 increases. This increased pressure within the left ventricle 104 can cause blood within the left ventricle 104 to be directed to areas of lower pressure, such as the aorta (not shown) and the left atrium 102. During systole the valve body may be closed to prevent blood from flowing back into the left atrium 102. A substantial portion of blood can be forced around the frame 1020 and valve body and into the annular flap 1050 such that the flap 1050 can expand. Sealing along an atrial side of the annulus 106 can be particularly effective. The left atrium 102 can be at a lower pressure in comparison to the pressure of the space between the annular flap 1050 and the valve body 1020, which is closer to the pressure of the left ventricle 104. The existence of such a pressure differential between the left atrium 102 and the space during systole can allow the flap 1050 to apply a greater force to surrounding tissue within the left atrium 102. During diastole, where blood flows from the left atrium 102 towards the left ventricle 104, the flap 1050 can transition from the expanded state back to the collapsed state.

In some situations such as those shown in FIGS. 30A and 31A, the annular flap 1050 may not contact the wall of the heart 83. This may occur when the annular flap 1050 is in a collapsed configuration although it may also occur when the annular flap 1050 is in an expanded configuration. In some situations, such as those shown in FIGS. 30B, 30C and 31B, the annular flap 1050 may contact the wall of the heart 83. This may occur when the annular flap 1050 is in an expanded configuration although it may also occur when the annular flap 1050 is in a collapsed configuration. As shown in FIG. 30A-31B, the annular flap 1050 can also assist in filling gaps which exist between the leaflet 108 and the frame 1020 (portions of which are illustrated in dashed lines).

As noted above, although the in vivo situations of FIG. 30A-31B have been described separately, it should be understood that one or more of these situations may be present when a prosthesis is positioned at the implantation location, such as a native mitral valve. For example, one or more of the distal anchors 1024 may not capture the leaflet 108 whereas the remaining anchors 1024 may capture the leaflet 108. As another example, when the prosthesis 1010 is positioned within the native mitral valve, the annular flap 1050 can contact the wall of the heart 83 along one or more portions of an outermost circumference of the proximal portion 1051 and may not contact the wall of the heart 83 along other portions of the outermost circumference of the proximal portion 1051. For example, the annular flap 1050 may contact the wall of the heart 83 along an approximately 180-degree portion of the outermost circumference of the proximal portion 1051 and may not contact the wall of the heart 83 along the remaining, approximately 180-degree portion of the outermost circumference of the proximal portion 1051.

From the foregoing description, it will be appreciated that an inventive product and approaches for implant delivery systems are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A transseptal delivery system for replacement mitral valve implantation, the delivery system comprising:
   a nose cone shaft having a proximal end and a distal end and a lumen extending therethrough;
   a nose cone provided on the distal end of the nose cone shaft;
   an inner retention shaft slideably positioned over the nose cone shaft, the inner retention shaft having a proximal end and a distal end;
   an inner retention ring provided on the distal end of the inner retention shaft, the inner retention ring configured to receive struts at a proximal portion of a replacement mitral valve prosthesis;
   a mid shaft slideably positioned over the inner retention shaft, the mid shaft having a proximal end and a distal end;
   an outer retention ring provided on the distal end of the mid shaft, the outer retention ring configured to be positioned over the inner retention ring to hold the proximal portion of the replacement mitral valve prosthesis within the inner retention ring; and
   an outer sheath assembly slideably positioned over the mid shaft and over the outer retention ring, the outer sheath assembly configured to radially restrain a distal portion of the replacement mitral valve prosthesis when the proximal portion of the replacement mitral valve prosthesis is held by the outer retention ring within the inner retention ring;
   wherein the mid shaft comprises a longitudinally pre-compressed tube located within the outer sheath assembly, the longitudinally pre-compressed tube having a reduced length of about ⅛, ⅙, ¼, ½, or 1 inches from a natural state, wherein the longitudinally pre-compressed tube is configured to lengthen during bending of the delivery system so that deflection of the mid shaft does not substantially change the location of the outer retention ring relative to the inner retention ring; and
   wherein the mid shaft provides a distal force on the outer retention ring.

2. The transseptal delivery system of claim 1, wherein the outer sheath assembly is configured to slide over the nose cone.

3. The transseptal delivery system of claim 1, further comprising a replacement heart valve prosthesis, wherein the replacement heart valve prosthesis comprises struts at a proximal portion thereof received within the inner retention ring and covered by the outer retention ring, and a distal portion covered by the outer sheath assembly.

4. The transseptal delivery system of claim 1, wherein the outer sheath assembly comprises a proximal segment and a distal segment, wherein the distal segment is configured to cover a replacement mitral valve, and wherein the distal segment is formed from two or more layers.

5. The trans septal delivery system of claim 1, wherein the outer sheath assembly comprises a distal segment configured to cover the replacement mitral valve, wherein the distal segment is formed from an inner polymer layer and an outer polymer layer, and wherein the distal segment further comprises:
   a proximal section comprising a hypotube sandwiched between the inner and outer polymer layers; and
   a distal section comprising an intermediate polymer layer sandwiched between the inner and outer polymer layers.

6. The transseptal delivery system of claim 5, wherein the distal section has a greater diameter than the proximal section.

7. The transseptal delivery system of claim 5, further comprising a polymer reinforcement in the distal section that at least partially overlaps the intermediate polymer layer.

8. The trans septal delivery system of claim 5, wherein the inner polymer layer and the outer polymer layer comprise ePTFE with generally longitudinally extending polymer chains, and the intermediate polymer layer comprises ePTFE having generally circumferentially extending polymer chains.

9. The transseptal delivery system of claim 5, wherein the hypotube comprises a plurality of circumferentially extending cuts along a longitudinal length thereof.

10. The transseptal delivery system of claim 1, wherein the longitudinally pre-compressed tube comprises a pre-compressed polymer tube.

11. The transseptal delivery system of claim 1, further comprising a spring within an interior of the outer retention ring and a cover at a distal end of the spring, wherein the spring is biased to position the cover at least partially over the inner retention ring.

12. The transseptal delivery system of claim 1, wherein the nose cone comprises an elongate hollow body that is distally tapered to facilitate bending of the nose cone when the nose cone is delivered over a guidewire and comes into contact with an internal body surface.

13. The transseptal delivery system of claim 1, further comprising a guide sheath comprising a distal tip having an open or openable wall, the distal tip being articulable to a plurality of shapes suitable for guiding components of the delivery system to the native mitral valve, wherein the outer sheath is configured to slide within a lumen of the guide sheath.

14. The transseptal delivery system of claim 1, further comprising a guidewire having an anchor assembly connected thereto, wherein the anchor assembly is configured to anchor to a heart wall.

15. The trans septal delivery system of claim 1, wherein the outer retention ring has a diameter greater than a diameter of the mid shaft.

16. The transseptal delivery system of claim 1, wherein the outer retention ring is a separate structural component attached to the mid shaft.

17. A flexible delivery system for replacement mitral valve implantation, the delivery system comprising:
- an outer sheath comprising a distal segment configured to cover a replacement mitral valve, wherein the distal segment is formed from an inner polymer wall and an outer polymer wall, and wherein the distal segment further comprises:
  - a proximal section comprising a hypotube sandwiched between the inner polymer wall and the outer polymer wall; and
  - a distal section comprising an intermediate polymer layer sandwiched between the inner and outer polymer walls;
  - wherein a proximalmost end of the intermediate polymer layer is distal from a distalmost end of the hypotube; and
- a tubular polymer reinforcement in the distal section that at least partially overlaps and is separate from the intermediate polymer layer;
- wherein the distal section has a greater diameter than the proximal section and a transition between the distal section and the proximal section is a step;
- wherein the intermediate polymer layer comprises a polymer tube separate from the inner polymer wall and the outer polymer wall;
- wherein the hypotube comprises a slotted Nitinol hypotube separate from the inner polymer wall and the outer polymer wall;
- wherein the inner polymer wall is continuous between the proximal section and the distal section;
- wherein the outer polymer wall is continuous between the proximal section and the distal section; and
- wherein the outer polymer wall and inner polymer wall are connected at a plurality of locations along the distal segment.

18. The flexible delivery system of claim 17, wherein the distal section has a greater diameter than the proximal section.

19. The flexible delivery system of claim 17, wherein the inner polymer wall and the outer polymer wall comprise ePTFE with generally longitudinally extending polymer chains, and the intermediate polymer layer comprises ePTFE having generally circumferentially extending polymer chains.

* * * * *